US012788736B2

(12) United States Patent
Avantaggiati

(10) Patent No.: US 12,788,736 B2
(45) Date of Patent: Nov. 10, 2026

(54) TREATING NON-ALCOHOLIC FATTY LIVER DISEASE AND INFLAMMATORY STEATOHEPATITIS WITH SLC25A1 INHIBITORS

(71) Applicant: GEORGETOWN UNIVERSITY, Washington, DC (US)

(72) Inventor: Maria Laura Avantaggiati, Kensington, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 1209 days.

(21) Appl. No.: 17/638,383

(22) PCT Filed: Aug. 26, 2020

(86) PCT No.: PCT/US2020/048024
§ 371 (c)(1),
(2) Date: Feb. 25, 2022

(87) PCT Pub. No.: WO2021/041561
PCT Pub. Date: Mar. 4, 2021

(65) Prior Publication Data

US 2022/0323389 A1 Oct. 13, 2022

Related U.S. Application Data

(60) Provisional application No. 62/891,775, filed on Aug. 26, 2019.

(51) Int. Cl.

| | |
|---|---|
| ***A61K 31/196*** | (2006.01) |
| ***A61K 9/08*** | (2006.01) |
| ***A61K 31/155*** | (2006.01) |
| ***A61K 31/22*** | (2006.01) |
| ***A61K 31/355*** | (2006.01) |
| ***A61K 31/366*** | (2006.01) |
| ***A61K 31/40*** | (2006.01) |
| ***A61K 31/405*** | (2006.01) |
| ***A61K 31/4192*** | (2006.01) |
| ***A61K 31/4439*** | (2006.01) |
| ***A61K 47/02*** | (2006.01) |
| ***A61P 1/16*** | (2006.01) |
| ***A61P 3/10*** | (2006.01) |

(52) U.S. Cl.
CPC .............. *A61K 31/196* (2013.01); *A61K 9/08* (2013.01); *A61K 31/155* (2013.01); *A61K 31/22* (2013.01); *A61K 31/355* (2013.01); *A61K 31/366* (2013.01); *A61K 31/40* (2013.01); *A61K 31/405* (2013.01); *A61K 31/4192* (2013.01); *A61K 31/4439* (2013.01); *A61K 47/02* (2013.01); *A61P 1/16* (2018.01); *A61P 3/10* (2018.01)

(58) Field of Classification Search
CPC .................................................... A61K 31/196
See application file for complete search history.

(56) References Cited

U.S. PATENT DOCUMENTS

2004/0019113 A1 1/2004 Jozefiak et al.
2017/0349949 A1 12/2017 Kolb

FOREIGN PATENT DOCUMENTS

WO 2019028343 2/2019

OTHER PUBLICATIONS

Alisi et al., The Role of Tissue Macrophage-Mediated Inflammation on NAFLD Pathogenesis and Its Clinical Implications, Mediators of Inflammation, vol. 2017, No. 8162421, Jan. 1, 2017, 15 pages.
Aluvila et al., Inhibitors of the Mitochondrial Citrate Transport Protein: Validation of the Role of Substrate Binding Residues and Discovery of the First Purely Competitive Inhibitor, Molecular Pharmacology, vol. 77, No. 1, Jan. 2010, pp. 26-34.
Anstee et al., From NASH to HCC: Current Concepts and Future Challenges, Nature Reviews Gastroenterology & Hepatology vol. 16, No. 7, Jul. 2019, pp. 411-428.
Brun et al., Changes in Mitochondrial Carriers Exhibit Stress-Specific Signatures in INS-1Eβ-Cells Exposed to Glucose Versus Fatty Acids, PLoS One, vol. 8, No. 12, Dec. 12, 2013, 13 pages.
Catalina-Rodriguez, et al., The Mitochondrial citrate transporter, CIC, is Essential for Mitochondrial Homeostasis, Oncotarget, vol. 3, No. 10, pp. 1220-1235, Oct. 20, 2012.
Chakravarthy et al., "New" Hepatic Fat Activates PPARalpha to Maintain Glucose, Lipid, and Cholesterol Homeostasis, Cell Metabolism, vol. 1, No. 5, May 2005, pp. 309-322.
Chaouch et al., Mutations in the Mitochondrial Citrate Carrier SLC25A1 are Associated with Impaired Neuromuscular Transmission, Journal of Neuromuscular Diseases, vol. 1, No. 1, 2014, pp. 75-90.
Cox et al., Molecular Pathways: Connecting Fibrosis and Solid Tumor Metastasis, Clinical Cancer Research, vol. 20, No. 14, Jul. 15, 2014, pp. 3637-3643.
Edvardson et al., Agenesis of Corpus Callosum and Optic Nerve Hypoplasia Due to Mutations in SLC25A1 Encoding the Mitochondrial Citrate Transporter, Journal of Medical Genetics, vol. 50, No. 4, Apr. 2013, pp. 240-245.
Fernandez et al., The Mitochondrial Citrate Carrier, SLC25A1, Drives Stemness and Therapy Resistance in Non-Small Cell Lung Cancer, Cell Death & Differentiation, vol. 25, Apr. 12, 2018, pp. 1239-1258.
Ferramosca et al., Dietary Fat and Hepatic Lipogenesis: Mitochondrial Citrate Carrier as a Sensor of Metabolic Changes, Advances in Nutrition, vol. 5, No. 3, May 14, 2014, pp. 217-225.
Flores-Tellez et al., Road to Stemness in Hepatocellular Carcinoma, World Journal of Gastroenterology, vol. 23, No. 37, Oct. 7, 2017, pp. 6750-6776.

(Continued)

*Primary Examiner* — Brian E Mcdowell
(74) *Attorney, Agent, or Firm* — Kilpatrick Townsend & Stockton LLP

(57) ABSTRACT

Provided herein are methods for treating nonalcoholic fatty liver disease (NAFLD) or nonalcoholic steatohepatitis (NASH) in a subject, comprising administering to a subject having NAFLD or NASH an effective amount of a SLC25A1 inhibitor.

5 Claims, 54 Drawing Sheets

(56) References Cited

OTHER PUBLICATIONS

Gai et al., Effects of Farnesoid X Receptor Activation on Arachidonic Acid Metabolism, NF-kB Signaling, and Hepatic Inflammation, Molecular Pharmacology, vol. 94, No. 2, Aug. 2018, pp. 802-811.
Gavito et al., Chronic IL-6 Administration Desensitizes IL-6 Response in Liver, Causes Hyperleptinemia and Aggravates Steatosis in Diet-Induced-Obese Mice, PLoS One, vol. 11, No. 6, e0157956, Jun. 22, 2016, 19 pages.
Hayashi et al., Hepatic Monoacylglycerol O-Acyltransferase 1 as a Promising Therapeutic Target for Steatosis, Obesity, and Type 2 Diabetes, Molecular Therapy—Nucleic Acids, vol. 3, e154, Mar. 18, 2014, 8 pages.
Hlouschek et al., The Mitochondrial Citrate Carrier (SLC25A1) Sustains Redox Homeostasis and Mitochondrial Metabolism Supporting Radioresistance of Cancer Cells with Tolerance to Cycling Severe Hypoxia, Frontiers in Oncology, vol. 8, No. 170, May 25, 2018, 18 pages.
Infantino et al., A Key Role of the Mitochondrial citrate Carrier (SLC25A1) in TNFα- and IFNγ-Triggered Inflammation, Biochimica et Biophysica Acta, vol. 1839, No. 11, Nov. 2014, pp. 1217-1225.
Infantino et al., Transcription of the Mitochondrial Citrate Carrier Gene: Role of SREBP-1, Upregulation by Insulin and Downregulation by PUFA, Biochemical and Biophysical Research Communications, vol. 356, No. 1, Apr. 27, 2007, pp. 249-254.
Jiang et al., Quantitative Metabolic Flux Analysis Reveals an Unconventional Pathway of Fatty Acid Synthesis in Cancer Cells Deficient for the Mitochondrial Citrate Transport Protein, Metabolic Engineering, vol. 43, Pt. B, Sep. 2017, pp. 198-207.
Jiang et al., Reductive Carboxylation Supports Redox Homeostasis During Anchorage-Independent Growth, Nature, vol. 532, No. 7598, Apr. 14, 2016, pp. 255-228.
Kazankov et al., The Role of Macrophages in Nonalcoholic Fatty Liver Disease and Nonalcoholic Steatohepatitis, Nature Reviews Gastroenterology & Hepatology, vol. 16, No. 3, Mar. 2019, pp. 145-159.
Kim et al., Acetyl CoA Carboxylase Inhibition Reduces Hepatic Steatosis but Elevates Plasma Triglycerides in Mice and Humans: A Bedside to Bench Investigation, Cell Metabolism, vol. 26, No. 2, Aug. 1, 2017, pp. 394-406.
Kolukula et al., SLC25A1, or CIC, is a Novel Transcriptional Target of Mutant p53 and a Negative Tumor Prognostic Marker, Oncotarget, vol. 5, No. 5, Mar. 15, 2014, pp. 1212-1225.
Kwan, Conditonal Alleles in Mice: Practical Considerations for Tissue-Specific Knockouts, Genesis, vol. 32, Feb. 2002, pp. 49-62.
Li et al., A *Drosophila* Model of Combined D-2- and L-2-Hydroxyglutaric Aciduria Reveals a Mechanism Linking Mitochondrial Citrate Export with Oncometabolite Accumulation, Disease Models & Mechanisms, vol. 11, No. 9, Sep. 21, 2018, 7 pages.
Losman et al., What a Difference a Hydroxyl Makes: Mutant IDH, (R)-2-Hydroxyglutarate, and Cancer, Genes & Development, vol. 27, No. 8, Apr. 15, 2013, pp. 836-852.
Mattu et al., The Metabolic Gene HAO2 is Downregulated in Hepatocellular Carcinoma and Predicts Metastasis and Poor Survival, Journal of Hepatology, vol. 64, No. 4, Apr. 2016, pp. 891-898.
Maynard et al., Mitochondrial Localization and Function of a Subset of 22q11 Deletion Syndrome Candidate Genes, Molecular and Cellular Neuroscience, vol. 39, No. 3, Nov. 2008, pp. 439-451.
Nota et al., Deficiency in SLC25A1, Encoding the Mitochondrial Citrate Carrier, Causes Combined D-2- and L-2-Hydroxyglutaric Aciduria, The American Journal of Human Genetics, vol. 92, No. 4, Apr. 4, 2013, pp. 627-631.
Palmieri et al., Discoveries, Metabolic Roles and Diseases of Mitochondrial Carriers: A Review, Biochimica et Biophysica Acta, vol. 1863, No. 10, Oct. 2016, pp. 2362-2378.
International Application No. PCT/US2020/048024, International Preliminary Report on Patentability mailed on Mar. 10, 2022, 7 pages.
International Application No. PCT/US2020/048024, International Search Report and Written Opinion mailed on Feb. 22, 2021, 10 pages.
International Application No. PCT/US2020/048024, Invitation to Pay Additional Fees and, Where Applicable, Protest Fee mailed on Nov. 19, 2020, 2 pages.
Poolsri et al., Combination of Mitochondrial and Plasma Membrane Citrate Transporter Inhibitors Inhibits De Novo Lipogenesis Pathway and Triggers Apoptosis in Hepatocellular Carcinoma Cells, BioMed Research International, vol. 2018, Article ID 3683026, Jan. 9, 2018, 15 pages.
Pop et al., An overview of Combined D-2- and L-2-Hydroxyglutaric Aciduria: Functional Analysis of CIC Variants, Journal of Inherited Metabolic Disease, vol. 41, No. 2, Mar. 2018, pp. 169-180.
Prasun et al., Expanding the Clinical Spectrum of Mitochondrial Citrate Carrier (SLC25A1) Deficiency: Facial Dysmorphism in Siblings with Epileptic Encephalopathy and Combined D, L-2-Hydroxyglutaric Aciduria, JIMD Reports, vol. 19, Jan. 2015, pp. 111-115.
Ratziu et al., Current Efforts and Trends in the Treatment of NASH, Journal of Hepatology, vol. 62, Suppl 1, Apr. 2015, pp. S65-S75.
Rodriguez et al., Dietary Downregulation of Mutant p53 Levels via Glucose Restriction: Mechanisms and Implications for Tumor Therapy, Cell cycle, vol. 11, No. 23, Dec. 1, 2012, pp. 4436-4446.
Rogers et al., The Role of INDY in Metabolism, Health and Longevity, Frontiers in Genetics, vol. 6, No. 204, Jun. 9, 2015, pp. 1-5.
Rogina et al., Extended Life-Span Conferred by Cotransporter Gene Mutations in *Drosophila*, Science, vol. 290, No. 5499, Dec. 15, 2000, pp. 2137-2140.
Rotman et al., Current and Upcoming Pharmacotherapy for Non-alcoholic Fatty Liver Disease, Gut, vol. 66, No. 1, Jan. 2017, pp. 180-190.
Schaftingen et al., Inhibition of Fructose-1,6-Bisphosphatase by Fructose 2,6-Biphosphate, Proceedings of the National Academy of Sciences of the United States of America, vol. 78, No. 5, May 1981, pp. 2861-2863.
Skarnes et al., A Conditional Knockout Resource for the Genome-Wide Study of Mouse Gene Function, Nature, vol. 474, Jun. 15, 2011, pp. 337-342.
Stojsavljevic et al., Adipokines and Proinflammatory Cytokines, the Key Mediators in the Pathogenesis of Nonalcoholic Fatty Liver Disease, World Journal of Gastroenterology, vol. 20, No. 48, Dec. 28, 2014, pp. 18070-18091.
Sumida et al., Current and Future Pharmacological Therapies for NAFLD/NASH, Journal of Gastroenterology, vol. 53, No. 3, Mar. 2018, pp. 362-376.
Sun et al., Mitochondrial and Plasma Membrane Citrate Transporters: Discovery of Selective Inhibitors and Application to Structure/Function Analysis, Molecular and Cellular Pharmacology, vol. 2, No. 3, Aug. 6, 2010, pp. 101-110.
Tan et al., Inhibition of the Mitochondrial Citrate Carrier, SLC25A1, Reverts Steatosis, Glucose Intolerance, and Inflammation in Preclinical Models of NAFLD/NASH, Cell Death & Differentiation, vol. 27, Jan. 20, 2020, pp. 2143-2157.
Toh et al., Targeting Jak/Stat Pathway as a Therapeutic Strategy Against SP/CD44+ Tumorigenic Cells in Akt/Beta-Catenin-Driven Hepatocellular Carcinoma, Journal of Hepatology, vol. 72, No. 1, Sep. 18, 2019, pp. 104-118.
Tucker et al., A Cholecystokinin Receptor Antagonist Halts Non-alcoholic Steatohepatitis and Prevents Hepatocellular Carcinoma, Digestive Diseases and Sciences, vol. 65, Jul. 11, 2019, pp. 189-203.
Willmes et al., The Longevity Gene Indy (I'm Not Dead Yet) in Metabolic Control: Potential as Pharmacological Target, Pharmacology & Therapeutics, vol. 185, May 2018, pp. 1-11.
Yasui et al., Nonalcoholic Steatohepatitis and Increased Risk of Chronic Kidney Disease, Metabolism, vol. 60, Issue 5, Sep. 3, 2010, pp. 735-739.
Ye et al., Metabolism, Activity, and Targeting of D-and L-2-Hydroxyglutarates, Trends Cancer, vol. 4, No. 2, Feb. 2018, pp. 151-165.

FIGS. 1E-J

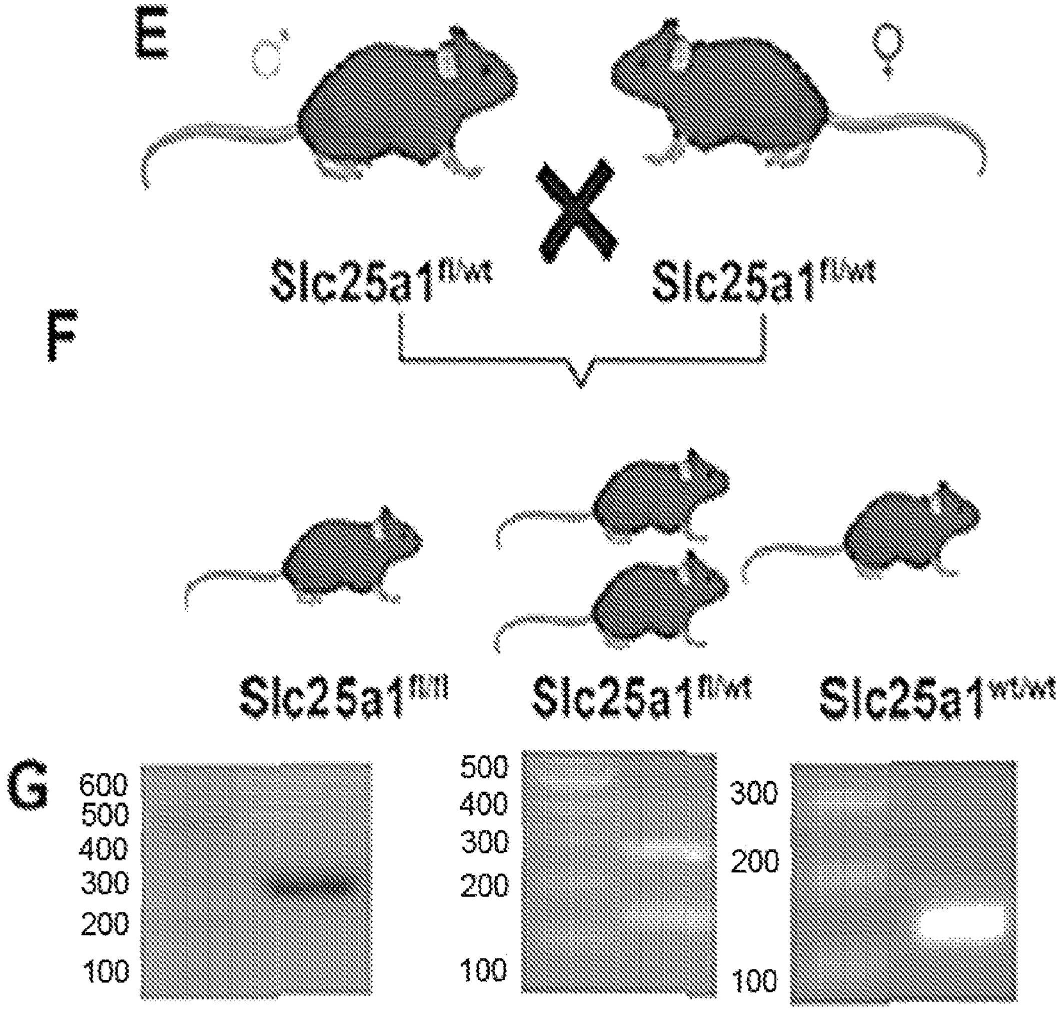
FIG. 10EFG

TREATING NON-ALCOHOLIC FATTY LIVER DISEASE AND INFLAMMATORY STEATOHEPATITIS WITH SLC25A1 INHIBITORS

CROSS-REFERENCE TO RELATED APPLICATIONS

This application is a U.S. National Phase under 35 U.S.C. § 371 of International Patent Application No. PCT/US2020/048024, filed Aug. 26, 2020, which claims priority to U.S. Provisional Application No. 62/891,775, filed Aug. 26, 2019, which are hereby incorporated in their entirety by this reference

STATEMENT REGARDING FEDERALLY FUNDED RESEARCH

This invention was made with government support under grant numbers CA923698 and DE028670 awarded by the National Institutes of Health. The government has certain rights in the invention.

BACKGROUND

Non-alcoholic fatty liver disease (NAFLD) and its evolution to non-alcoholic steatohepatitis (NASH) comprise a spectrum of manifestations that span from simple and reversible hepatic steatosis to progressive irreversible necro-inflammatory and fibrotic disease that increase the risk of hepatocellular carcinoma (HCC) and are associated with a high rate of mortality. With the development of effective therapeutics for hepatitis C, NAFDL/NASH is now predicted to become the most common cause of chronic liver disease and liver transplantation with a current worldwide prevalence as high as 25%. Individuals affected by NASH are often obese, and display insulin resistance and alterations in the lipid anabolic processes that ultimately lead to deposition and accumulation of fat deposits in the liver (steatosis). The high levels of fats in both the liver and blood (in the form of triglycerides and cholesterol) produce progressive liver damage, stimulates an inflammatory reaction that eventually leads to fibrosis and cirrhosis, and culminates in liver failure. NAFLD/NASH represents an emerging health problem that is reaching epidemic proportions, but currently there are limited options for the treatment of NAFLD/NASH.

SUMMARY

For the first time, the mitochondrial citrate carrier SLC25A1 is shown to drive the pathophysiology of NAFLD/NASH, and inhibition of this protein with a specific drug inhibitor compound is shown to halt the evolution of NASH reverting steatosis, preventing the evolution to steatohepatitis, reducing inflammation, preventing obesity and restoring normal glucose homeostasis induced by a high fat diet. Thus, provided herein are methods for treating NAFLD/NASH in a subject. The methods comprise administering an effective amount of a SLC25A1 inhibitor to a subject having NAFDL/NASH. Administration of the SLC25A1 inhibitor (e.g., CTPI-2, CTPI-1 and benzenetricarboxylate (BTA)) to the subject reduces a number of clinical signs and symptoms. For example, administration of the SLC25A1 inhibitor decreases liver steatosis, inflammation, hyperglycemia, and/or glucose intolerance and/or prevents the development of HCC in the subject as compared to a control. Optionally the SLC25A1 inhibitor is administered to the subject in combination with a second therapeutic agent (e.g., a CCK receptor inhibitor, metformin, pioglitazone, vitamin E or a statin).

Also provided herein is a pharmaceutical composition comprising a solubilized SLC25A1 inhibitor (e.g., CTPI-2, CTPI-1 or BTA), a buffering salt, and water. The pharmaceutical composition is substantially free of an organic solvent, for example, dimethyl sulfoxide (DMSO) or other solvent. The pharmaceutical composition optionally contains the SLC25A1 inhibitor at a concentration of 5 to 25 millimolar. Optionally, the buffering salt comprises sodium bicarbonate in an amount from 0.1 to 2 weight percent, based on the total weight of the solution. The pharmaceutical composition optionally further comprises sodium chloride. The pharmaceutical composition as described herein is for use in treating NAFDL/NASH and for preventing progression of NAFDL/NASH to HCC.

Also provided herein is a method of preparing a composition comprising a solubilized SLC25A1 inhibitor, such as, but not limited to CPTI-2, CPTI-1 or BTA. The method comprises the steps of providing a SLC25A1 inhibitor powder; adding water to the SLC25A1 inhibitor powder to produce an aqueous SLC25A1 inhibitor composition; adding a sodium bicarbonate solution to the aqueous SLC25A1 inhibitor composition to produce a master stock solution; and diluting the master stock solution with saline to produce the solubilized SLC25A1 composition. The method can further comprise agitating the master stock prior to the dilution step. Optionally, the aqueous SLC25A1 inhibitor composition has a concentration of SLC25A1 inhibitor from about 0.5 to about 1.5 molar. Optionally, the master stock solution comprises the sodium bicarbonate solution and aqueous SLC25A1 inhibitor composition in a ratio of about 1:1 to about 10:1 by volume.

BRIEF DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 1A shows expression levels of Slc25a1 protein in the indicated organs derived from a 4 month old male mouse. FIG. 1B, top panels; shows micrographs of tissues derived from a human normal liver (NL) and NASH patients. FIG. 1B bottom panels show Slc25a1 staining in livers of mice fed with a control diet (CD) or HFD. FIG. 1C-D show quantification of Slc25a1 staining in human NASH livers (FIG. 1C) or murine livers (FIG. 1D), as shown in FIG. 1B. Quantification was performed with the ImageJ program on multiple fields on 9 NASH livers relative to 3 normal liver. FIG. 1E shows body weight measurements of mice fed CD or HFD in the presence or absence of CTPI-2 administration over the course of 6 months (n=3-4). Measurements were taken at regular intervals. The arrow indicates the time at which CTPI-2 treatment was started, after 12 weeks of HFD-feeding. FIGS. 1F-G shows representative images of mice (FIG. 1F), or of the hemi-lateral visceral fat, WA, and liver (FIG. 1G) in the indicated diet conditions. FIG. 1H shows MRI images of the visceral fat (circled in white) of the indicated mice. Insets numbers (in white) indicate the percentage of visceral fat calculated as thresholded fat pixels versus thresholded whole body pixels in the abdominal region from every slice of the MRI image dataset (see Examples)) NS (not significant). FIG. 1I shows body weight measurements of mice fed CD and treated with CTPI-2 for 5 months (n=7). FIG. 1J shows measurement (in grams) of the indicated organs in mice fed CD, HFD-Veh., or HFD+CTPI-2 (n=3). *p≤0.05, p≤0.01,*p≤0.001.

FIG. 2A shows time course experiments showing the livers of HFD-fed mice treated with vehicle (top panels) or with CTPI-2 (bottom panels). The weeks of diet exposure are indicated at the top; the times of treatment with CTPI-2 are at the bottom. Time 0 (TO) shows the liver histology when CTPI-2 treatment was initiated. The last panel on the right (C) shows a normal liver derived from CD-fed mice. Rectangles show enlarged fields and arrows point to ballooning hepatocytes. FIGS. 2B-C show total serum cholesterol levels and alanine aminotransferase (ALT) levels measured with the Heska Element DC blood chemistry analyzer. FIG. 2D shows serum levels of triglycerides measured with LC-MS. FIG. 2E shows quantification of steatosis from the time-course experiments. The percentage of steatosis in CTPI-2 treated mice is shown on top of each bar graph. FIGS. 2F-G show quantification of liver steatosis indicated as %/per field (FIG. 2F) or steatosis grade (FIG. 2G). Quantification was performed on 3-5 mice per group and on at least 2-3 fields per mouse. Steatosis grade was assessed as: grade 0: <5%; grade 1: 5% to 33%; grade 2: 33% to 50%; and grade 3: >50%. FIG. 2H shows representative images of HFD-fed mice treated with vehicle (left panel) and of 3 different HFD-fed mice treated with CTPI-2. Rectangles show enlarged fields of the images and arrows indicate hepatocyte ballooning.

FIG. 3A shows fasting glucose levels in control diet (C, white bar), HFD-Vehicle (V, grey bar), or HFD+CTPI-2 (T, black bars) mice (n=3-6). FIG. 3B shows insulin levels (in μg/ml) of animals treated with CTPI-2 or vehicle for approximately 11 weeks (n: 2-3). FIG. 3C shows glucose tolerance test results at the indicated time points of CTPI-2 treatment (n=3-4). Δ=control diet; black lines=HFD-vehicle; red lines=HFD+CTPI-2. FIG. 3D shows insulin tolerance test in the indicated mice groups. FIG. 3E shows expression levels of Slc25a1 (shown at two different exposure times, Exp. 1 and Exp. 2) in the indicated organs (liver, pancreas and white adipose tissue (WAT)) and treatment conditions. FIG. 3F shows expression levels of Slc25a1 in the adipose tissue of mice fed with control (C), high glucose (HG), or low glucose (LG) diets (see Examples for diet composition). FIG. 3G shows fasting glucose levels in mice fed as indicated (n=4-6). *P≤0.05. =P≤0.01. *P≤0.001.

FIG. 4A shows serum levels of interleukins and chemoattractant factors from vehicle and CTPI-2 treatment groups. FIG. 4B shows quantification of liver and adipose tissue macrophages in control, vehicle treated and CTPI-2 treated mice. Quantification was performed on 2-3 mice per group and from multiple fields per mouse with the ImageJ program. FIG. 4C shows representative images of H&E and F4/80 staining in the liver. Arrows indicate crown structures. FIGS. 4D-E show quantification of macrophages in the WAT (FIG. 4D) and representative IHC images of H&E staining in the liver, visceral adipose tissue, with crown structures indicated by arrows (FIG. 4E). FIGS. 4F-G show mRNA levels of the indicated genes in the livers of vehicle or CTPI-2 treated mice. M1 and M2 are populations of macrophages. FIG. 4H show representative images of Picro-Sirius Red staining in the liver of the indicated mice. Abbreviations: iNOS: Inducible nitric oxide synthase; TNFα: tumor necrosis factor alpha; IFNγ: interferon gamma; IL 12-13; MRC1: Macrophage Mannose Receptor 1; FN1: fibronectin 1; Arg1: Arginase 1; Col4: Collagen 4; Col1a: Collagen 1a; KT19: Keratin 19; PDGFR: Platelet Derived Growth Factor Receptor Alpha; CDH1: Cadherin-1. *=P≤0.05. =P≤0.01. *P≤0.001.

FIG. 5A shows a heatmap of genes identified by RNAseq experiments in the liver of the indicated mice, after 4 weeks of CTPI-2 treatment. Enriched gene sets were identified with KEGG pathway analysis. Numbers in parenthesis report the gene ratio and the statistical significance. Relevant genes are shown in the bracket. FIG. 5B shows mRNA levels detected with RT-qPCR of the indicated genes normalized to HFD-vehicle. Most of the reported values are averages of 3 mice per group, from independent experiments. The pathways identified with RNAseq and corresponding to the relevant genes are indicated. FIG. 5C-D show immunoblot experiments with the indicated antibodies at the T1 and T2 treatment time points in the liver and WAT. The β-actin levels for each set of blots are shown.

FIGS. 6A-B show citrate and Ac-CoA levels derived from liver extracts of HFD-vehicle (light) or HFD+CTPI-2 (dark). FIGS. 6C-D show levels of the indicated triacylglycerides (TAG, (FIG. 6C)) and total fatty acids (FA, panel D) detected with the Lipidyzer platform. N=2-3 mice per group. FIG. 6E-F show levels of the indicated metabolites detected with targeted LC-MS analysis. FIG. 6G shows HepG2 cells treated with CTPI-2 for 5 hours, in the presence or absence of 5 mM sodium citrate. The indicated mRNA levels were analyzed with RT-qPCR. H. Model summarizing findings as explained in the Examples. Bars indicate Standard Deviations. *p≤0.05, p≤0.01, *p≤0.001.

FIG. 7A shows body weight measurements of wild-type or $Slc25a1^{+/-}$ mice (n: 3-6) fed a control diet, at different ages (indicated in weeks). FIGS. 7B-C show body weight of wild-type and $Slc25a1^{+/-}$ mice in HFD conditions examined over time (FIG. 7B) (triangles indicate mice fed with a normal diet), or at the end of experiments (FIG. 7C) (n=4). FIG. 7D shows immunoblots of different $Slc25a1^{+/-}$ mice (indicated from 1 to 4), in the liver and adipose tissue. FIG. 7E shows relative body weight gain of wild-type and $Slc25a1^{+/-}$ mice as compared to mouse #4. FIGS. 7F-G. Quantification of liver steatosis (FIG. 7F), and representative H&E staining (FIG. 7G) of the livers of the indicated mice. ND: Not detected. FIG. 7H is an immunoblot analysis with the indicated antibodies of the livers and WAT of $Cre/Alb^{-}:Slc25a1^{fl/fl}$ and $Cre/Alb^{+}:Slc25a1^{-/-}$ animals in CD and HFD. FIG. 7I shows quantification of liver steatosis in $Cre/Alb^{-}:Slc25a1^{fl/fl}$ and $Cre/Alb^{+}:Slc25a1^{-/-}$ animals in HFD conditions. FIG. 7J shows Magnetic Resonance Imaging (MRI) of the livers (circled and indicated by arrows in the top panels). Numbers in white indicate the percentage of liver fat calculated with MRI on all slices of the image dataset for each mouse. The bottom panels of FIG. 7J show representative H&E staining of the livers of Cre/Alb$^-$: Slc25a1$^{fl/fl}$ and Cre/Alb$^+$:Slc25a1$^{-/-}$ mice. p≤0.05, p≤0.01, *p≤0.001.

FIG. 8A shows micrographs from tissues from normal human liver and NASH patients 1-5. Data were quantified from 9 NASH samples, 5 of which (NASH-1 to 5) are shown, relative to 3 normal livers. 400× magnification. FIG. 8B shows IHC (top panels) of mice fed with control- or HFD. Sections from these slides were processed in immuno-fluorescence (IF) with DAPI and the anti-Slc25a1 antibody, and were captured with the same settings with a Perkin Elmer Vectra3 Multispectral imaging microscope with a 20× objective (bottom panels).

FIGS. 9A-B show levels of palmitate and linoleic acid in the livers detected with LC-MS. FIG. 9C show monoacyl-glycerol (MG), diacylglycerol (DG) and Phosphoglycerol (PG) obtained from the livers of control diet (white bars), HFD-vehicle (black) and HFD+CTPI-2 treated mice, detected with LCMS. (n=2-3 mice per group).

FIGS. 10A-G provide a description of SLC25A1 genetic models. SLC25A1+/− mice. FIG. 10A shows a schematic representation of the SLC25A1 targeting cassette, based on the knock-out first allele (tm1a). In the SLC25A1 gene on chromosome 16, the cassette is inserted between exon 1 and 5. The position of exon, LoxP and FRT sites is indicated. The position of the primers employed for genotyping are shown. FIG. 10B shows a genotyping strategy for the colony of SLC25A1+/− mice. The insertion of the LoxP site between exon 4 and 5 eliminates intron 4 and creates a difference of 52 bp that can be used to discriminate the genotype. The region between exon 4 and 5 was sequenced in the wild-type and mutant animals to confirm the LoxP insertion. FIG. 10C shows mRNA levels in 19 day whole embryos detected with RT-PCR and using primers spanning within exon 2 and 4 of the murine SLC25A1 mRNA. FIG. 10D shows expression levels of SLC25A1 in wild-type and heterozygous mice in the brain and liver of embryos at 19 days post-fertilization. Note that while adult mice do not express SLC25A1 in the brain (FIG. 1A), Slc25a1 levels are elevated during embryonic development. FIGS. 10E-F show a breeding strategy for generating homozygotes SLC25A1fl/fl mice: heterozygotes Slc25a1fl/wt mice were crossed to heterozygotes SLC25A1fl/wt, which resulted in litters of pups containing homozygotes SLC25A1fl/fl, which were then used for subsequent breeding into Cre-Alb mice. FIG. 10G shows primers 1 and 2 (panel A) were used to discriminate the genotype, generating an amplicon of 270 bp with the 5' FRT and loxP site in the Cre-SLC25A1fl/fl, and 136 bp in the WT allele.

FIG. 11A show MRI images (top panels) and liver histology (bottom panels) of mice fed with control diet, showing normal liver histology and liver fat content. The arrows in the MRI images indicate the liver, which is circled. FIG. 10B shows quantification of the liver fat content assessed with MRI in the indicated mice. FIG. 10C shows body weights of Alb/Cre$^-$:SLC25A1$^{fl/fl}$ or Alb/Cre$^+$: SLC25A1$^{-/-}$. FIG. 10D shows total and saturated TAGs levels in animals fed with control diet (white bars), or in Alb/Cre$^-$:SLC25A1$^{fl/fl}$ (black) or Alb/Cre$^+$:SLC25A1$^{-/-}$ (grey) animals fed the HFD. FIG. 10E shows glucose tolerance test (GTT) results in fl/fl versus −/− animals in CD or HFD conditions. (n: 3) *p≤0.05, p≤0.01, *p≤0.001. NS: non-significant.

DETAILED DESCRIPTION

Figure 1A:
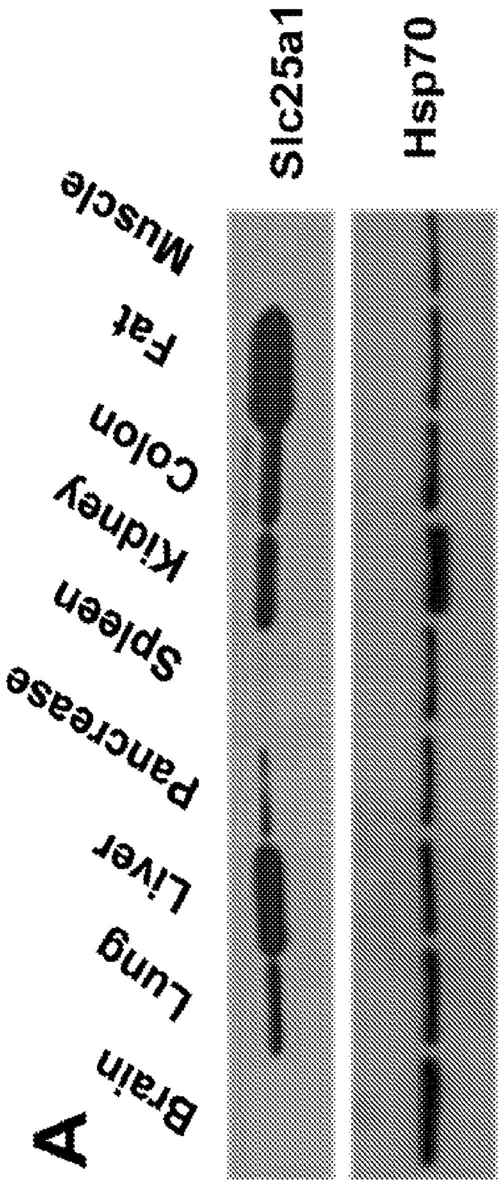
FIGS. 1A-J show that Slc25a1 levels are high in human NASH and inhibition of its activity reverts the phenotypes of mice fed a high fat diet (HFD).

Current therapies for treating NAFDL/NASH have had modest success. Weight reduction and dietary management have been treatment mainstays, but 10% or more of a patient's body weight must be lost for inflammation to decrease and fibrosis to improve. Pharmacological treatments, such as statins, have been only moderately successful. Studies using Vitamin E and pioglitazone showed the most promise in treating NASH; however, neither compound statistically reversed fibrosis and neither is recommended for those with diabetes mellitus.

Solute Carrier Family 25 Member 1 (SLC25A1) is a mitochondrial carrier that promotes the efflux of citrate from the mitochondria to the cytoplasm, in exchange for the mitochondrial entry of cytosolic malate or citrate itself. In the cytoplasm, citrate is the precursor for lipid biosynthesis and an inhibitor of glycolysis, while in the mitochondria, citrate enters the Krebs cycle and promotes mitochondrial respiration.

Methods

Provided herein is a method for treating non-alcoholic fatty liver disease (NAFLD) or nonalcoholic steatohepatitis (NASH) in a subject, comprising administering to a subject with NAFLD/NASH an effective amount of a SLC25A1 inhibitor. In any of the methods provided herein, administration of a SLC25A1 inhibitor can decrease inflammation, decrease liver steatosis, decrease liver fibrosis, reduce hyperglycemia and/or glucose intolerance, prevent the development or progression of cirrhosis and/or prevent the development or progression of HCC in a subject having NASH.

In any of the methods provided herein, the SLC25A1 inhibitor can be a compound represented by Formula I. Optionally, the SLC25A1 inhibitor can be selected from the group consisting of citrate-transporter inhibitor-1 (CTPI-1), citrate-transporter inhibitor-2 (CTPI-2) and benzenetricarboxylate (BTA) or pharmaceutically acceptable salt thereof.

Formula I

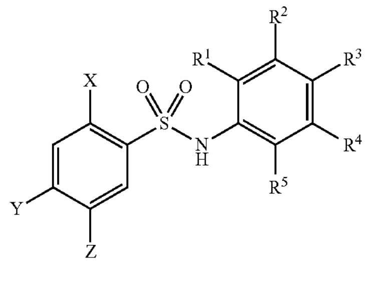

or a pharmaceutically acceptable salt or prodrug thereof.

In Formula I, R$^1$, R$^2$, R$^3$, R$^4$, R$^5$, X, Y, and Z are each independently selected from the group consisting of hydrogen, halogen (e.g., chloro, fluoro, bromo, or iodo), nitro, hydroxy, amino, alkoxy, substituted or unsubstituted carbonyl, substituted or unsubstituted alkyl, substituted or unsubstituted alkenyl, and substituted or unsubstituted alkynyl. Optionally, X is hydrogen. Optionally, Y is a halogen, such as chloro. Optionally, Z is nitro. Optionally, R$^5$ is —$CO_2H$.

In some examples of Formula I, when R$^1$, R$^2$, R$^3$, R$^5$, and Y are hydrogen, X is chloro, and Z —$CO_2H$, R$^4$ is not nitro.

Optionally, the compound of Formula I is:

CTPI-2

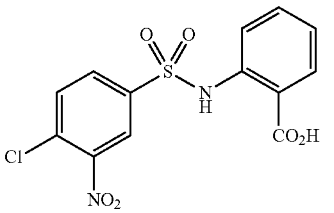

Optionally, the compound of Formula I is:

CTPI-1

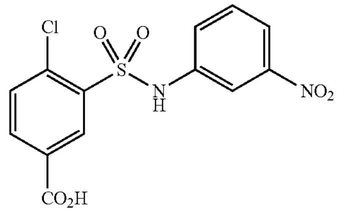

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

The term alkoxy as used herein is an alkyl group bound through a single, terminal ether linkage. The term hydroxy as used herein is represented by the formula —OH.

The terms amine or amino as used herein are represented by the formula $—NZ^1Z^2$, where $Z^1$ and $Z^2$ can each be substitution group as described herein, such as hydrogen, an alkyl, halogenated alkyl, alkenyl, or alkynyl group described above.

The alkoxy, amino, alkyl, alkenyl, alkynyl, or carbonyl molecules used herein can be substituted or unsubstituted. As used herein, the term substituted includes the addition of an alkoxy, amino, alkyl, alkenyl, alkynyl, or carbonyl group to a position attached to the main chain of the alkoxy, amino, alkyl, alkenyl, alkynyl, or carbonyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, amino, alkyl, alkenyl, alkynyl, or carbonyl has a full complement of hydrogens, i.e., commensurate with its saturation level, with no substitutions, e.g., linear decane $(—(CH_2)_9—CH_3)$.

The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein).

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety. The synthesis and subsequent testing of various compounds as described by Formula I to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H-NMR or $^{13}$C-NMR) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources. The compounds can be obtained from, for example, Sigma-Aldrich (St. Louis, Missouri), Enamine Ltd. (Kiev, Ukraine) or Santa Cruz Biotech (Dallas, TX).

In any of the methods provided herein, the SLC25A1 inhibitor or antagonist can be a SLC25A1 inhibitor or antagonist that inhibits at least one activity of SLC25A1, for example, the flux of citrate/isocitrate across the mitochondria of a cell. In any of the methods provided herein, the SLC25A1 inhibitor can decrease steatosis and/or fibrosis in the subject, for example, liver steatosis and/or fibrosis.

As used throughout, fibrosis, refers to a process resulting in excess deposition of extracellular matrix components, for example, collagen. See, for example, Cox and Erler "Molecular Pathways: Connecting Fibrosis and Solid Tumor Metastasis," *Clin Cancer Res;* 20(14); 3637-43, hereby incorporated in its entirety by this reference. In any of the methods provided herein, a decrease in fibrosis can be a decrease of about 10, 20, 30, 40, 50, 60, 70, 80, 90% or greater when compared to fibrosis in the subject prior to treatment with a SLC25A1 antagonist or when compared to a control subject or control value.

As used throughout, liver steatosis or hepatic steatotis refers to an increase or accumulation of fat in the liver. In some instances, hepatic steatosis can refer to intrahepatic fat of at least 5% of liver weight. In any of the methods provided herein, a decrease in steatosis can be a decrease of about 10, 20, 30, 40, 50, 60, 70, 80, 90% or greater when compared to fibrosis in the subject prior to treatment with a SLC25A1 antagonist or when compared to a control subject or control value.

Any of the methods provided herein can further comprise administering a second therapeutic agent (in combination therapy) to the subject. In some methods, the second therapeutic agent is a CCK receptor inhibitor (see, for example, Tucker et al. "A Cholecystokinin Receptor Antagonist Halts Nonalcoholic Steatohepatitis and Prevents Hepatocellular Carcinoma," *Dig. Dis. Sci.* 2019 Jul. 11. doi: 10.1007/s10620-019-05722-3) metformin, pioglitazone, vitamin E or a statin (for example, lovastatin, atorvastatin, simvastatin, pravastatin, rosuvastatin or fluvastatin). It is understood that two or more second therapeutic agents can be administered to the subject. Optionally, the SLC25A1 inhibitor and/or the second therapeutic agent can be administered at a dosage lower than the dosage administered to the subject when the SLC25A1 inhibitor or second therapeutic agent is delivered as a monotherapy. Alternatively, the SLC25A1 inhibitor can be administered in conjunction with other therapies for liver disease. For example, the composition can be administered to a subject at the same time, prior to, or after surgery, immunotherapy, transplant therapy or other pharmacotherapy.

In some methods, the SLC25A1 inhibitor is administered in conjunction with a chemotherapeutic agent to prevent progression of HCC. The chemotherapeutic can be administered prior to, concurrently with or subsequent to treatment with a SLC25A1 inhibitor. Examples of chemotherapeutic agents include, but are not limited to, antineoplastic agents such as Acivicin; Aclarubicin; Acodazole Hydrochloride; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin C; Mitosper; Mitotane; Mitoxantrone; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Other chemotherapeutic agents that can be used include, sorafenib, brivanib, sunitinib, linifanib, erlotinib, everolimus, ramucirumab, regorafenib, lenvatinib, cabozantinib, tivantinib, apatinib, to name a few. Any of the methods provided herein for preventing HCC can optionally further include administering radiation therapy to the subject.

Any of the methods provided herein can further comprise weight loss and/or dietary modifications for the subject. For example, the subject can limit fat intake, replace saturated fats and trans fats with monounsaturated fats and polyunsaturated fats, reduce sugar intake, avoid alcohol use, reduce dairy consumption and/or reduce sodium intake.

The methods provided herein can further comprise diagnosing the subject with NAFLD or NASH. For example, and not to be limiting, an MRI elastography, a liver biopsy, an ultrasound, Fibroscan, and/or a blood test (for example, NASH Fibrosure®) to assess liver function can be used to diagnose NASH. It is also understood that any of the methods provided herein can be used to treat a subject suspected of having NAFLD or NASH.

Treating or treatment of any disease or disorder refers to ameliorating a disease or disorder that exists in a subject. The term ameliorating refers to any therapeutically beneficial result in the treatment of a disease state, (e.g., NAFDL/NASH), such as lessening in the severity or progression, promoting remission or durations of remission, or curing thereof. Thus, treating or treatment includes ameliorating at least one physical parameter or symptom. Treating or treatment includes modulating the disease or disorder, either physically (e.g., stabilization of a discernible symptom) or physiologically (e.g., stabilization of a physical parameter)

or both. Treating or treatment includes delaying or preventing progression of NAFDL/NASH. It is understood that progression of NAFDL/NASH can result in fibrosis, steatosis, cirrhosis and/or HCC. Therefore, treating NAFDL/NASH can also prevent the development or progression of fibrosis, steatosis, cirrhosis and/or HCC. In the disclosed methods, treatment can refer to a 10%, 20%, 30%, 40%, 50%, 60%, 70%, 80%, 90%, or 100% reduction in the severity of an established disease or condition or symptom of the disease or condition. For example, a method for treating NAFDL/NASH is considered to be a treatment if there is a 10% reduction in one or more symptoms of the disorder (for example, inflammation, pain, swelling etc.), a decrease in steatosis (for example, NAFDL/NASH-associated liver steatosis), a reduction in the severity of NAFDL/NASH, the complete ablation of NAFDL/NASH, or a delay in the onset or worsening of one or more symptoms of NASH. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As used herein, the term therapeutically effective amount or effective amount is defined as any amount necessary to produce a desired physiologic response, for example, treating a disease or disorder. A suitable dose of a SLC25A1 inhibitor described herein, which dose is capable of treating NAFDL/NASH in a subject, can depend on a variety of factors including whether it is used concomitantly with other therapeutic agents. Other factors affecting the dose administered to the subject include, e.g., the severity of NAFDL/NASH Other factors can include medical issues or disorders concurrently or previously affecting the subject (for example, diabetes, high cholesterol, hypothyroidism, etc.), the general health of the subject, the genetic disposition of the subject, diet, time of administration, rate of excretion, drug combination, age or size of the subject, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

Exemplary dosage amounts for administration of a SLC25A1 inhibitor include doses from about 0.0001 to about 200 mg/kg of body weight of active compound per day, which may be administered in a single dose or in the form of individual divided doses, such as from 1 to 4 times per day. Alternatively, the dosage amount can be from about 0.01 to about 150 mg/kg of body weight of active compound per day, about 0.1 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein.

Effective amounts and schedules for administering a SLC25A1 inhibitor can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily.

Pharmaceutical Compositions

The SLC25A1 inhibitor described herein can be provided in a pharmaceutical composition. These include, for example, a pharmaceutical composition comprising a therapeutically effective amount of one or more SLC25A1 inhibitors and a pharmaceutical carrier.

Exemplary pharmaceutical compositions include a pharmaceutical composition comprising a solubilized SLC25A1 inhibitor (e.g., CTPI-2, CTPI-1, or BTA), a buffering salt, and water. The pharmaceutical composition is substantially free of an organic solvent, for example, dimethyl sulfoxide (DMSO) or other solvent. SLC25A1 inhibitor is optionally present in the pharmaceutical composition at a concentration of about 5 to about 25 millimolar. For example, the SLC25A1 inhibitor is optionally present at a concentration of about 5, 6, 7, 8, 9, 10, 11, 12, 13, 14, 15, 16, 17, 18, 29, 20, 21, 22, 23, 24, 25 millimolar, or any concentration in between these concentrations. Optionally, the buffering salt comprises sodium bicarbonate in an amount from 0.1 to 2 weight percent, based on the total weight of the solution. For example, the buffering salt optionally comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 weight percent or any weight percent in between these weight percentages. The pharmaceutical composition optionally further comprises sodium chloride.

Also provided is a method of preparing a solubilized SLC25A1 inhibitor composition, comprising: (a) providing a SLC25A1 inhibitor powder; (b) adding water to the SLC25A1 inhibitor powder to produce an aqueous SLC25A1 inhibitor composition; (c) adding a sodium bicarbonate solution to the aqueous SLC25A1 inhibitor composition to produce a master stock solution; and (d) diluting the master stock solution with saline to produce the solubilized SLC25A1 composition. Optionally, the SLC25A1 inhibitor is selected from the group consisting of CPTI-2, CPTI-1 and BTA. Optionally, the method can further comprise agitating the master stock solution prior to the diluting step. Optionally, the aqueous SLC25A1 inhibitor composition has a concentration of SLC25A1 inhibitor of from 0.5 to 1.5 molar. For example, the aqueous SLC25A1 inhibitor composition can have a concentration of SLC25A1 inhibitor of about 0.5, 0.6, 0.7, 0.8, 0.9, 1.0, 1.1, 1.2, 1.3, 1.4 or 1.5 molar. Optionally, the master stock solution comprises the sodium bicarbonate solution and aqueous SLC25A1 inhibitor composition in a ratio of from 1:1 to 10:1 by volume. For example, the master stock solution can comprise the sodium bicarbonate solution and aqueous SLC25A1 inhibitor composition in a ratio of from 1:1, 2:1, 3:1, 4:1, 5:1, 6:1, 7:1, 8:1, 9:1 or 10:1 by volume.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers optionally include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, New Jersey), polyethylene glycol (PEG), and PLURONICS™ (BASF; Florham Park, NJ).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired and on the area to be treated. The compositions are administered via any of several routes of administration, including orally, parenterally, intravenously, intraperitoneally, intramuscularly, subcutaneously, intrarectally, intracavity or transdermally. Pharmaceutical compositions can also be delivered locally to the area in need of treatment (e.g., to the liver), for example by local application (e.g., during surgery) or local injection. Administration can also be achieved by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; and European Patent Nos. EP488401 and EP 430539. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

Effective doses for any of the administration methods described herein can be extrapolated from dose-response curves derived from in vitro or animal model test systems.

Transgenic Non-Human Animals

Provided herein is a conditional knock-out non-human animal, wherein the genome of some of the cells in the non-human animal is modified to comprise a conditionally disrupted SLC25A1 coding sequence, wherein the disruption results in an inability of the non-human animal to produce detectable levels of SLC25A1 in the liver. The conditional disruption is induced by breeding a non-human animal with floxed/floxed SLC25A1 alleles with a non-human animal expressing a Cre recombinase under the control of a liver-specific promoter, and wherein the disruption results in at least one phenotype of the non-human animal selected from the group consisting of obesity, NAFLD, NASH, and HCC. Optionally, the liver specific promoter is an albumin promoter. Optionally, the knock-out non-human animal further comprises a mutation or disruption in a coding sequence for p53 or PTEN. Optionally, the non-human animal is a mouse, a rabbit, a rat or a hamster.

Also provided is a method of making a conditional knock-out non-human animal described herein comprising breeding a non-human animal with floxed/floxed SLC25A1 alleles with a non-human animal expressing a Cre recombinase under the control of a liver-specific promoter. As used herein floxed or floxing means that SLC25A1 alleles are flanked by LoxP sites. Recombination between LoxP sites is catalyzed by Cre recombinase. Floxing a gene allows it to be deleted (knocked out), translocated or inverted during Cre-lox recombination. See, for example, Kwan "Conditional Alleles in Mice: Practical Considerations for Tissue-Specific Knockouts," *Genesis* 32: 49-62 (2002)).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Cells, reagents, antibodies, primers. CTPI-2 was purchased from Enamine Ltd. (Monmouth Jct, NJ). The anti-SLC25A1 antibody used in immunoblots was either from Santa Cruz Biotech (Dallas, TX), (#sc-86392), employed at 1:1000 dilution, or from Proteintech (15235-1-AP, Rosemont, IL), employed at 1:1000 dilution.

Mice and diets. For the majority of the experiments (except for experiments harboring genetic alterations of the Slc25a1 gene), DIO C57BL/6J mice were purchased from Jackson Laboratory (Bar Harbor, ME) between 4-6 weeks of age. Mice were acclimated in the Georgetown University animal facility for at least one week. At the indicated times, mice were randomized to a standard laboratory chow diet (Labdiet #5053, St. Louis, MO) or the high fat diet (Researchdiets D12492, New Brunswick, NJ), with 60% calories derived from fat (lard), and 20% from sucrose. During the course of the experiments, mice were housed at one mouse per cage and food consumption was measured regularly. Animals were maintained in a normal light-cycle and provided with water ad libitum.

CTPI-2 treatment. CTPI-2 was administered at 50 mg/kg via intra-peritoneal injection on alternate days. CTPI-2 was diluted either in DMSO (at 0.2% final concentration) using DMSO as vehicle control, or in 0.47% Sodium Bicarbonate ($NaCO_3$) at a final concentration of 14 mM. $NaCO_3$ (0.47%) served as vehicle control.

Immunoblot of murine tissues. Frozen tissue samples were homogenized in radioimmunoprecipitation (RIPA) buffer with protease inhibitor cocktails. Protein quantification was done by using a Coomassie (Bradford) Protein Assay Kit (Pierce, Waltham MA). Equal amount of protein lysate was loaded and separated by Novex™ 4-20% Tris-Glycine Mini Gel (Invitrogen, Carlsbad, CA), then transferred to a PVDF membrane. Appropriate horseradish peroxidase-conjugated secondary antibody (Invitrogen) was applied after incubation with primary antibody. SuperSignal™ West Pico PLUS Chemiluminescent Substrate (Thermo Fisher Scientific, Waltham, MA) was used for protein detection.

SLC25a1 strains. The original Slc25a1 tm1a strain was purchased from the Mutant Mouse Resource and Research Center (MMRRC, Chapel Hill, NC) (C57BL/6N-

$Slc25a1^{tm1a(EUCOMM)Wtsi}$, RRID: MMRRC_042258-UCD). The Tg(Alb-cre)21M (Alb-Cre) mice were purchased from Jackson Laboratory (#003574). $Slc25a1^{+/-}$, $Slc25a1^{fl/fl}$ and Alb/Cre mice were genotyped by conventional PCR with genomic DNA extracted from the mouse tail biopsies. Agarose gel electrophoresis was used for analysis of PCR product analysis. The PCR conditions used were as follows: 95° C. for 4 minutes, followed by 40 cycles (95° C. for 30 seconds, 65° C. for 30 seconds, and 72° C. for 50 seconds), 72° C. for 2 min then kept in 4° C. before used.

Histological Analysis. Assessment of steatosis was performed on paraffin embedded H&E stained sections derived from 3-6 animals and on multiple images for each animal. The steatosis grade was scored according to the degree of liver involvement with 0, <5%; 1, 5% to 33%; 2, 33% to 50%; and 3, >50%. Alternatively, the percentage of steatosis per area was calculated with ImageJ program.

Lypidomic analysis. Targeted quantitation of triglycerides was performed using multiple reaction monitoring mass spectrometry. The samples were resolved on an CORTECS T3 2.7 μm, 2.1×30 mm column online with a triple quadrupole mass spectrometer (Xevo-TQ-S, Waters Corporation, Milford, MA) operating in the multiple reaction monitoring (MRM) mode. Signal intensities from all MRM Q1/Q3 ion pairs for triglycerides were ranked to ensure selection of the most intense precursor and fragment ion pair for MRM-based quantitation. This approach resulted in selection of cone voltages and collision energies that maximized the generation of each fragment ion species. The LC and MRM method used here for the study was developed by Waters Corporation. The metabolite ratios were calculated by normalizing the peak area of endogenous metabolites within tissue samples normalized to the internal standard. Processed data was normalized with respect to tissue weight taken for analysis. The quantitative measurement of lipids with the Lipidyzer platform was performed on the 5500 QTrap with SelexION (Sciex, Framingham, MA). The relative quantification values of analytes were determined by calculating the ratio of intensity of transitions of samples normalized to the intensity of the internal standard for 20 infusion cycles.

RNA isolation, mRNA sequencing and analysis. Total RNA was isolated from cell pellets using the Direct-zol RNA MiniPrep kit (Zymo Research, Irvine, CA). The RNA quality and quantity were estimated by UV-VIS spectrophotometry using the NanoDrop ND-1000 spectrophotometer (Thermo Fisher Scientific). RNA integrity was assessed using the Agilent RNA 6000 Nano Kit on the Agilent 2100 Bioanalyzer (Santa Clara, CA) to calculate DV200 (the fraction of RNA molecule>200 nt). Final RNA yield and concentration was measured using the Qubit RNA HS Assay Kit (Thermo Fisher Scientific), and subsequently normalized to the same concentration across all samples before input. RNA sequencing was performed by the UCLA center for Neurobehavioral Genetics. mRNA libraries were prepared using TruSeq Illumina standard library preparation protocols. For RNAseq enrichment profiling gene-level quantification was performed using the alignment-free Salmon tool with GRCm38 Mus musculus GENCODE (vM21) annotation. The R package tximport was used to summarize to gene level quantification, and the R package DESeq2 was used to perform normalization and differential expression analyses. Hierarchical clustering was used to separate gene expression profiles using the "ward.D" algorithm on Euclidean distance matrices. Dendrogram trees were cut and labeled using the dendextend R package, and cluster-wise enrichment was calculated using KEGG pathway annotation and the clusterProfiler R package.

Immunohistochemistry, Immunofluorescence and NASH Tissue Microarrays. The tissue arrays of human NASH were obtained from XenoTech (1910017, Kansas City, KS). The IHC was performed using standard protocols on formalin-fixed sections. Immunohistochemical staining of mouse liver was performed with SLC25A1 antibody. Five-micron sections from formalin fixed paraffin embedded tissues were de-paraffinized with xylenes and rehydrated through a graded alcohol series. Heat induced epitope retrieval (HIER) was performed by immersing the tissue sections in Target Retrieval Solution, Low pH (DAKO) in the PT Link (DAKO). Briefly, slides were treated with 3% hydrogen peroxide, avidin/biotin blocking, and 10% normal goat serum and exposed to primary antibodies for 1 hour at room temperature. The SLC25A1 antibody (ProteinTech, Cat. 15235-1-AP) was used at 1/150 dilution. Slides were exposed to biotin-conjugated anti-rabbit secondary antibodies (Vector Labs) diluted 1/200 into ImmPress Rat mouse absorbed HRP-conjugated anti-rat secondary antibody (Vector Laboratories, Inc., Burlingame, CA, cat. MP-7444). Protein expression was visualized using TSA-488 (Life Technologies, Carlsbad, CA, cat. #T20948) and Cy3-SA (Perkin Elmer, Waltham, MA, cat. #SAT704A001), nuclei visualized with DAPI and the slides mounted in ProLong Anti-fade Gold (Life Technologies P36930). Consecutive sections with the primary antibody omitted were used as negative controls. Stained slides were scanned using the Vectra3 Multi-Spectral Imaging Microscope with Vectra and Phenochart software (Perkin Elmer). The entire slide was scanned, then 10 regions of interest were randomly selected throughout the tissue. The scanned images were analyzed in inForm software version 2.4.1 (Atlanta, GA).

Magnetic Resonance Imaging techniques. In vivo magnetic resonance imaging (MRI) of mouse fat depots was performed in the Preclinical Imaging Research Laboratory at the Georgetown-Lombardi Animal Shared Resource and the Center for Translational Imaging in a 7-Tesla horizontal Bruker spectrometer run by Paravision 5.1 (Billerica, MA). Anesthetized (1.5% isoflurane in a gas mixture of 30% oxygen and 70% nitrous oxide) mice were placed in a custom-manufactured (ASI Instruments, Warren, MI) stereotaxic device with built-in temperature and cardio-respiratory monitoring engineered to fit a Bruker mouse volume coil. The sequence used to non-invasively identify adipose tissue was a three-dimensional T1-weighted rapid acquisition with rapid enhancement (RARE) sequences with the following parameters: TR: 250 ms, TE: 34.3 ms, FA: 74.1, Matrix: 156×128×156. Quantification of visceral fat depots in the imaging datasets was performed by thresholding and voxel-counting with ImageJ software (NIH). Specifically, maximum intensity projection algorithm of the 3D-reconstructed image, with an intensity threshold that shows fat as the brightest signal and disregards signals from other tissues, was used. Total body fat was calculated and specific fat depots in the regions of interest (ROI) were separated. Liver fat content was determined by placing large ROIs on liver regions and measuring the mean intensity of the fat contrast. Liver ROIs in three slices of each dataset were averaged. Values were normalized to the mean intensity of ROIs placed on background air in each corresponding slice as an internal standard.

Statistics. Statistical significance was assessed using both paired or unpaired, two-tailed Student's t test. Significant differences are indicated using the standard Michelin Guide scale (*p<0.05, significant; p<0.01, highly significant; *p<0.001, extremely significant).

Results

Figure 1B:
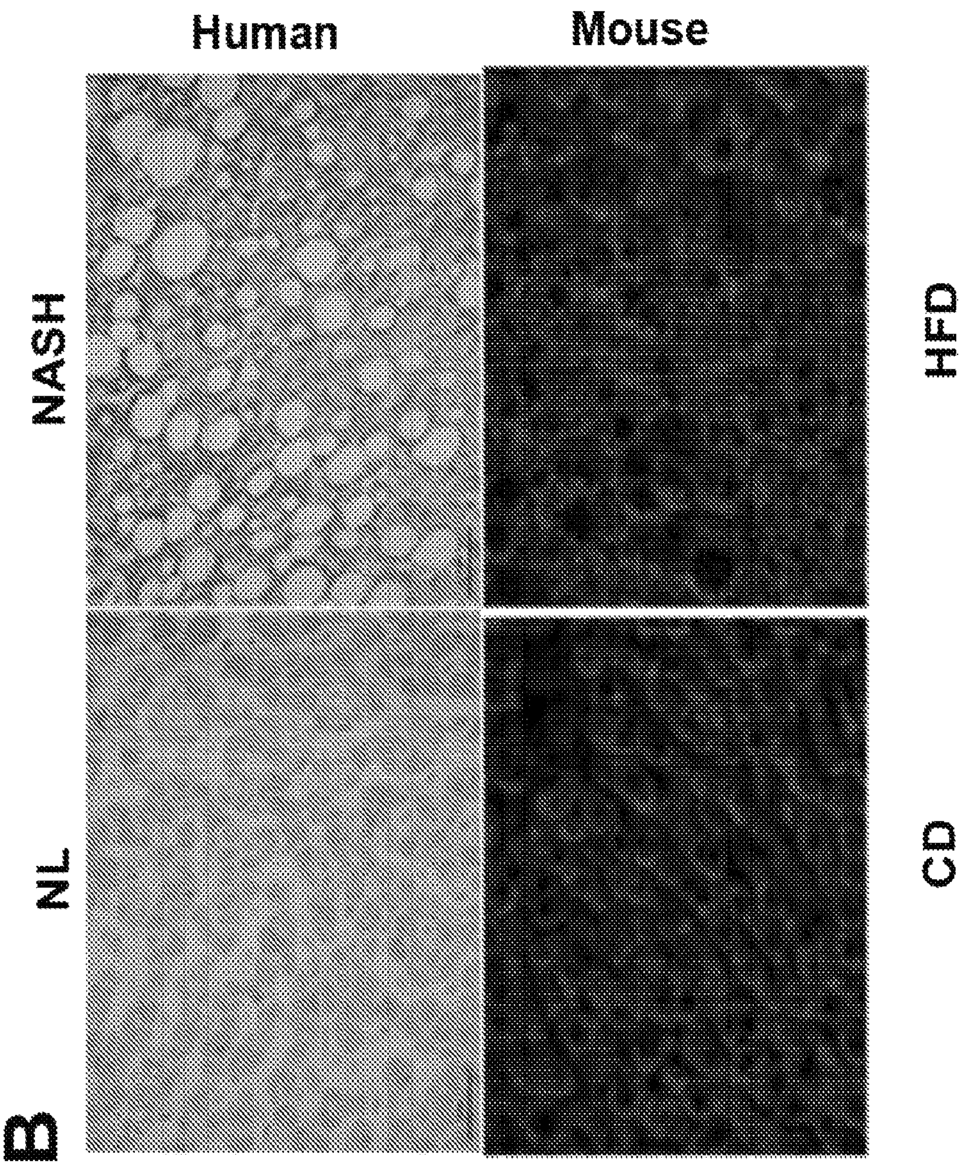
Figures 1C, 1D:
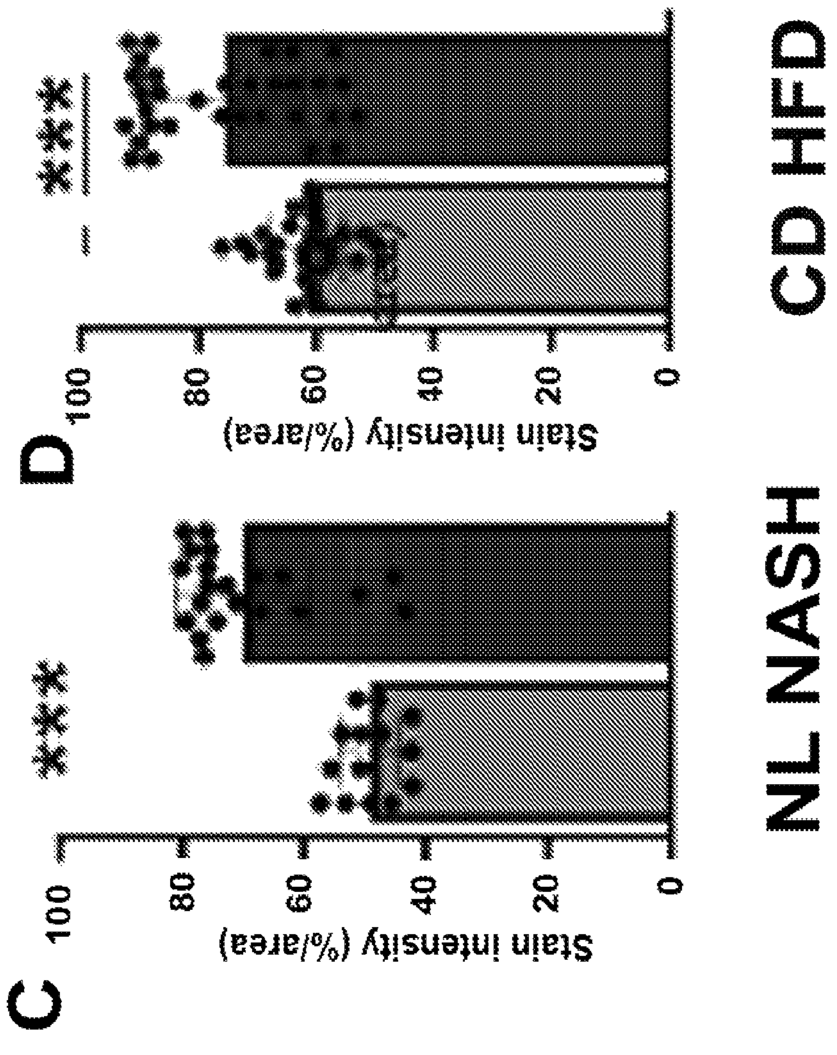
Figure 1E:
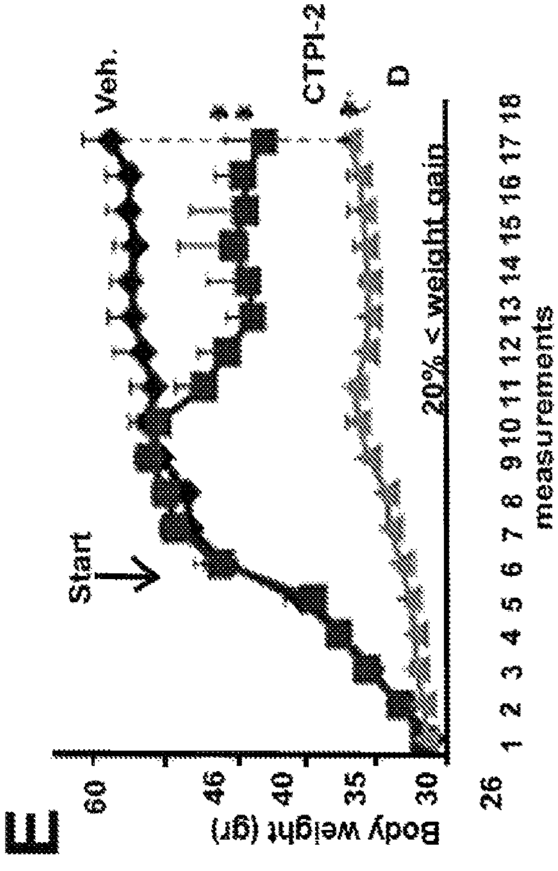
Figure 1F:
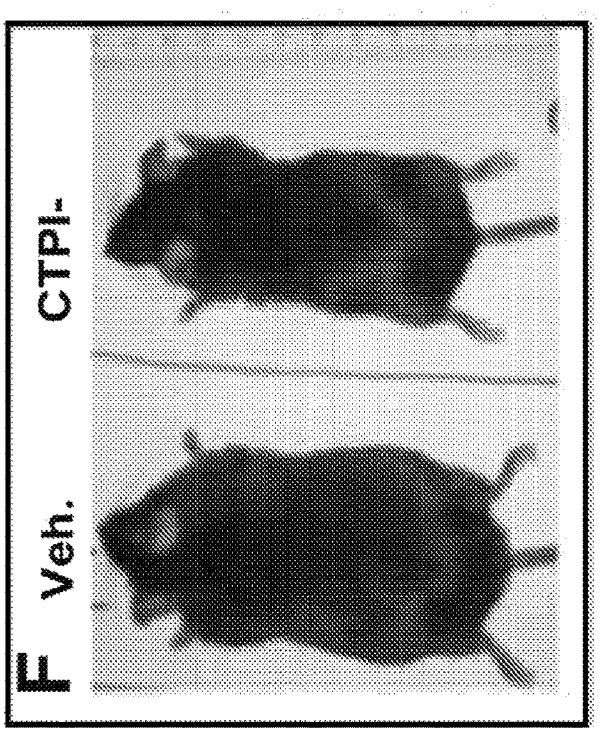
Figure 8A:
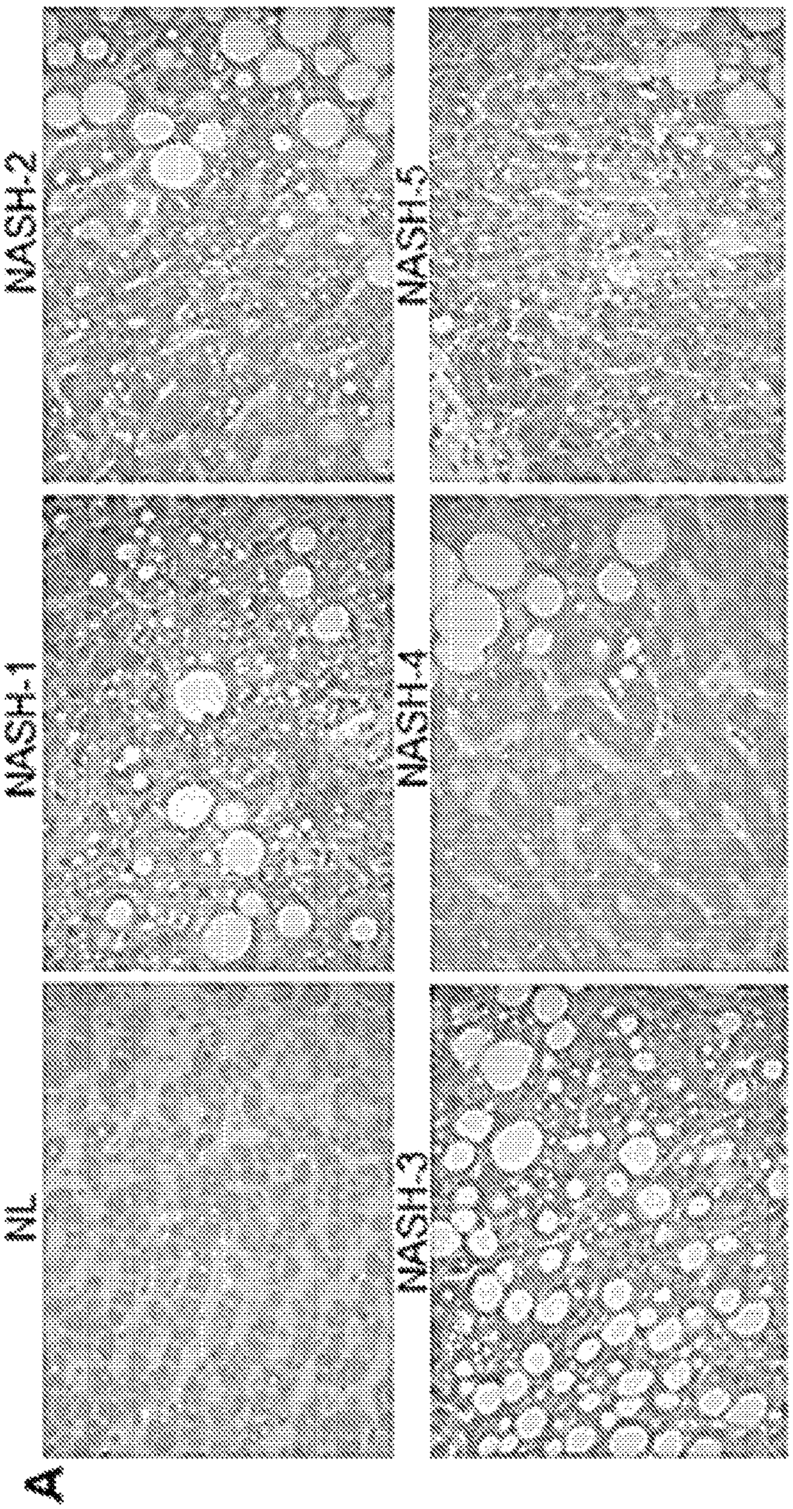
FIGS. 8A-B show that Slc25a1 is highly expressed in human and murine NASH livers.
Figure 8B:
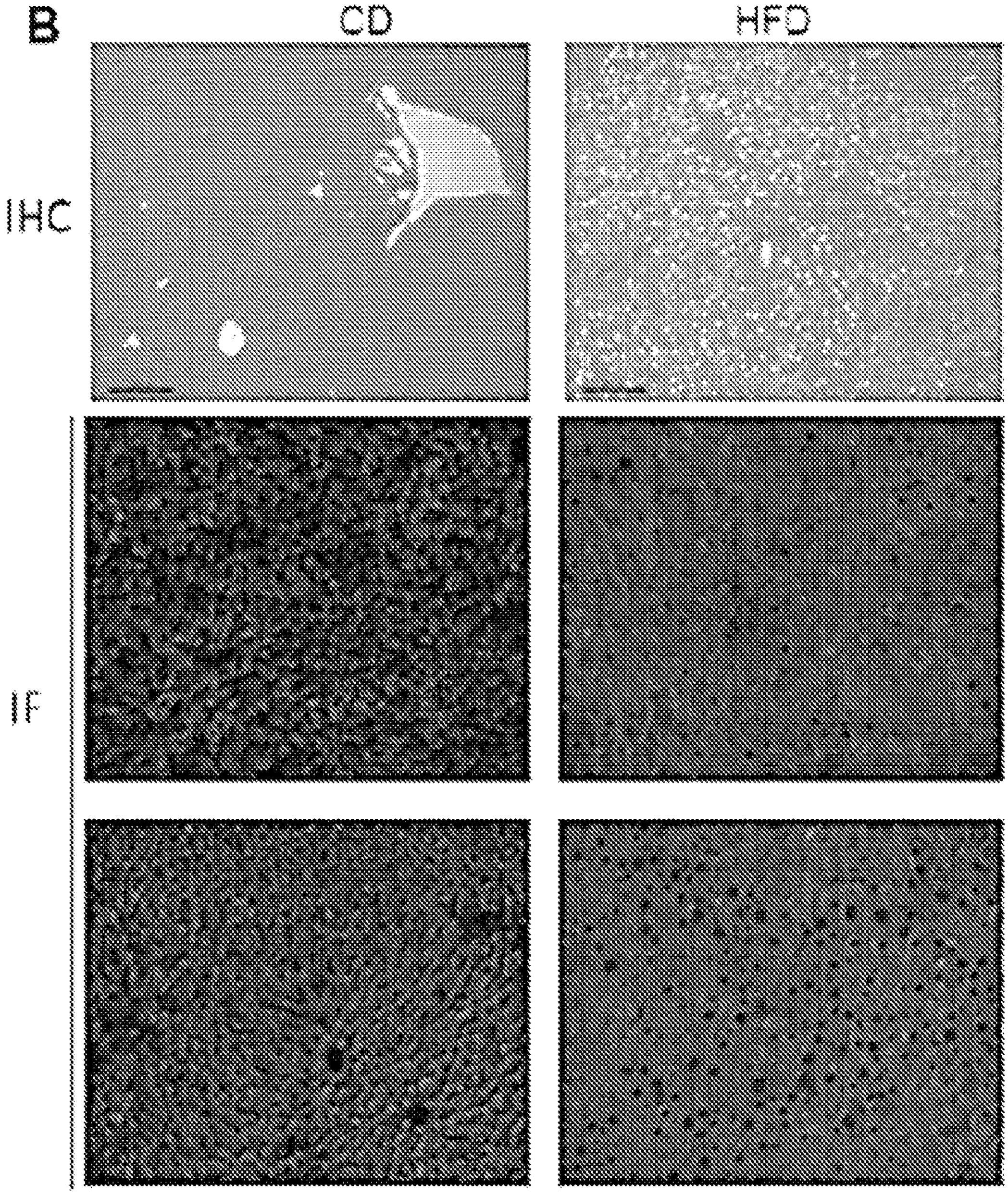

SLC25A1 expression is high in human NASH livers and its inhibition reduces obesity and hepatomegalia in HFD-fed mice. The abundance of SLC25A1 protein in different tissues was determined. Immunoblot experiments performed on adult normal mice revealed that SLC25A1 is primarily expressed in the visceral abdominal fat (WAT) and in the liver, suggesting a role for this protein in central metabolism and energy storage, while it is present to a lesser extent in the adult brain, pancreas, kidney, lung and colon (FIG. 1A). Immunohistochemical (IHC) analysis of tissue microarrays derived from human livers of patients with NASH showed high Slc25a1 expression levels (FIG. 1B, top panels; quantified in FIG. 1C). Similarly, in mice fed with a high fat diet enriched in lard and sucrose (HFD), Slc25a1 expression was increased in the liver relative to control mice (FIG. 1B, bottom panels; quantified in FIG. 1D; and FIG. 8). Finally, Slc25a1 was identified among genes associated with NAFLD in the comparative toxicogenomic database, suggesting a role for this protein in this disease (https://amp.pharm.mssm.edu/Harmonizome/gene_set/Non-alcoholic+Fatty+Liver+Disease/CTD+Gene-Disease+Associations).

Figure 1G:
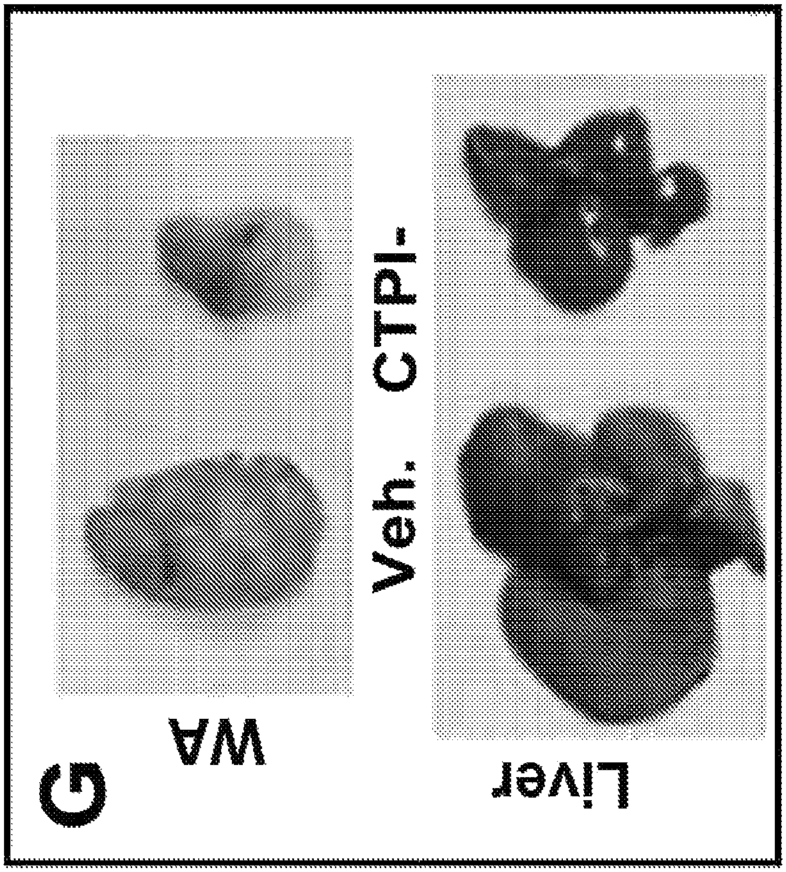
Figure 1H:
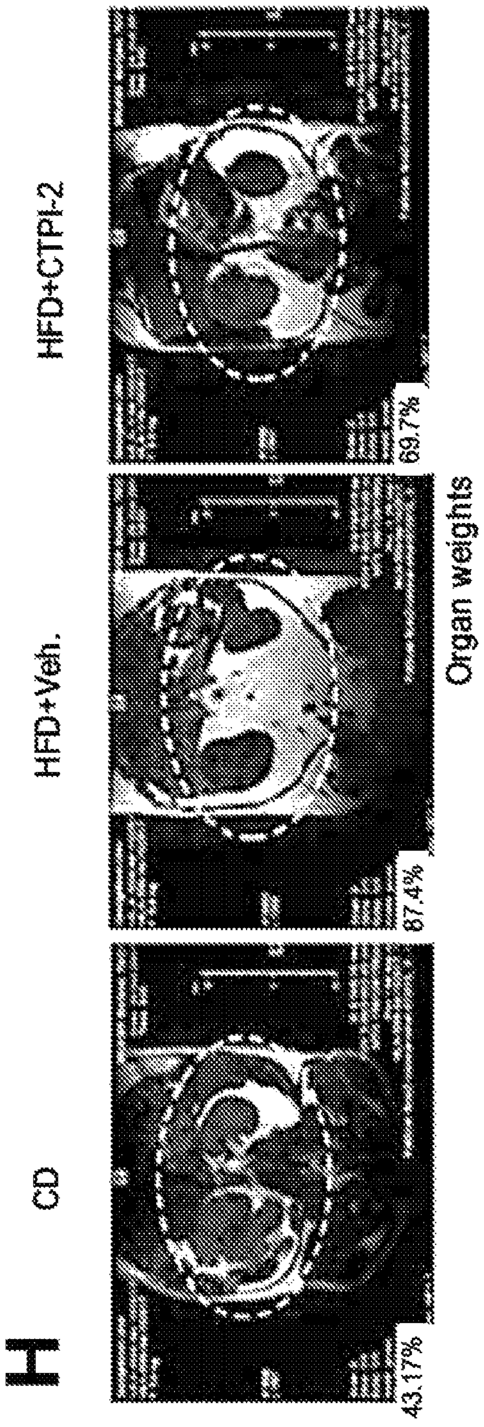
Figure 1I:
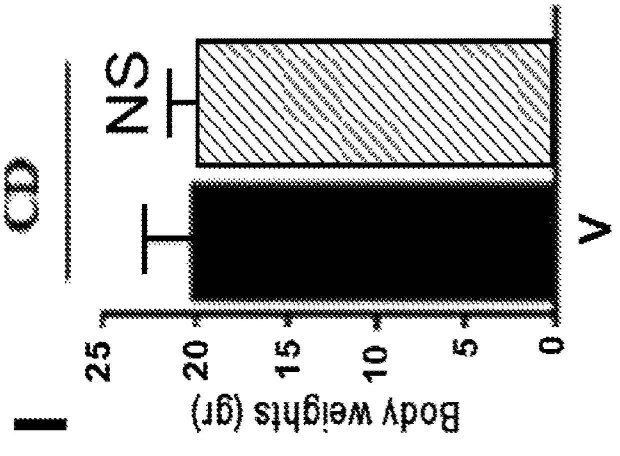
Figure 1J:
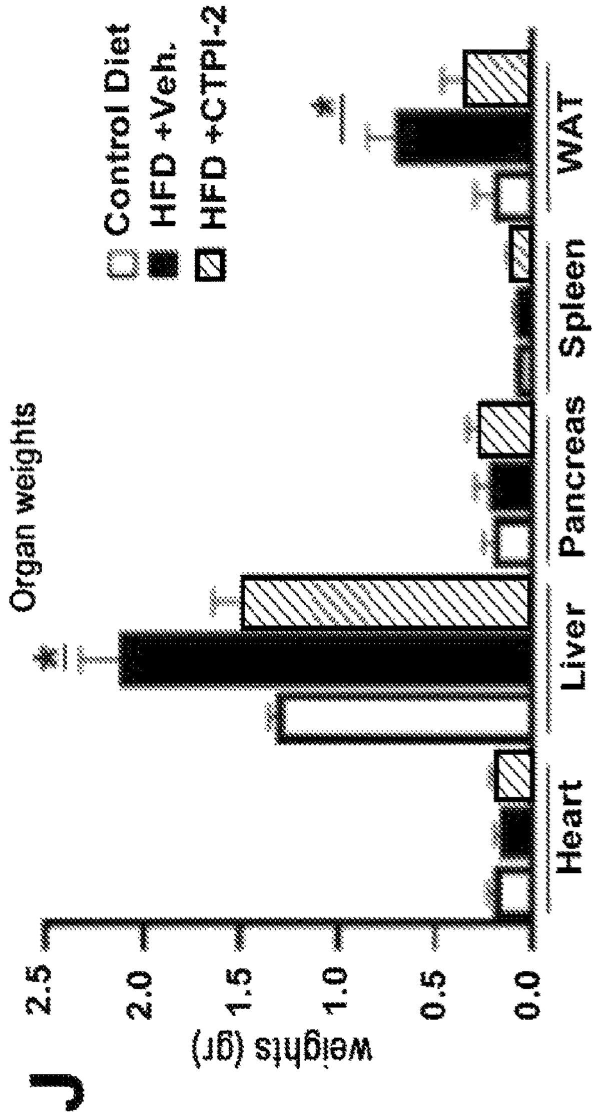

To explore the role of Slc25a1 in NASH, the well-established model of Diet-Induced-Obesity (DIO), of C57Bl/6J mice fed with the HFD for 6 months, was used. C57BL/6J mice were randomized to receive control diet (CD) or the HFD with or without the Slc25a1 inhibitor CTPI-2 (Fernandez et al. "The mitochondrial citrate carrier, SLC25A1, drives stemness and therapy resistance in non-small cell lung cancer," *Cell Death Differ.* 25(7):1239-1258 (2018)), administered at 50 mg/kg of CTPI-2, on alternate days. To eliminate potential differences in feeding behavior, animals were kept at one or two mice per cage and the daily food consumption was measured at regular intervals. It was found that CTPI-2 did not modify feeding behavior and thus, did not induce a caloric restricted state (not shown). As expected, HFD-fed mice exhibited a dramatic increase in body weight over time and treatment with CTPI-2 largely prevented such weight gain particularly reducing the WAT, as also revealed by Magnetic Resonance Imaging, MRI (FIG. 1E-H). Importantly, CTPI-2 did not modify body weights in mice fed with a normal diet (FIG. 1I). Upon visual examination, the liver of HFD-fed mice were pale and significantly enlarged, consistent with steatosis and CTPI-2 completely reverted this phenotype (FIG. 1G). Further, measurement of the weight of all organs revealed that CTPI-2 had specific effects in the liver and in the WAT (FIG. 1J), reducing their mass, again in agreement with prevalent activities of this protein in these organs.

Figure 2A:
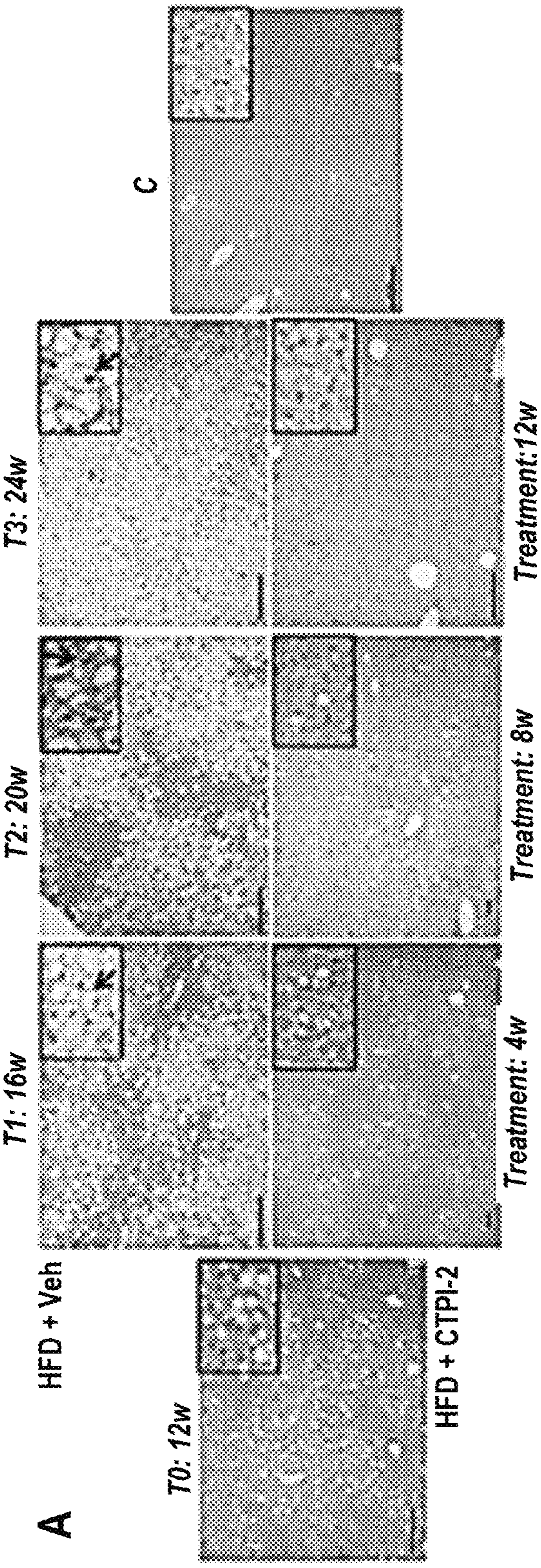
FIGS. 2A-H show that Slc25a1 inhibition with CTPI-2 ameliorates steatosis and liver injury.
Figure 2C:
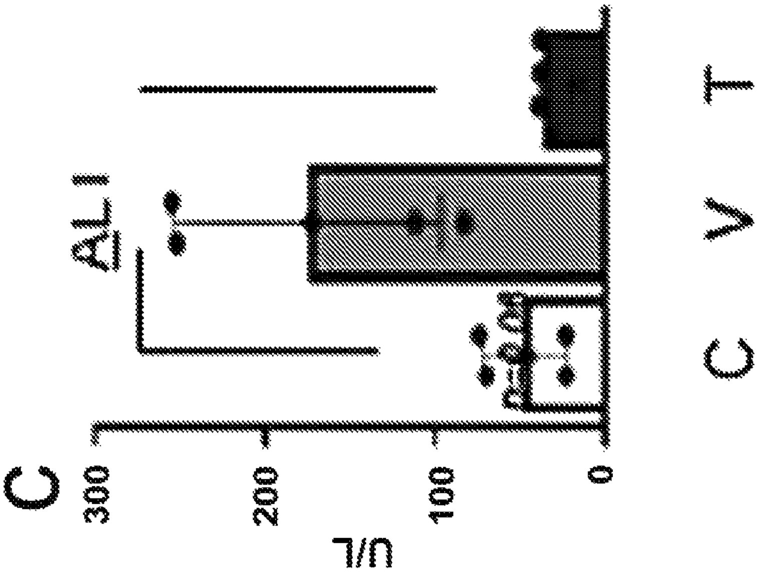
Figure 2B:
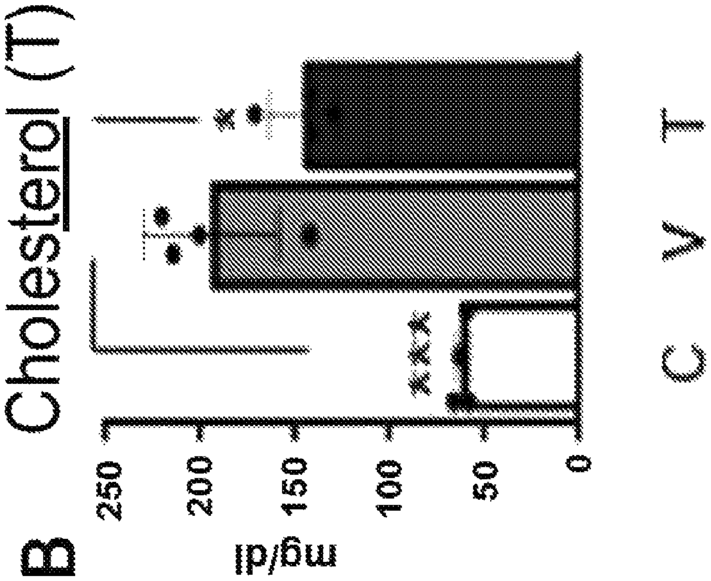
Figure 2D:
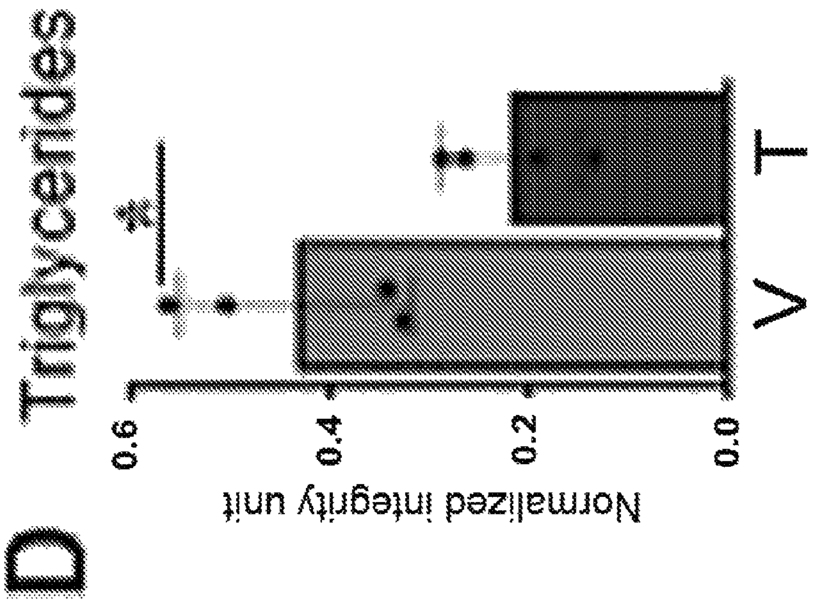
Figure 2E:
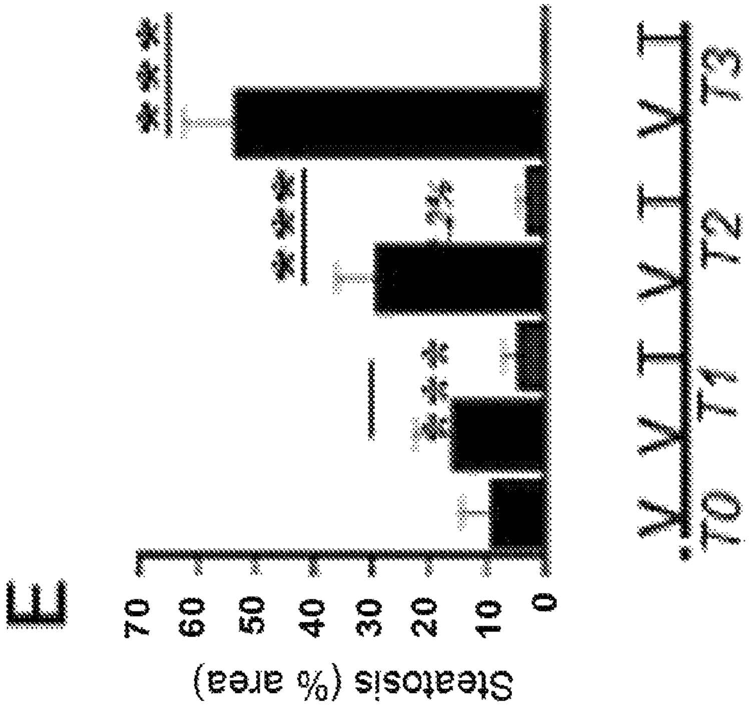
Figure 2F:
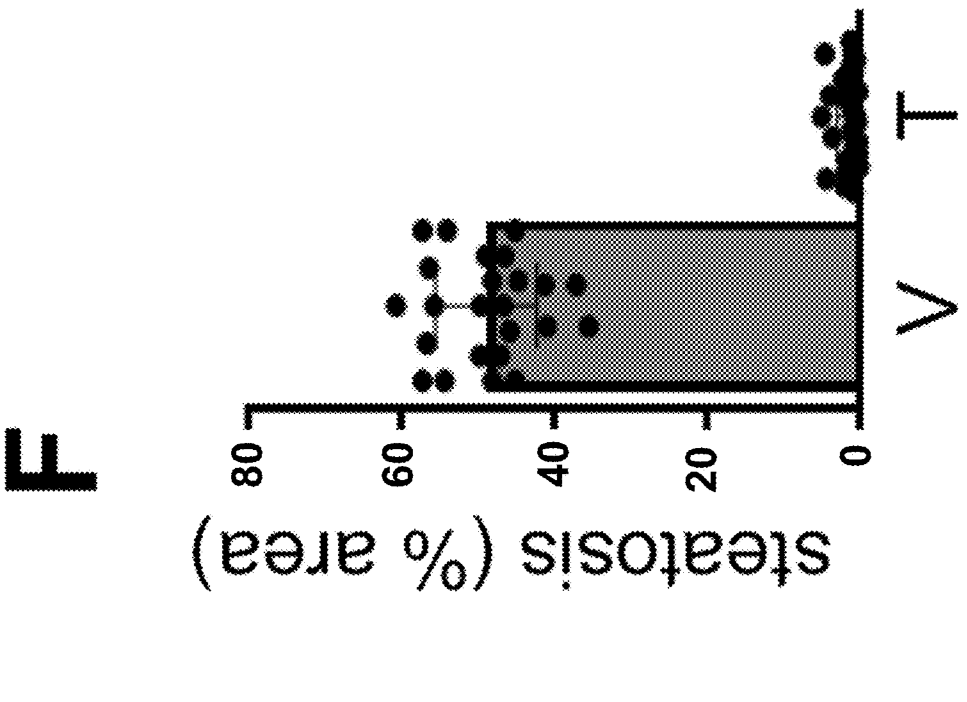
Figure 2G:
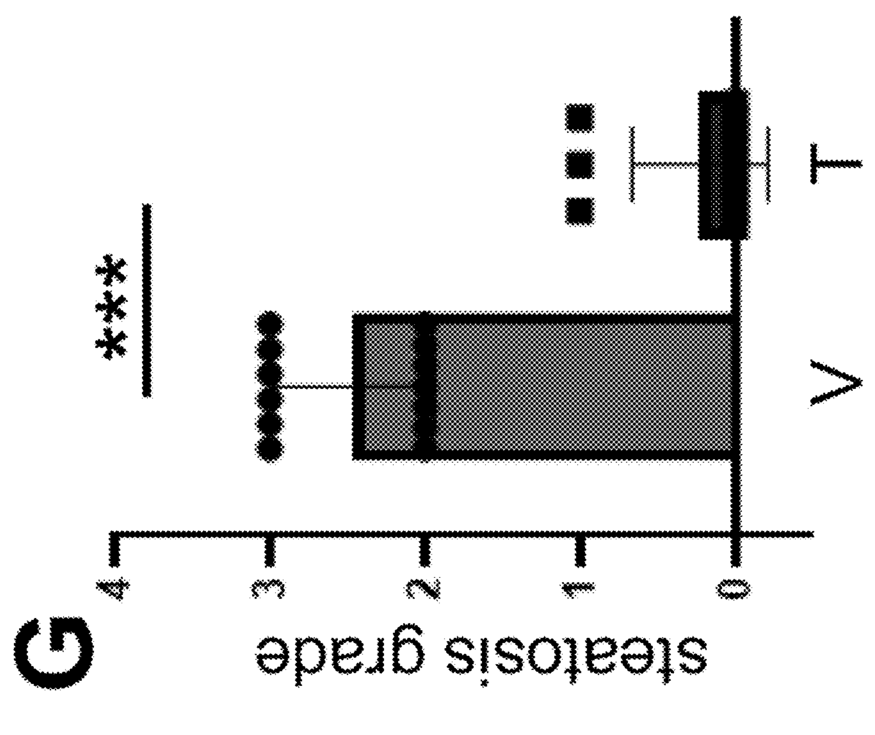
Figure 2H:
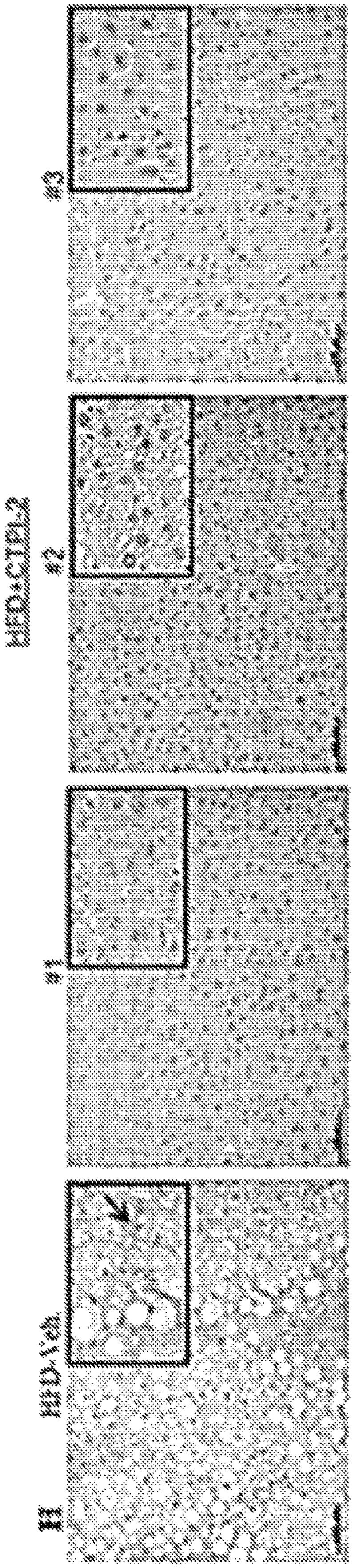

SLC25A1 is induced by a HFD and by hyperglycemia and CTPI-2 prevents steatohepatitis and normalizes glucose tolerance. The hallmark of NASH is the progressive inflammation in part triggered by lipotoxicity that leads to liver injury, inflammation, and eventually to liver fibrosis. The effects of CTPI-2 on the liver of HFD-fed mice were studied. Given that the majority of patients seek medical attention when steatosis has already occurred, it was sought to determine at what stage of liver disease evolution CTPI-2 can be effective. To this end, time-course experiments whereby mice were initiated with a HFD regimen for 3 months before CTPI-2 administration were performed. The mice were then sacrificed after 4, 8 and 12 weeks of CTPI-2 treatment, corresponding to 16, 20 or 24 weeks of HFD regimen. In mice fed with the HFD, the liver was filled with fatty deposits, in the form of micro- and macrovesicular steatosis, and the hepatocytes exhibited typical ballooning degeneration, indicating the presence of steatohepatitis (FIG. 2A). Accordingly, these mice displayed hypercholesterolemia and hepatic injury as demonstrated by the elevated levels of Alanine Aminotransferase (ALT) and CTPI-2 treatment normalized cholesterol, ALT and triglyceride levels (FIG. 2B-D) and nearly completely reversed liver steatosis (FIG. 2A and quantified in 2F-G). After 3 months of exposure to the HFD, at which time CTPI-2 treatment started, steatosis was already evident and progressed over time. CTPI-2 reverted these early stages of steatosis and also prevented the evolution to steatohepatitis. This was identified in these HFD-fed mice based upon the dramatic increase of lipid accumulation, the presence of hepatocyte ballooning (FIG. 2A), the elevated levels of ALT (FIG. 2C) and the presence of perivascular inflammatory infiltration. Although some extent of heterogeneity in the response of individual mice to CTPI-2 (depicted in FIG. 2H) was observed, after 3 months of CTPI-2 administration and 6 months on the HFD, the livers of most of CTPI-2 treated mice were nearly indistinguishable from those of animals fed a normal diet.

Figure 3A:
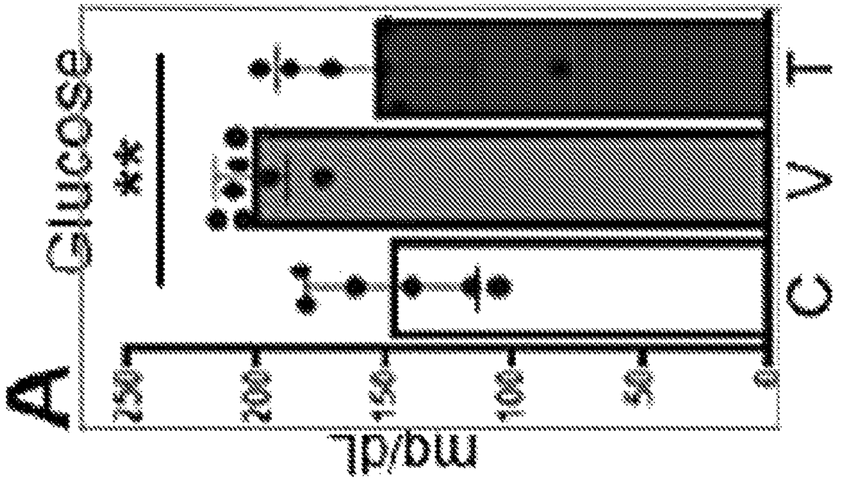
FIGS. 3A-G show that CTPI-2 normalizes glucose tolerance and insulin sensitivity.
Figure 3B:
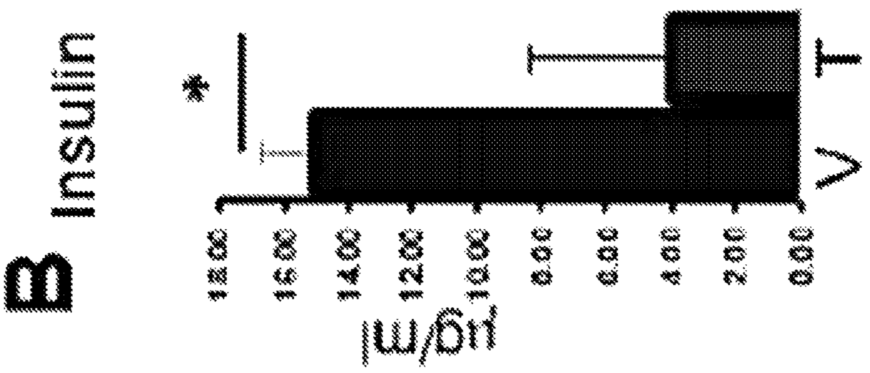
Figure 3C:
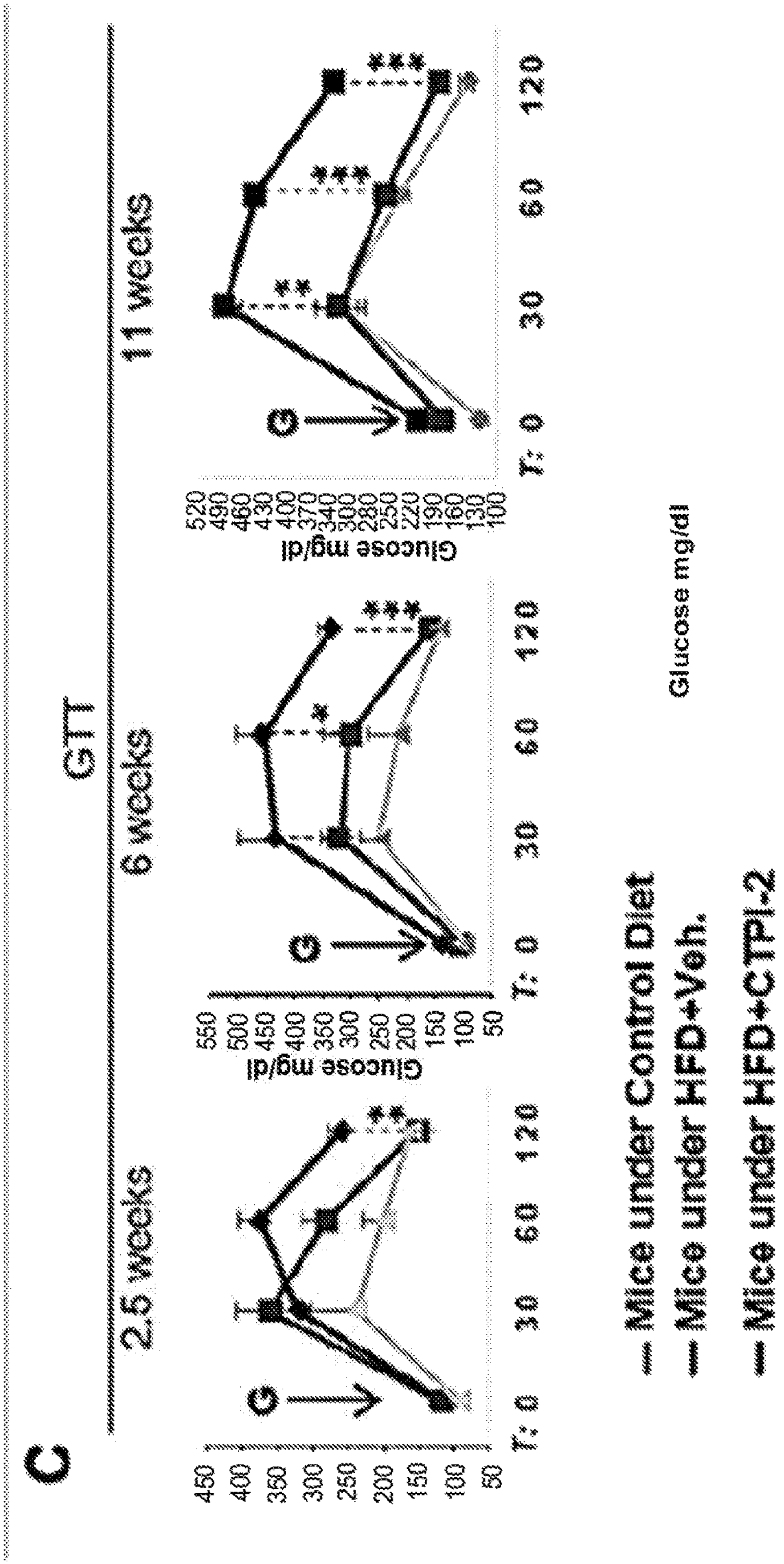
Figure 3D:
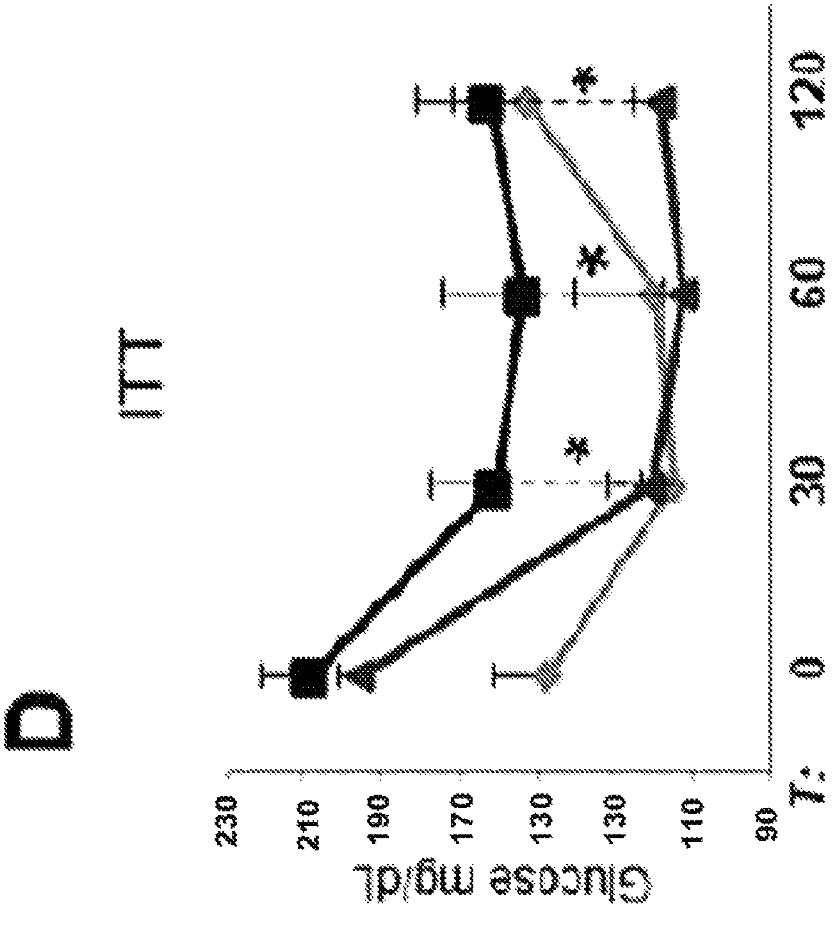

Consistent with the insulin resistance and glucose intolerance state of NAFLD/NASH, HFD-fed mice displayed high levels of fasting glucose and circulating insulin, significantly reduced clearance of blood glucose measured with glucose tolerance test (GTT), and were insulin resistant relative to control mice, as revealed by an insulin tolerance test (ITT) (FIG. 3A-D). With prolonged exposure to the HFD, control mice became increasingly unable to clear blood glucose, as documented by the enhanced area under the curve and the spiked levels of glycemia after glucose administration. CTPI-2 reduced the basal fasting glucose levels (FIG. 3A) and induced a complete time-dependent normalization of the GTT and ITT, such that after 11 weeks of treatment the glucose clearance capability of HFD-fed mice was also nearly indistinguishable from that of normally fed mice (FIG. 3CD).

Figure 3E:
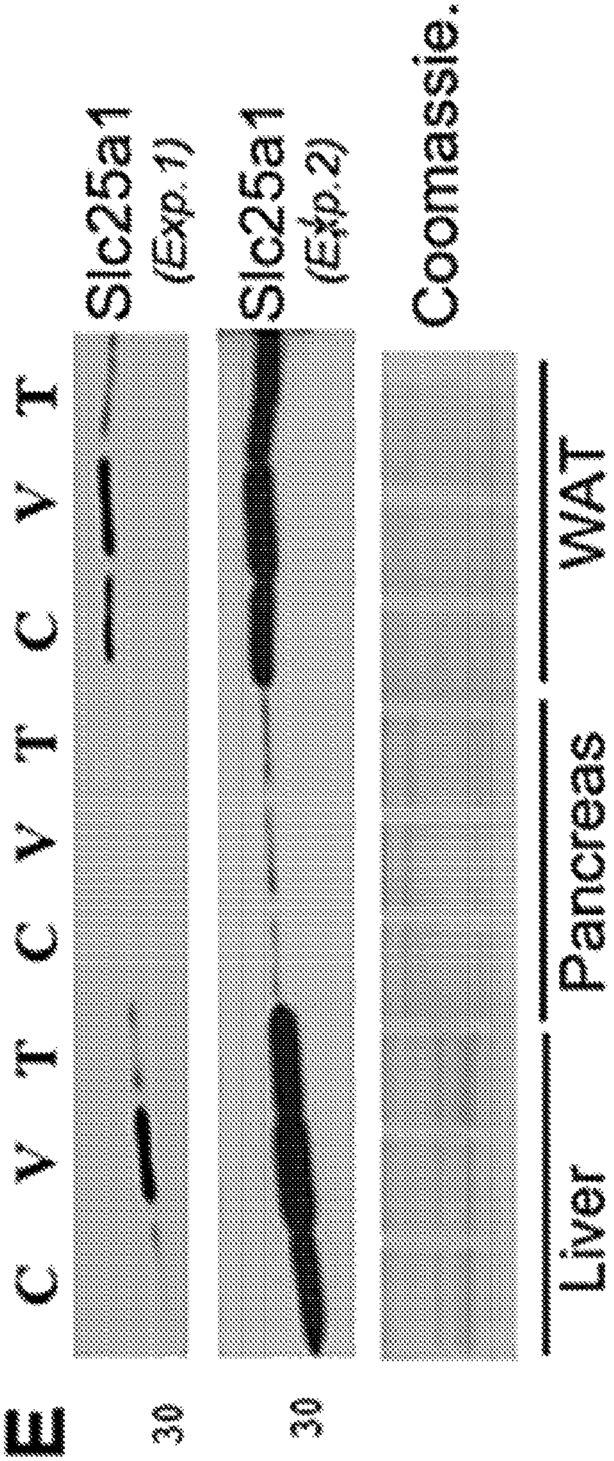
Figure 3F:
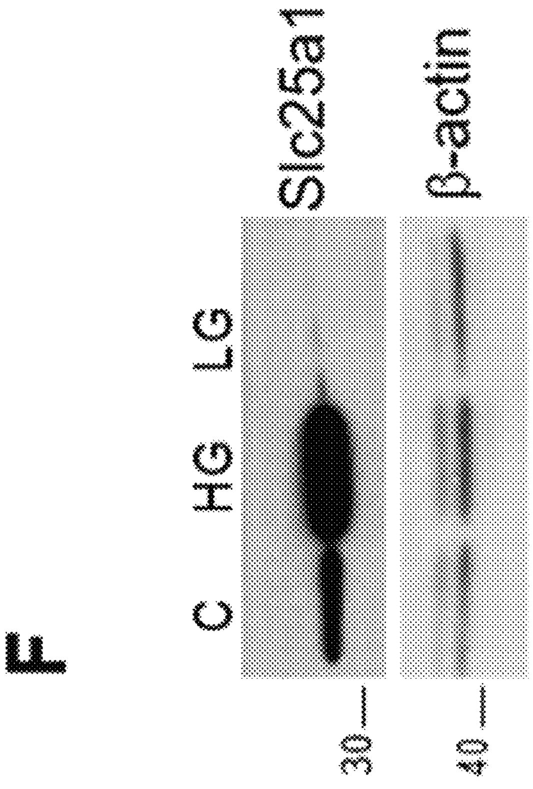
Figure 3G:
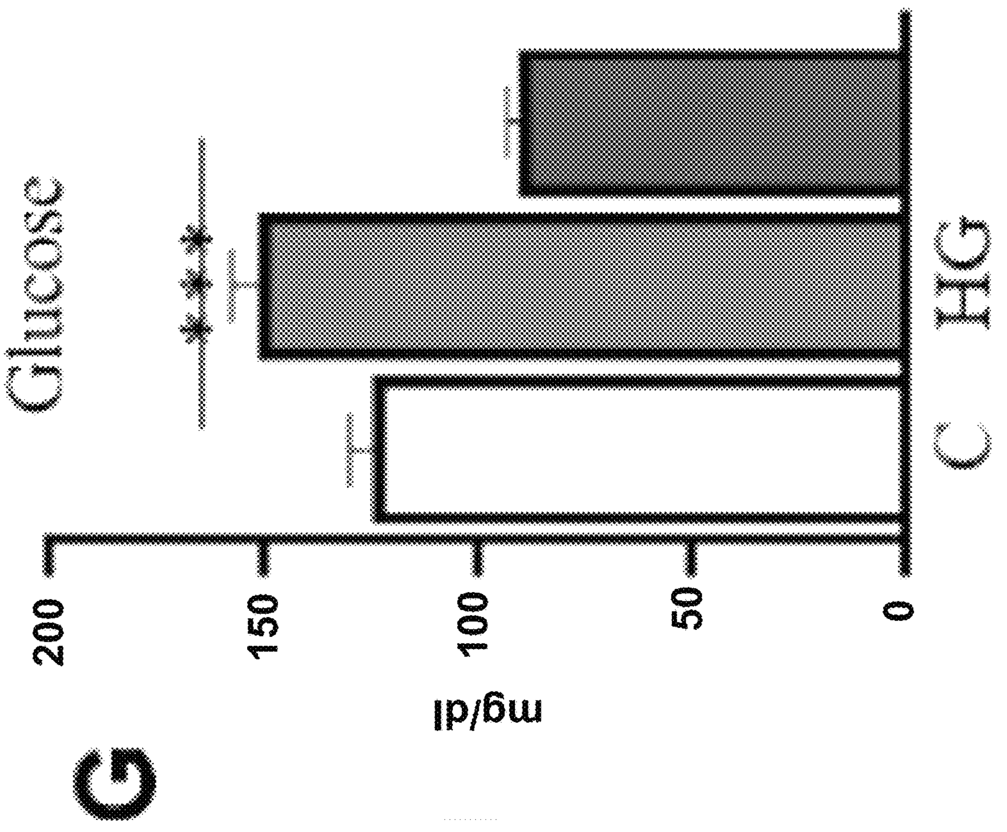

The analysis of cell extracts derived from the liver and adipose tissues demonstrated that the HFD induced an increase in SLC25A1 protein levels and, CTPI-2 reduced SLC25A1 expression levels in the adipose tissue, in the liver, but not in the pancreas (FIG. 3E). The finding that CTPI-2 can inhibit SLC25A1 expression was in contrast with previous studies performed in vitro, where CTPI-2 did not affect the expression levels of this protein, but interfered with the mitochondrial citrate transport activity (Fernandez et al.). These results raised the possibility that systemic metabolic changes induced by this agent are responsible for this effect. Therefore, SLC25A1 expression was compared in animals fed either with a equicaloric, high glucose (HG; 70%), or with a calorie-equivalent low glucose diet (LG; 7%). The results revealed that the expression of Slc25a1 was potently induced in the HGD diet but was nearly undetectable in low glucose diet (LGD)-fed animals correlating with the lower levels of fasting glycemia (FIG. 3FG). Collectively, the data reveal that SLC25A1 expression is regulated by metabolic cues through a feed forward loop mediated by lipids and glucose. Furthermore, CTPI-2 prevents the evolution of steatosis to steatohepatitis and restores glucose homeostasis. In essence, mice treated with CTPI-2 could afford the HFD regimen for a prolonged period of time, without developing significant liver damage, obesity or disruption of glucose homeostasis.

Figure 4A:
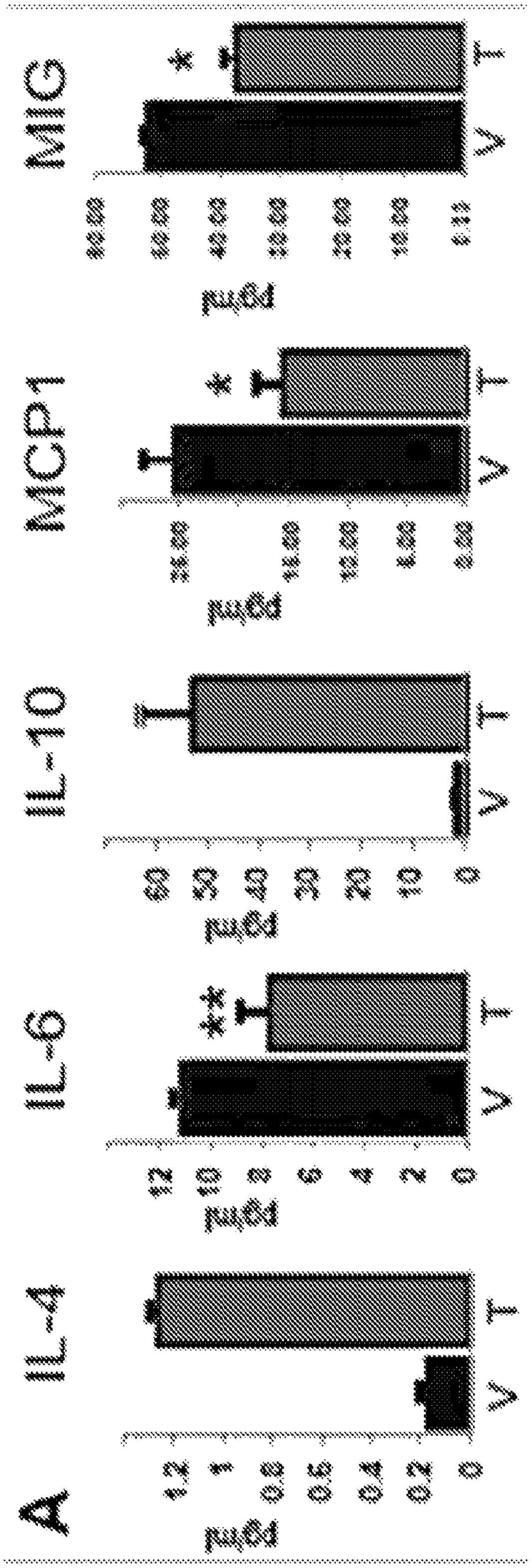
FIGS. 4A-H show that CTPI-2 influences inflammatory pathways.
Figure 4B:
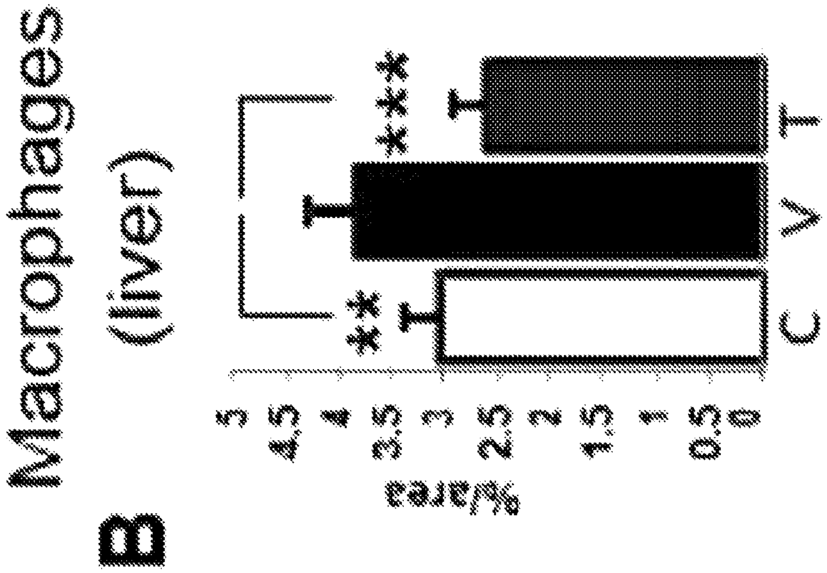
Figure 4C:
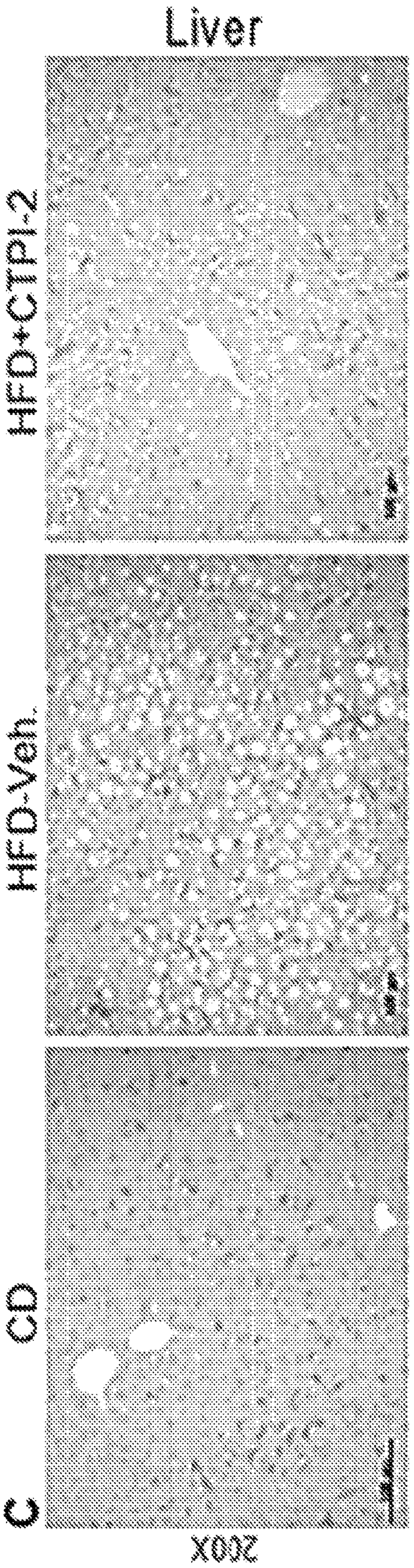
Figure 4D:
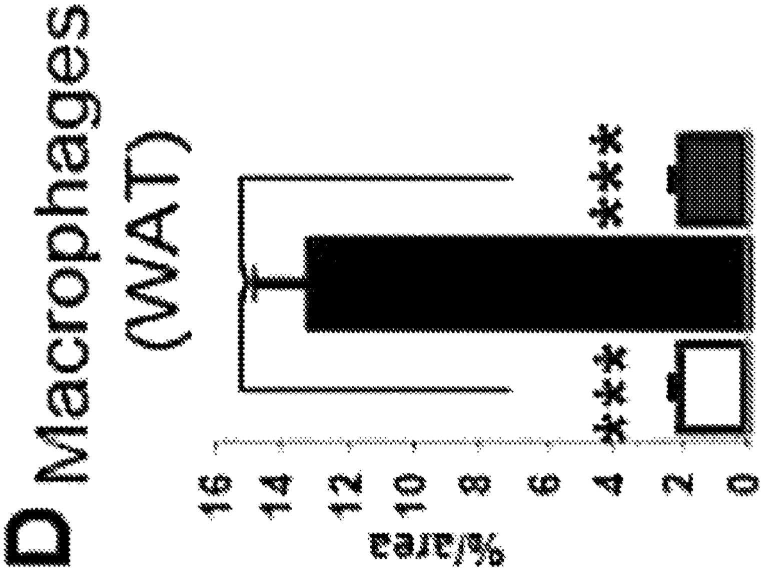
Figure 4E:
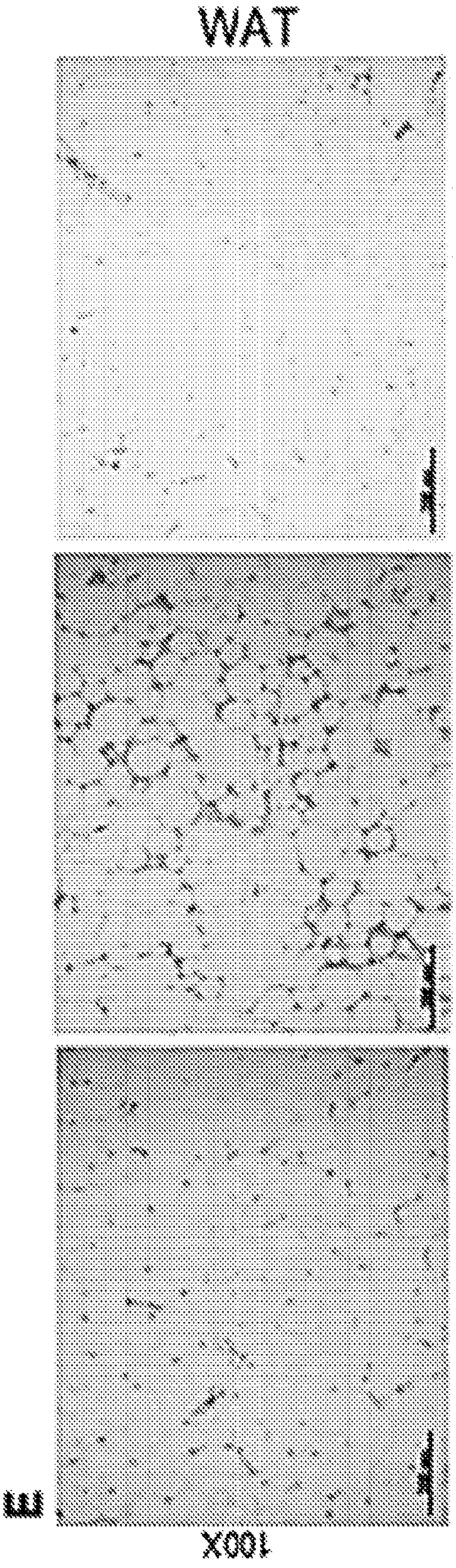
Figure 4F:
Figure 4G:
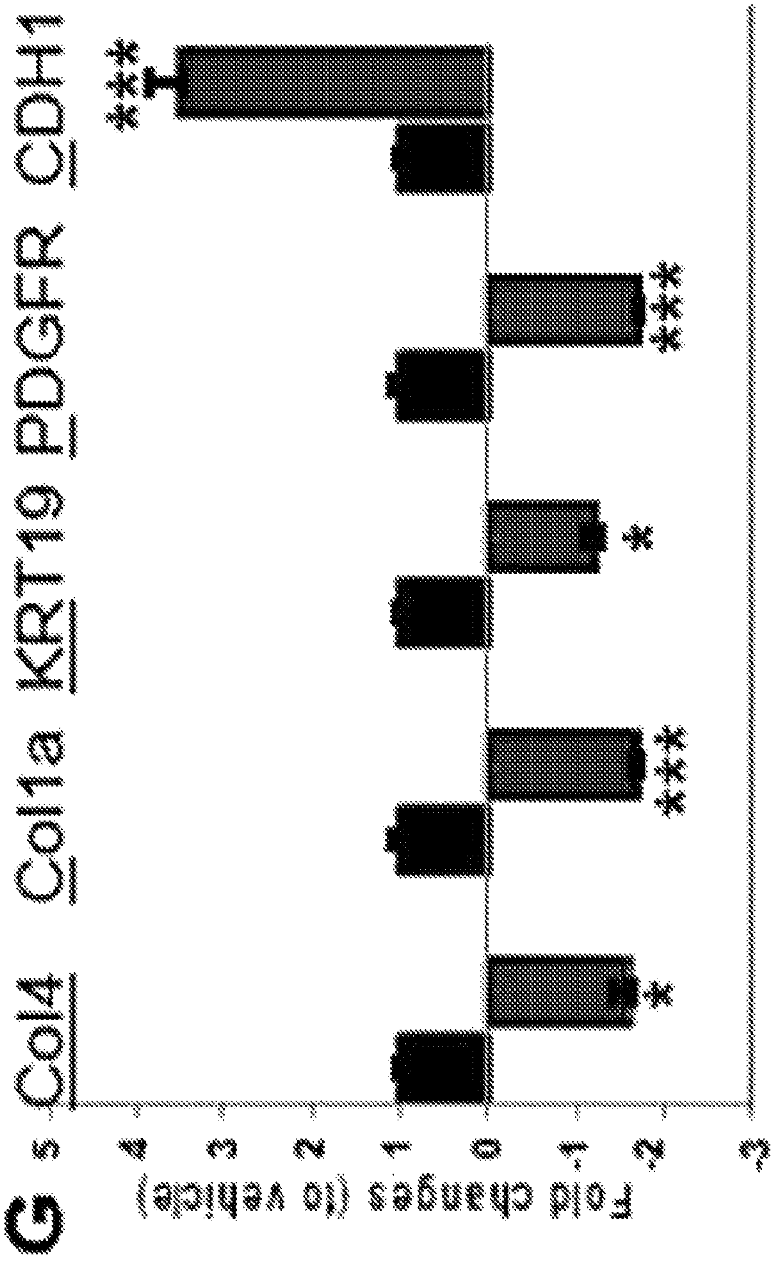
Figure 4H:
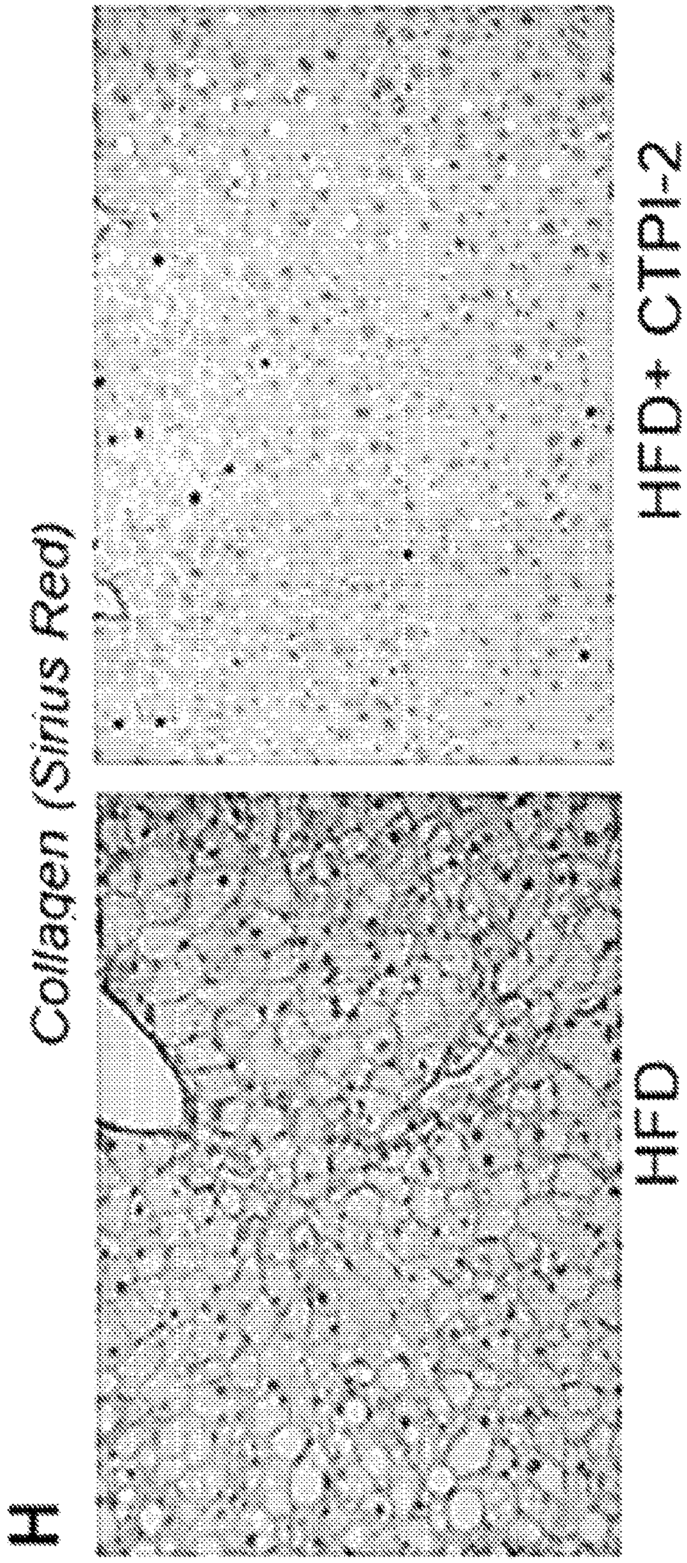

CTPI-2 blocks inflammatory signals and inhibits IL-6 and TNFα production. The hallmark of NASH is the progressive inflammation and fibrosis in part triggered by lipotoxicity and by feed-forward loops between the adipose tissue and the liver, and mediated by macrophages and IL-6. Particularly, macrophage activation induced by toxic lipids including free FAs, triglycerides and cholesterol, is a common pathogenic feature of NASH. Macrophages are functionally, though simplistically, divided in two populations, M1 and M2. The polarization of macrophages towards the M1 phenotype contributes to chronic inflammation in the liver by promoting the secretion of IL-6, TNF-α and other inflammatory mediators, while M2 macrophages promote the resolution of inflammation and tissue remodeling. Whether CTPI-2 influences inflammation was examined. CTPI-2 lowered the levels of circulating serum pro-inflammatory IL-6, while increasing anti-inflammatory IL-4 and IL-10. CTPI-2 also reduced monocyte chemo-attractant protein-1 (MCP1) and monokine induced by interferon-γ (MIG), both of which attract neutrophils and monocytes (FIG. 4A). Immunohistochemistry of the liver showed an increase in the Kupffer cells (KC) macrophage population, identified with the F4/80 antibody in HFD-fed mice as well as of macrophage infiltration in the perivascular regions (FIG. 4B-C), that was reversed by CTPI-2. Further, KC lost their spindle-like morphology. KC were also aggregated and organized in crown-like-structures (CLS) that surround hepatocytes and are known to favor macrophage proliferation and polarization (FIG. 4C). The adipose tissue of HFD-fed animals also displayed a massive infiltration of macrophages organized in multiple CLSs, and CTPI-2 completely resolved this phenotype (FIG. 4D-E). Consistent with these effects and with the lower circulating levels of inflammatory molecules, RT-PCR analysis demonstrated that CTPI-2 treatment repressed pro-inflammatory markers of the M1 phenotype, while either not affecting or increasing M2 markers (Macrophage Mannose Receptor 1, MRC1; Fibronectin 1, FN-1; Arginase 1, Arg1) (FIG. 4F). This was paralleled by a reduction of the expression of the pro-fibrotic genes including collagen 1 and 4, keratin 19 and PDGFR and an increase of the anti-fibrotic cadherin 1, as well as by a reduction of collagen in the liver of HFD-fed mice (FIG. 4GH). Thus, CTPI-2 breaks the pro-inflammatory and pro-fibrotic programs, two important drivers of NASH pathology.

Figure 5A:
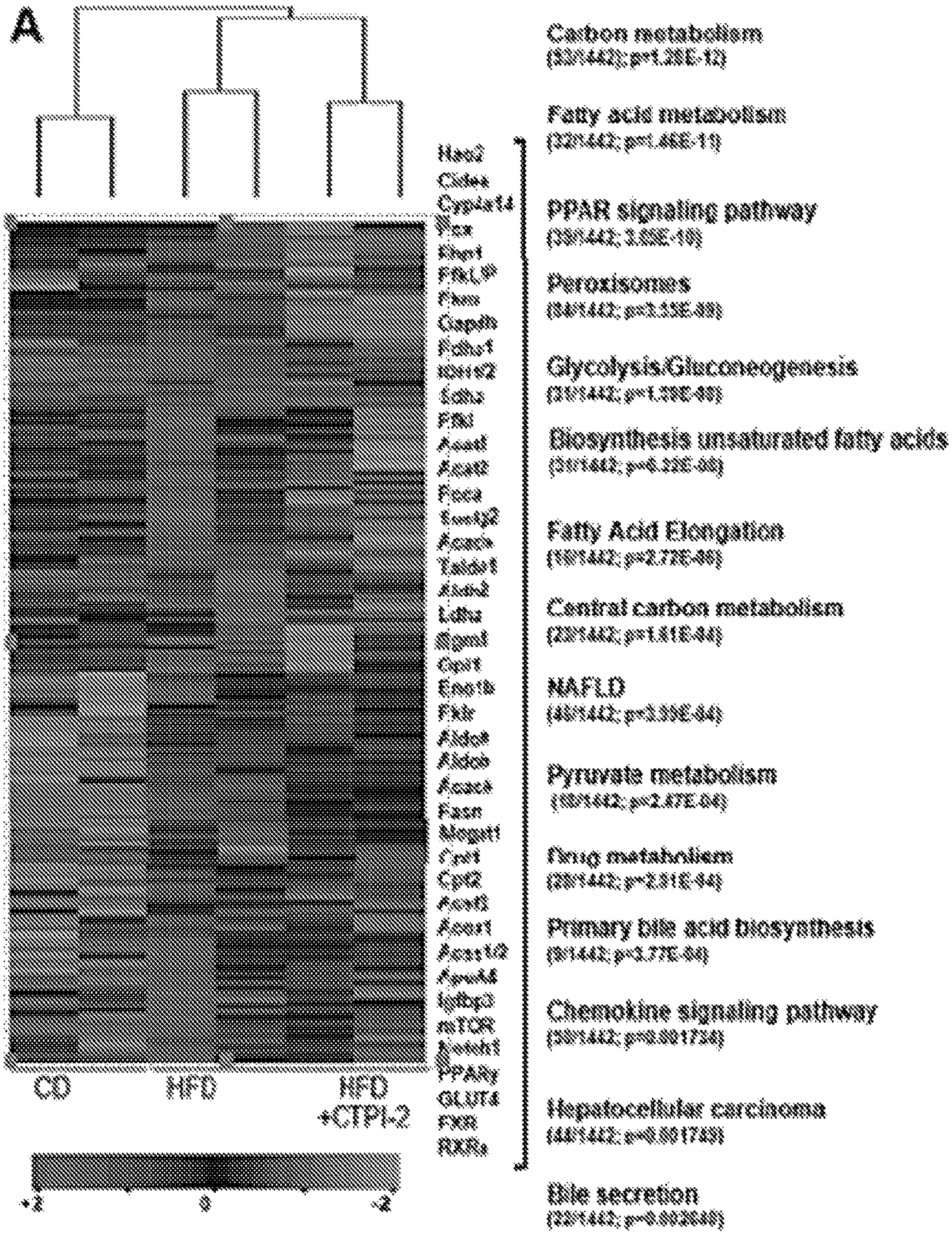
FIGS. 5A-D show molecular pathways influenced by CTPI-2.
Figure 5B:
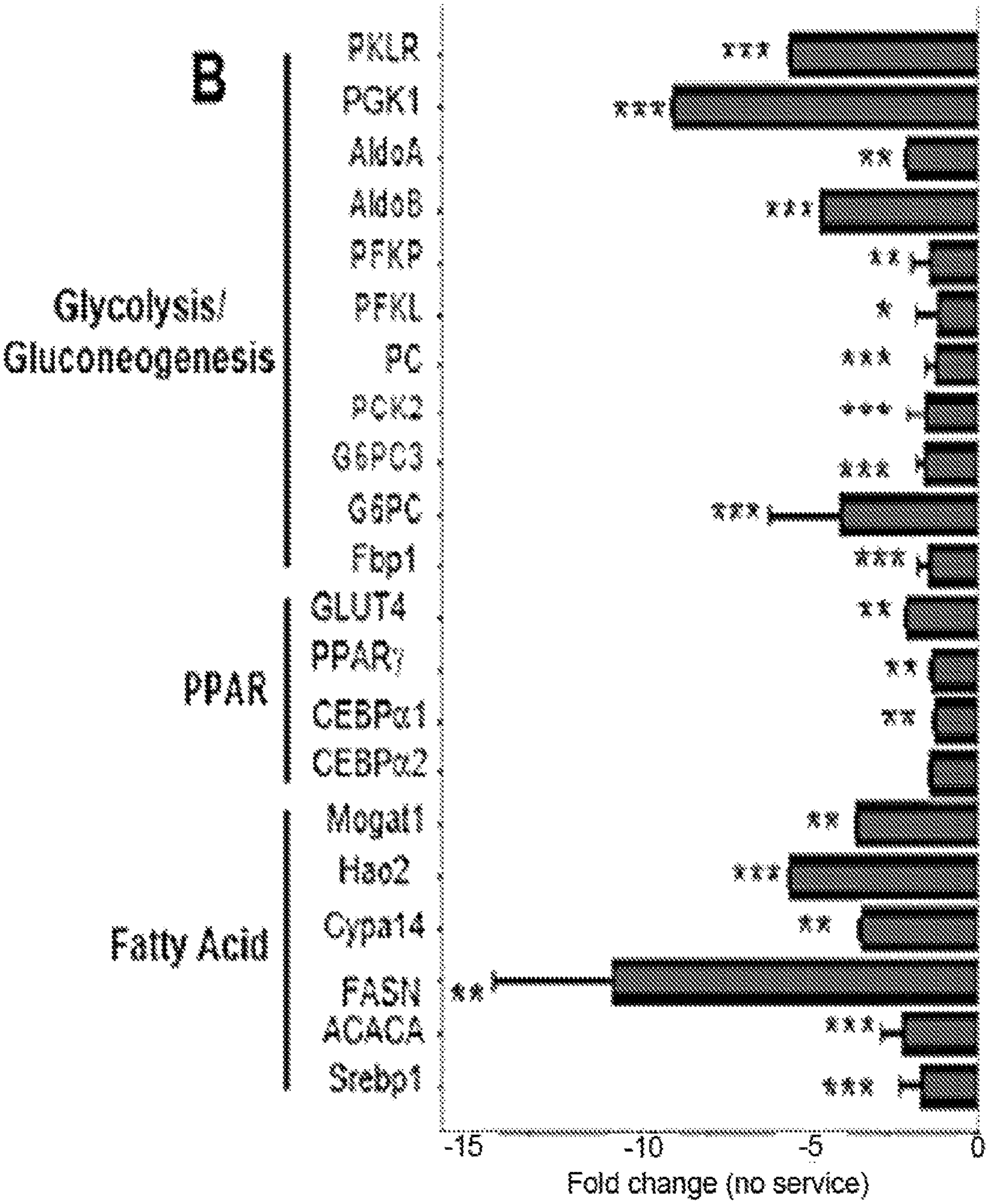
Figure 5C:
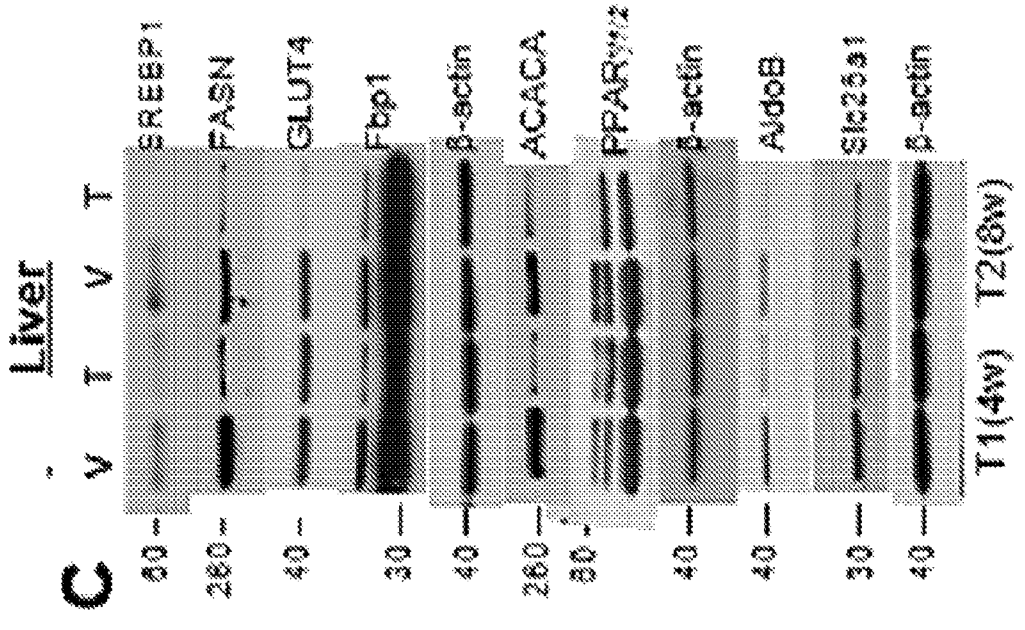
Figure 5D:
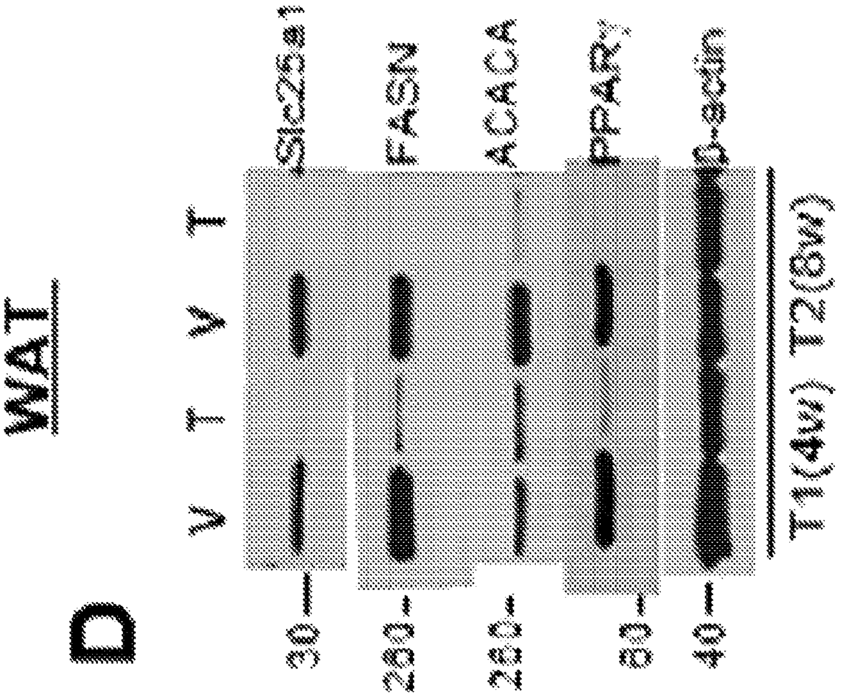

CTPI-2 regulates the citrate concentration in the liver, inhibiting the lipogenic and gluconeogenic pathway. To identify the molecular mechanisms responsible for the biological effects of CTPI-2 and to identify early events, RNA sequencing experiments (RNAseq) were performed on the livers of mice treated for 4 weeks. This approach demonstrated that the HFD induced a large category of transcripts whose expression was attenuated or down-regulated by CTPI-2, which essentially reverted the gene expression program induced by the HFD (FIG. 5A). This category included genes involved in fatty acid synthesis (FASN, ACACA), the Peroxisome Proliferator-Activated Receptors (PPAR) pathway whose members regulate glycolysis, lipid metabolism and adipogenesis, bile acid synthetic pathways, inflammatory chemokine signal pathways. It also included recently discovered drivers of NASH, particularly Hao2, a hydroxyacid oxidase, and Monoacylglycerol acyltransferase (Mogat1,) which converts monoacylglycerol to diacylglycerol. CTPI-2 also down-regulated a large cluster of genes involved in NAFLD, strengthening its potential therapeutic relevance in this disease. Quantitative reverse transcription PCR (RT-qPCR) experiments demonstrated a suppression of master lipogenetic genes, including SREBP1, FASN and ACACA (FIG. 5B). PPARγ and its downstream target genes, CEBPα1, CEBPα2 and GLUT4, were also down-regulated, while the levels of PPARα were unchanged. This gene expression pattern was concordantly paralleled by changes in the protein levels in both the liver and adipose tissue (FIG. 5CD). In addition, the RNAseq results also showed that CTPI-2 repressed genes/pathways involved in carbon and pyruvate metabolism, in glycolysis, as well as gluconeogenic genes, that together with glycogenolysis are a main contributor to the blood glucose level. These included, Fbp1, PC, phosphoenolpyruvate carboxykinase (PCK1/2), glucose 6-phosphatase alpha (G6PC) and beta (G6PC3), and Aldolase AB (AldoA/B), the two isoforms of PFK (PFKL/P), Phosphoglycerate Kinase 1 (PGK1) and Pyruvate Kinase (PKLR) (FIG. 5B).

Figure 6B:
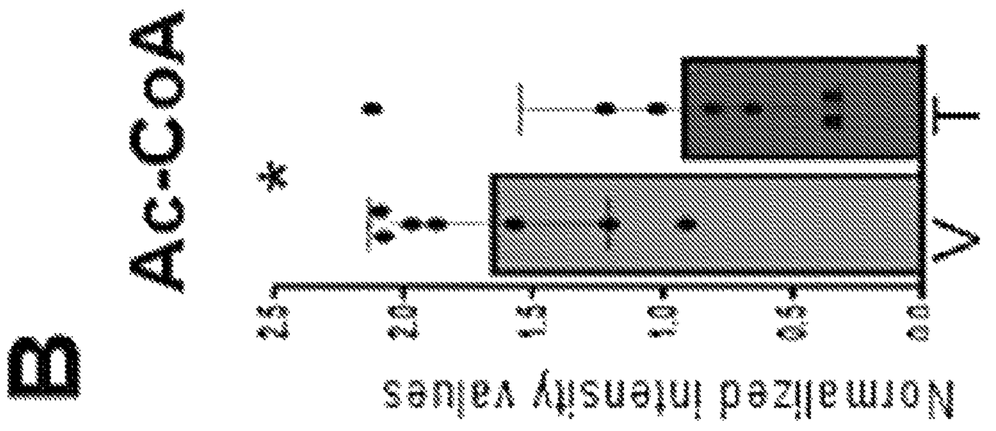
FIGS. 6A-H show that CTPI-2 regulates citrate concentration in the liver and blunts triglyceride production.
Figure 6A:
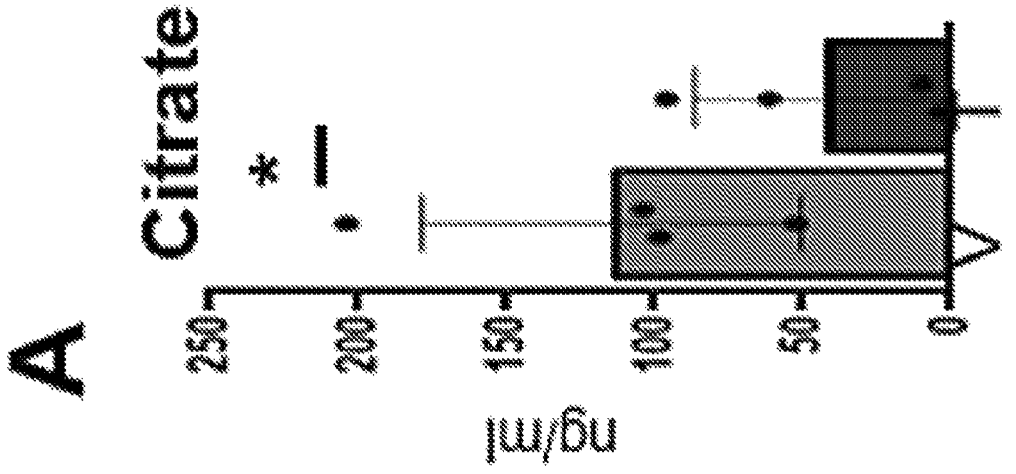
Figure 6C:
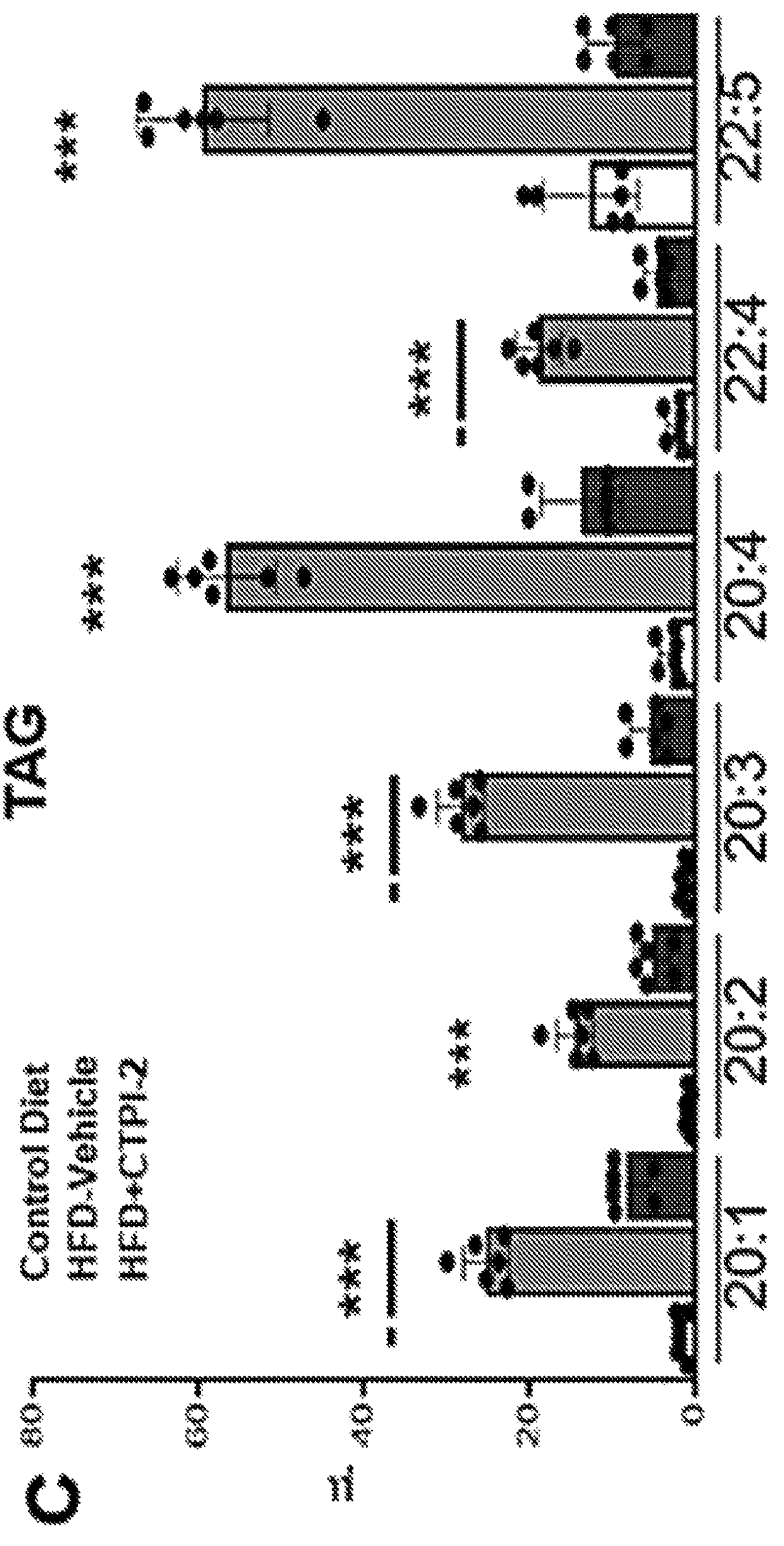
Figure 6D:
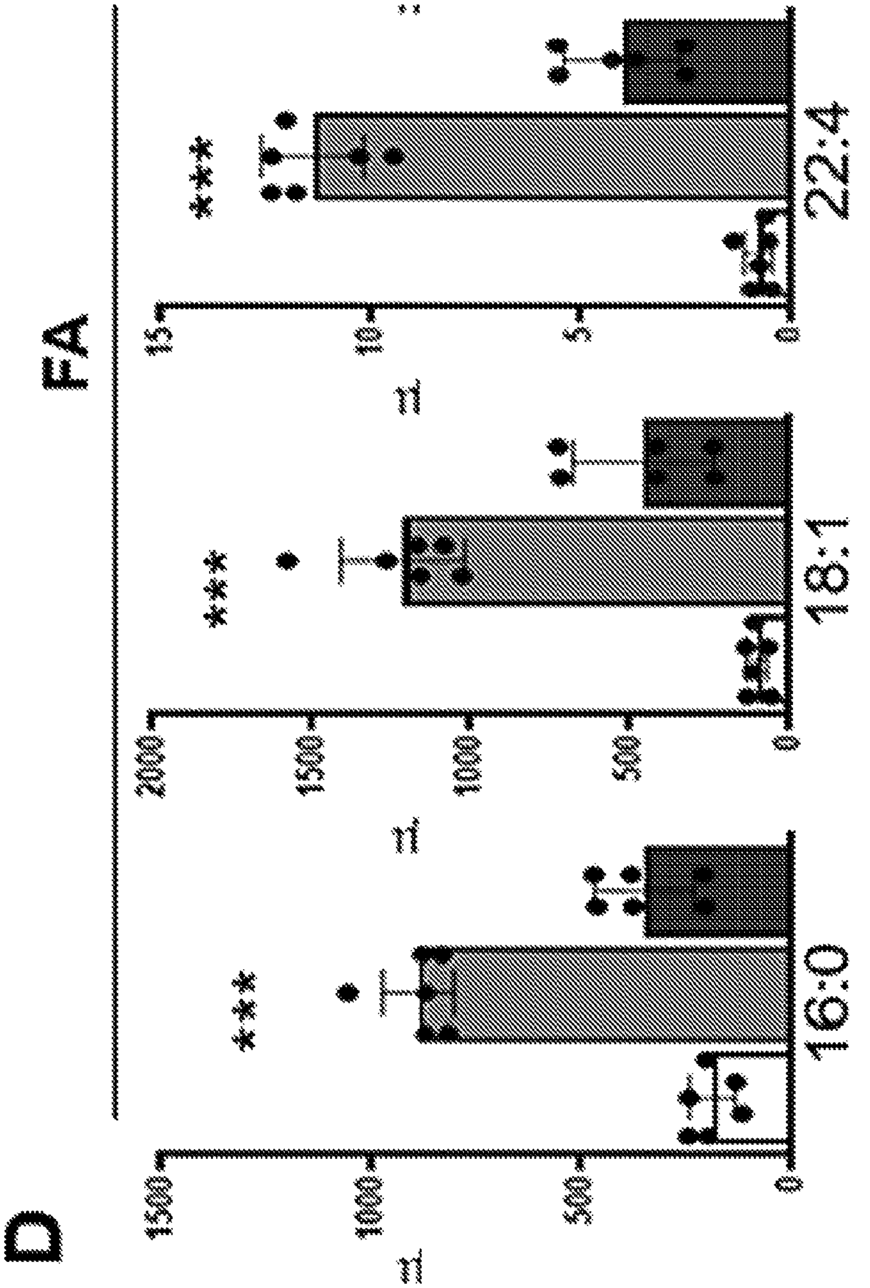
Figure 6F:
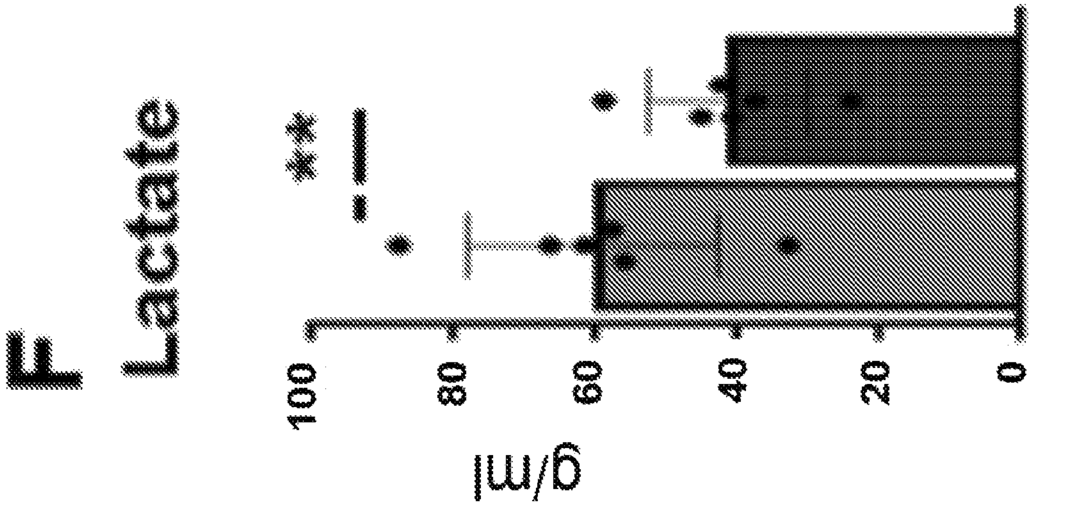
Figure 6E:
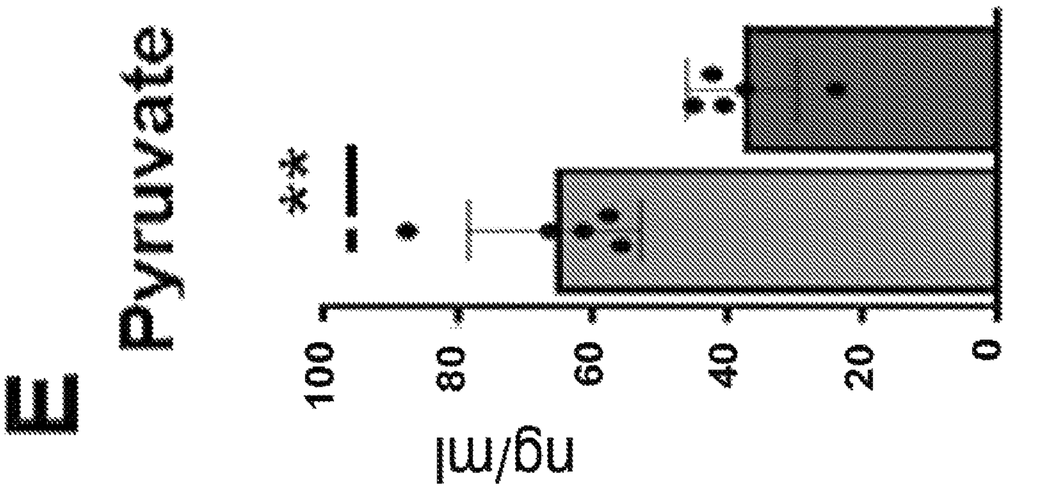
Figure 9A:
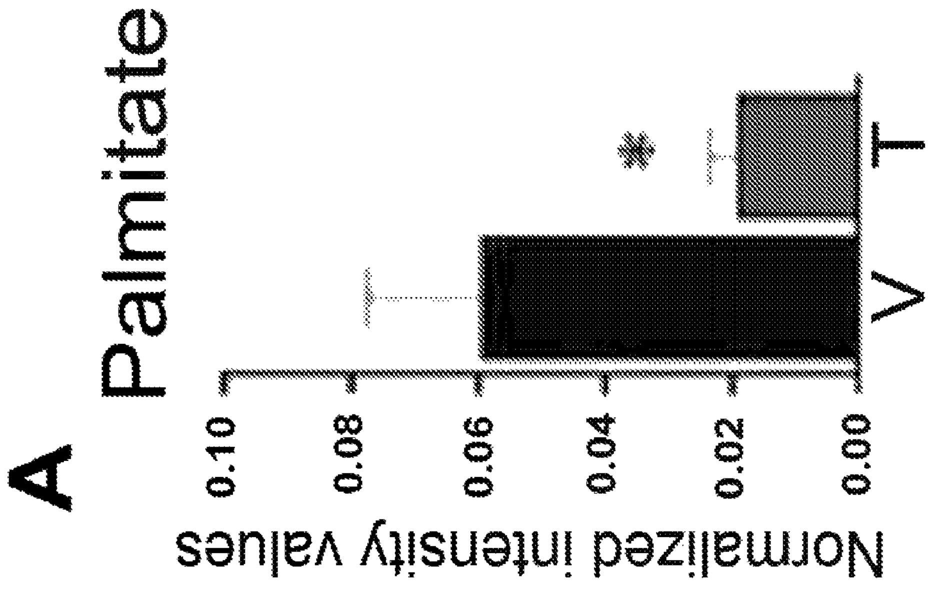
FIGS. 9A-C show alterations in the lipid profile induced by CTPI-2.
Figure 9B:
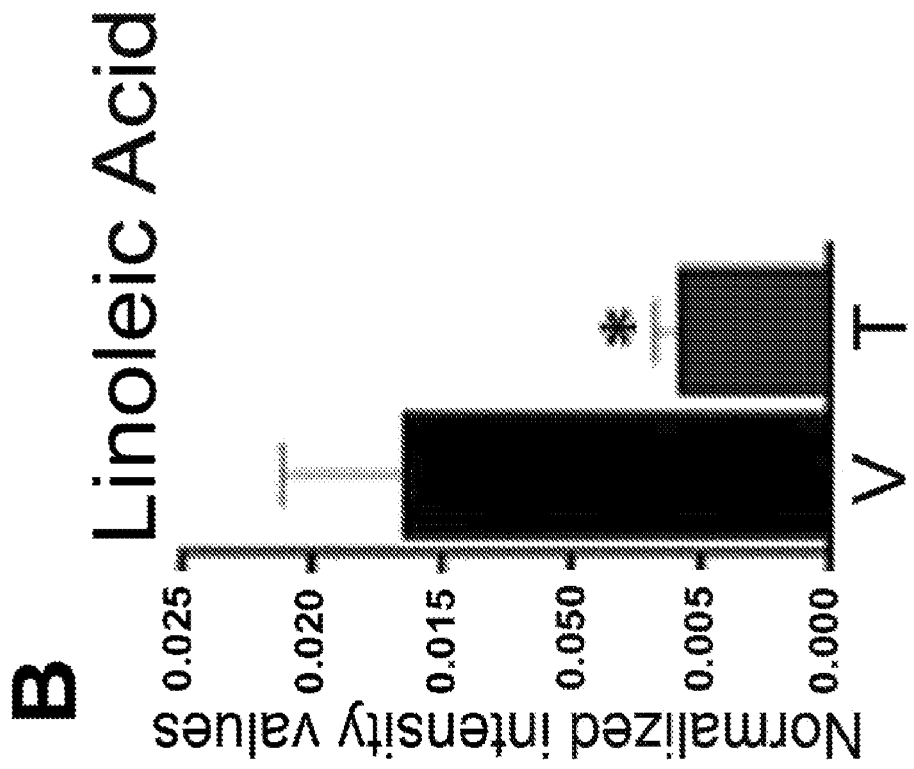
Figure 9C:
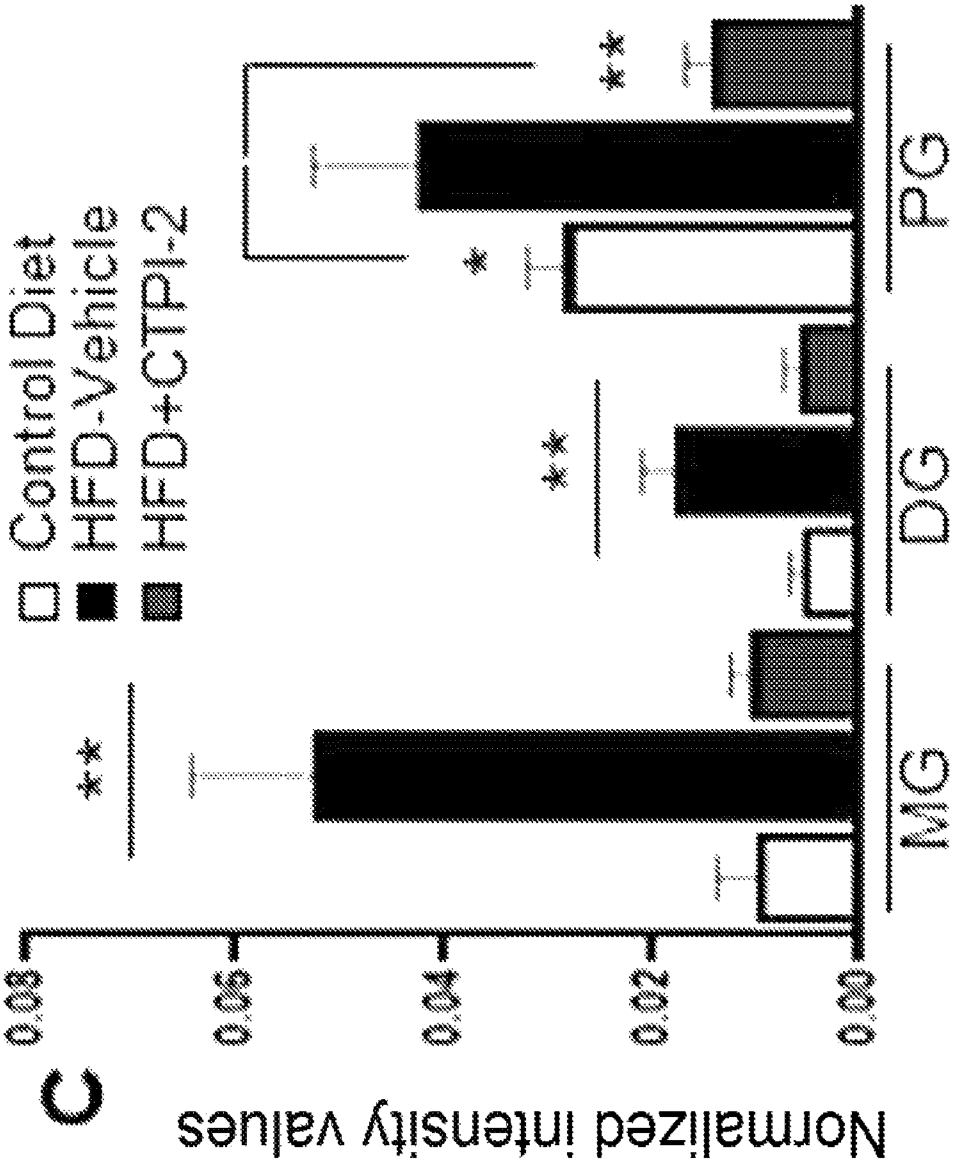

Cytoplasmic citrate provides Acetyl-CoA (Ac-CoA) that is utilized in the first steps of FA synthesis. Given the role of SLC25A1 in citrate transport, it was hypothesized that inactivation of SLC25A1 would blunt the availability of citrate and Ac-CoA for lipid synthesis, thus leading to suppression of the lipogenic program seen with the RNAseq experiments. Consistent with this idea, the citrate and Ac-CoA concentrations were significantly lower in the liver of CTPI-2 treated mice (FIG. 6A-B). Furthermore, the analysis of the lipid profile demonstrated that CTPI-2 reduced the levels of the lipid precursors palmitic acid and linoleic acid, of monoglycerides, of diglycerides and of phosphatidylglycerol (FIG. 9A-C). The liver concentration of long chain triglycerides, as well as the total level of free fatty acids, particularly those with chain bonds from 16 to 25, containing palmitic-(16:0), stearic-(18:0), arachidonic (20:1) and eicosapentaenoic acid (22:5), were also significantly diminished by CTPI-2 (FIG. 6C-D). These results are consistent with a deficit very upstream in the lipogenic pathway induced by CTPI-2 and confirm the important role of Slc25a1 in lipid metabolism in vivo. In addition, the liver concentration of pyruvate and lactate, both products of glycolysis and precursors of gluconeogenesis, were decreased, signaling the decreased gluconeogenesis and glycolysis in the liver of CTPI-2 treated mice (FIG. 6 E-F).

Figure 6G:
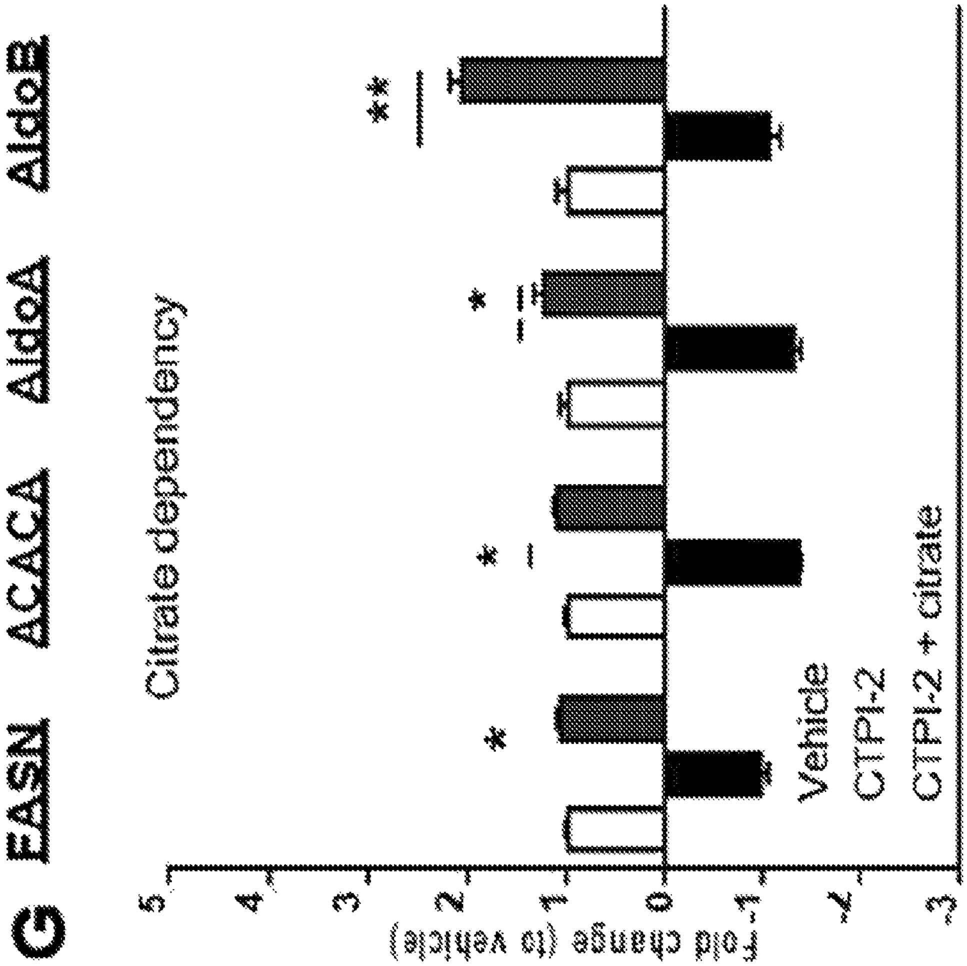
Figure 6H:
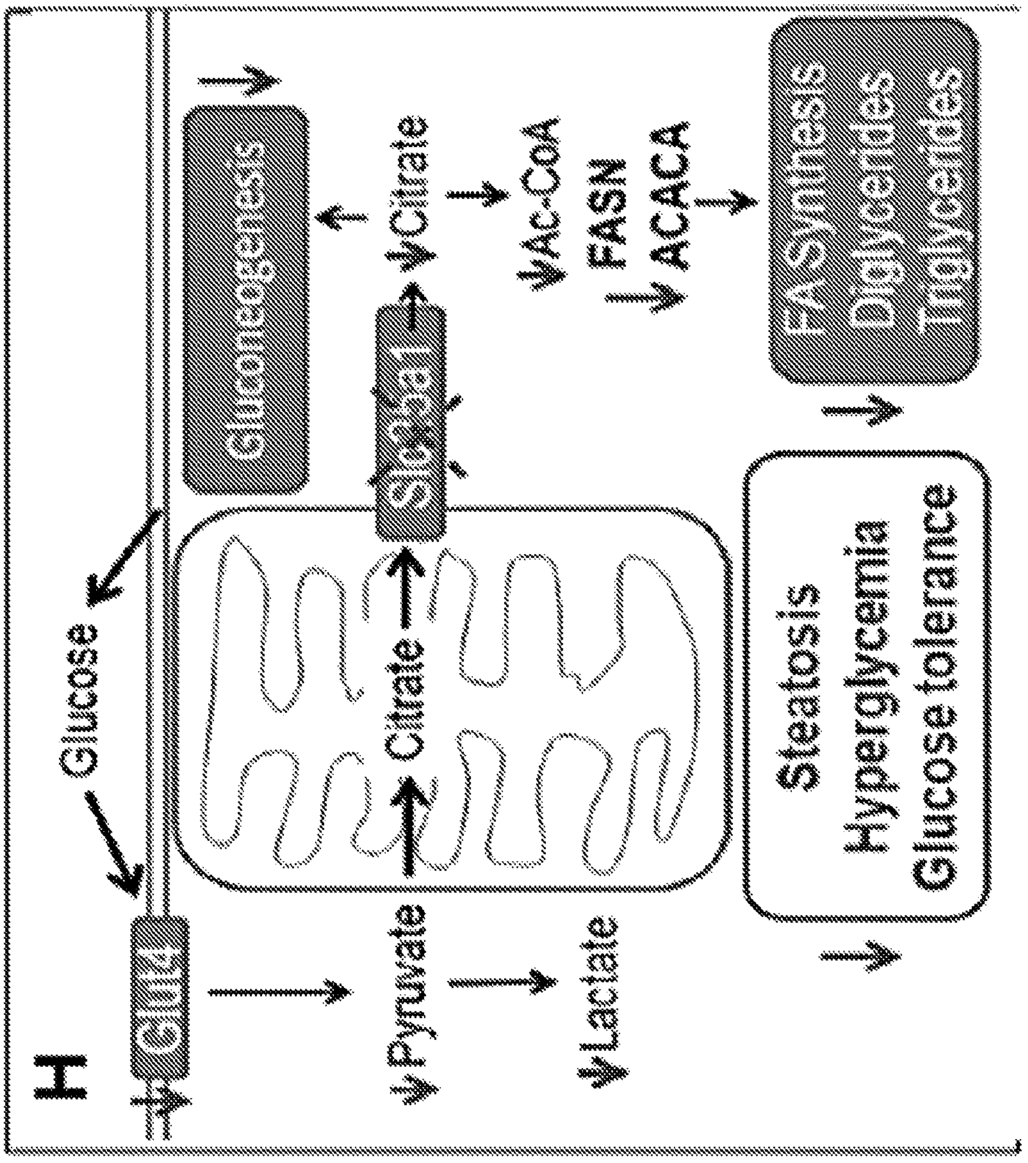

To corroborate the direct effect of CTPI-2 and of citrate in the regulation of the genes identified by our analysis, the effects of the drug and of citrate supplementation in tissue culture cells were explored. The results revealed that the expression of genes involved in FA synthesis, FASN and ACACA, as well as genes of the glycolytic/gluconeogenesis pathway, AldoA and Aldo/B, were inhibited by a short time treatment with CTPI-2 (5-12 hours) and completely rescued by citrate (FIG. 6G). Hence, these data not only demonstrate a direct role for citrate in the regulation of these genes but also underscore the specificity of CTPI-2 for the citrate pathway.

In summary (FIG. 6H), these data show that CTPI-2 inhibits glycolysis, PPAR-γ, and its down-stream target the glucose transporter GLUT4. The inhibition of glycolysis is manifested with the reduced concentration of pyruvate and lactate. In the liver, pyruvate is used for production of citrate in the mitochondria and subsequent export via SLC25A1, promoting lipogenesis through the synthesis of Ac-CoA. Thus, on one side, CTPI-2 reduces the availability of citrate and Ac-CoA, reducing the availability of the key precursors for lipogenesis and thereby extinguishing the major steps of de novo FA synthesis, of diacylglyceride and triacylglyceride production. On the other, given that citrate is also an allosteric activator of Fbp1, the reduced concentration of citrate itself or the reduced levels of lactate, which is also a gluneogenesis precursor, could explain the inhibition of gluconeogenesis. In conclusion, the combination of these activities accounts for the beneficial effects of CTPI-2 on steatosis, hyperglycemia and glucose homeostasis.

Figure 10A:
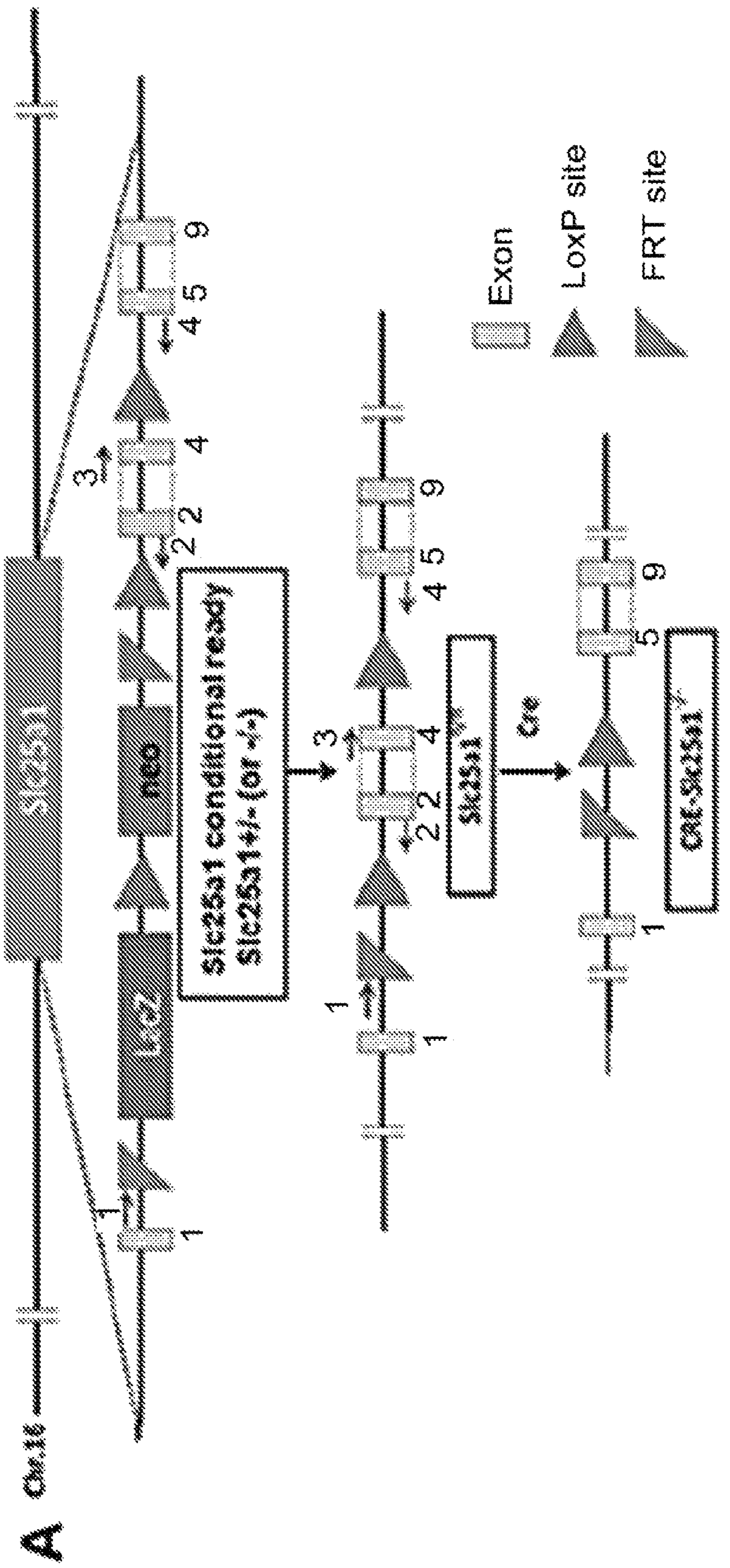
Figure 10B:
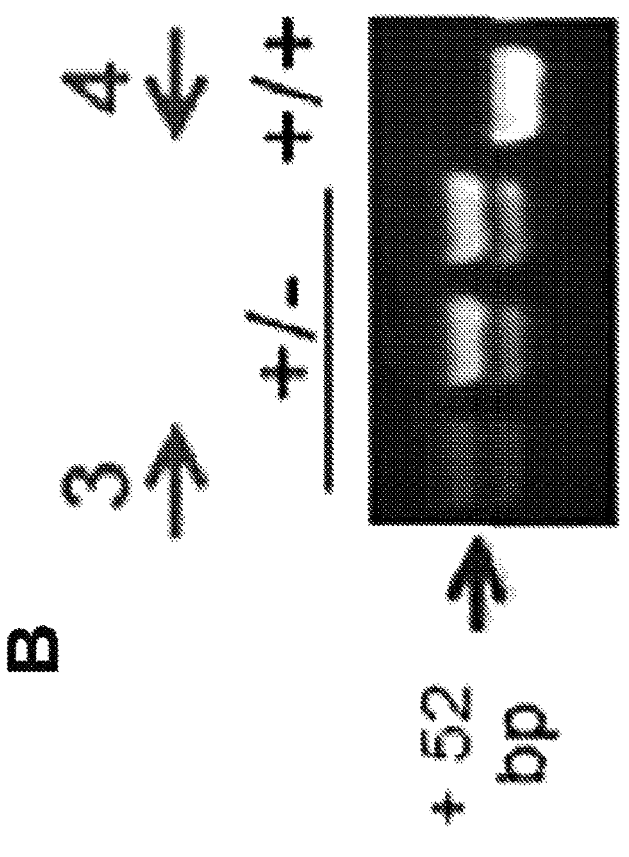
Figure 10C:
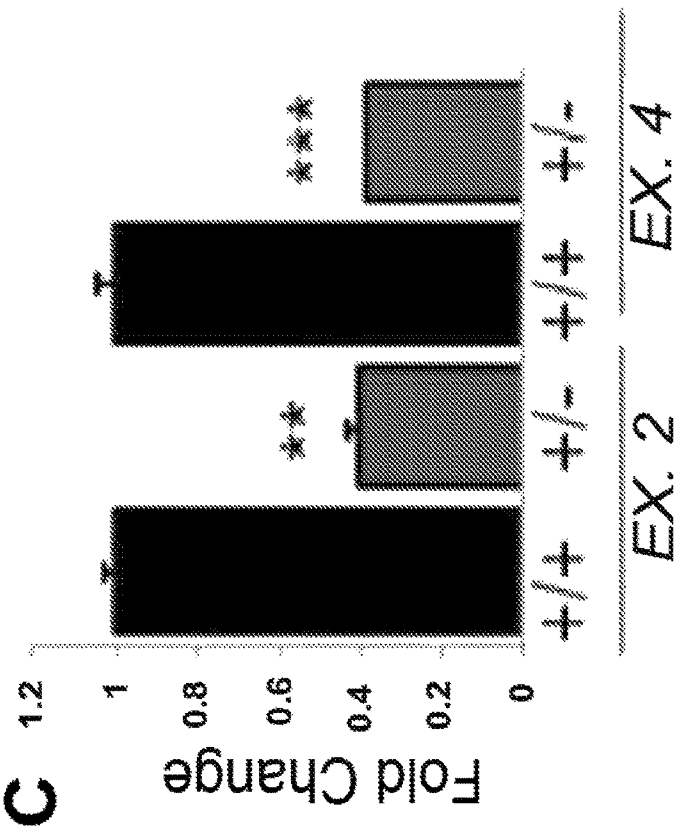
Figure 10D:
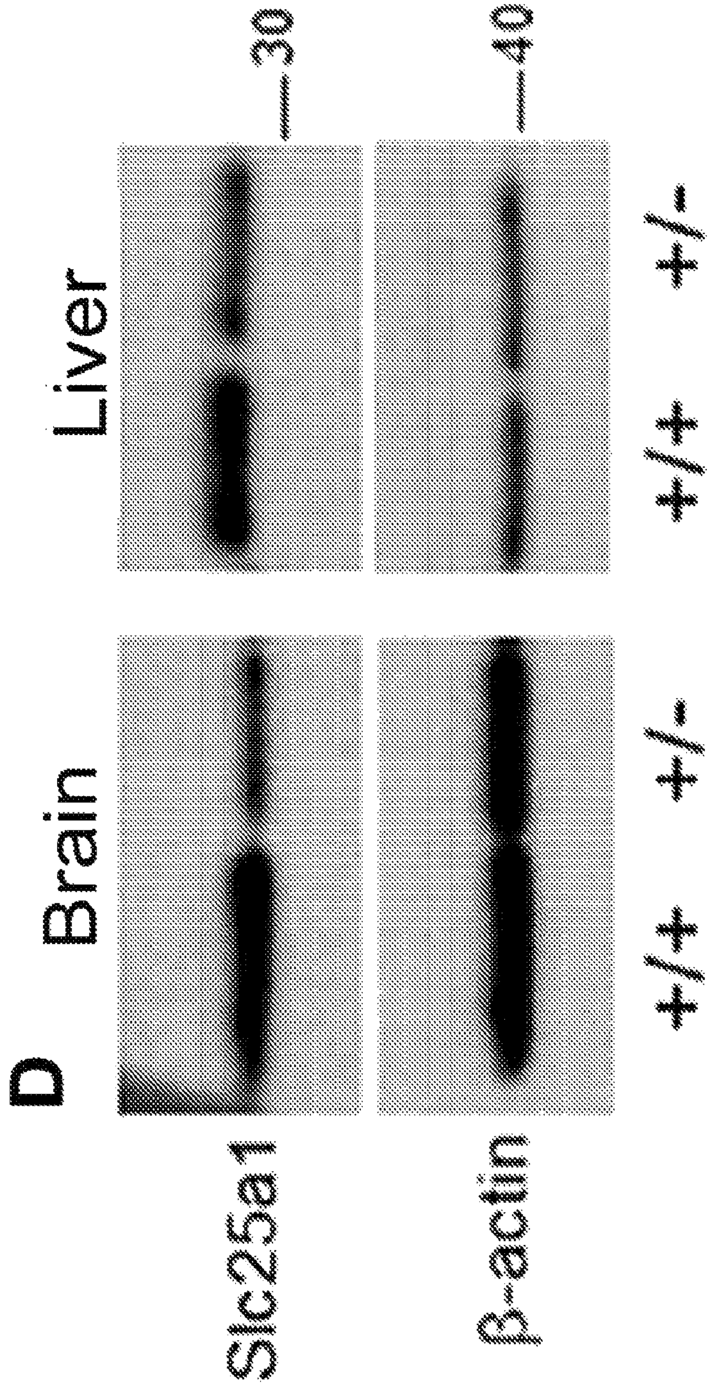

Genetic models of SLC25A1 deficiency recapitulate CTPI-2 activity. To confirm the role of SLC25A1 in diet induced obesity and fatty liver disease, different genetically modified models of SLC25A1 deficiency were used. Mice harboring a germline deletion of the Slc25a1 allele were initially purchased from the Mutant Mouse Resource Research Center (MMRRC, C57BL/6N-Slc25a1$^{tm1a(EUCOMM)Wtsi}$). The targeting vector allows for constitutive or conditional deletion of the Slc25a1 gene through the incorporation of an IRES:lacZ trapping cassette and a foxed promoter-driven Neo cassette which is inserted between intron 1 and 5 of the Slc25a1 gene on chromosome 16 (referred to-as tm1a allele, FIG. 10A, Skarnes et al. "A conditional knockout resource for the genome-wide study of mouse gene function," *Nature* 2011; 474(7351):337-342)). One copy of the cassette is present in the mouse genome, which is inserted in Chromosome 16 where the Slc25a1 gene is located, and targeting confirmation and allele integrity testing were performed by MMRRC. Deletion of two copies of the Slc25a1 gene leads to perinatal lethality and the phenotype of these mice will be described separately. The insertion of the tm1a targeting cassette disrupts mRNA translation and Slc25a1$^{+/-}$ embryos have a 50% reduction of the mRNA and protein levels (FIG. 10C-D).

Figure 7B:
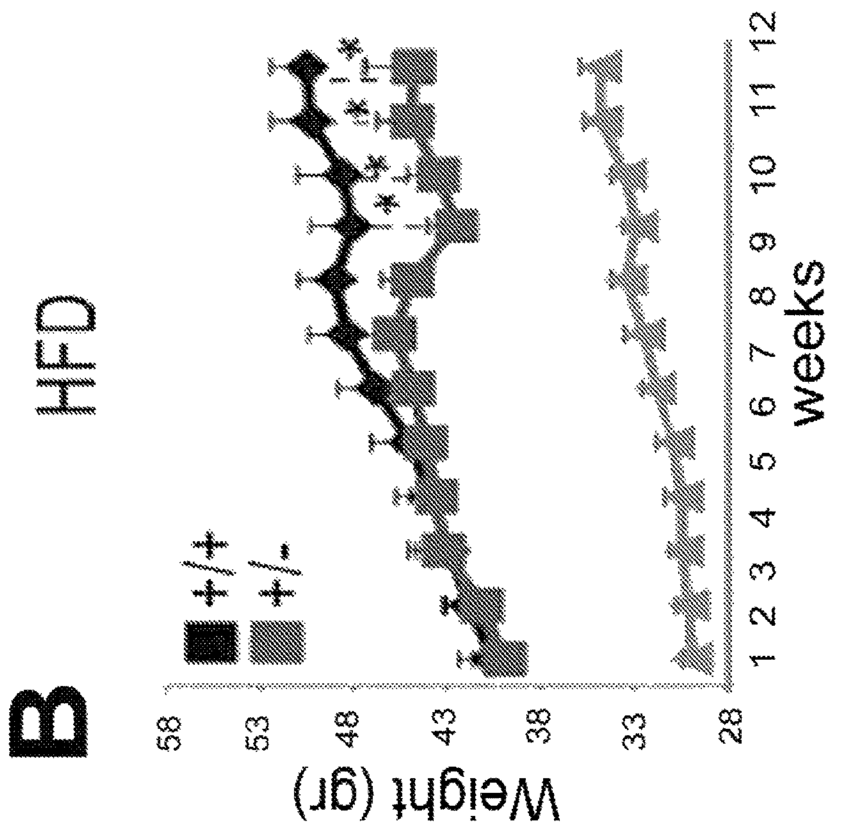
FIGS. 7A-J show that genetic models of Slc25a1 gene deficiency recapitulate the activity of CTPI-2.
Figure 7A:
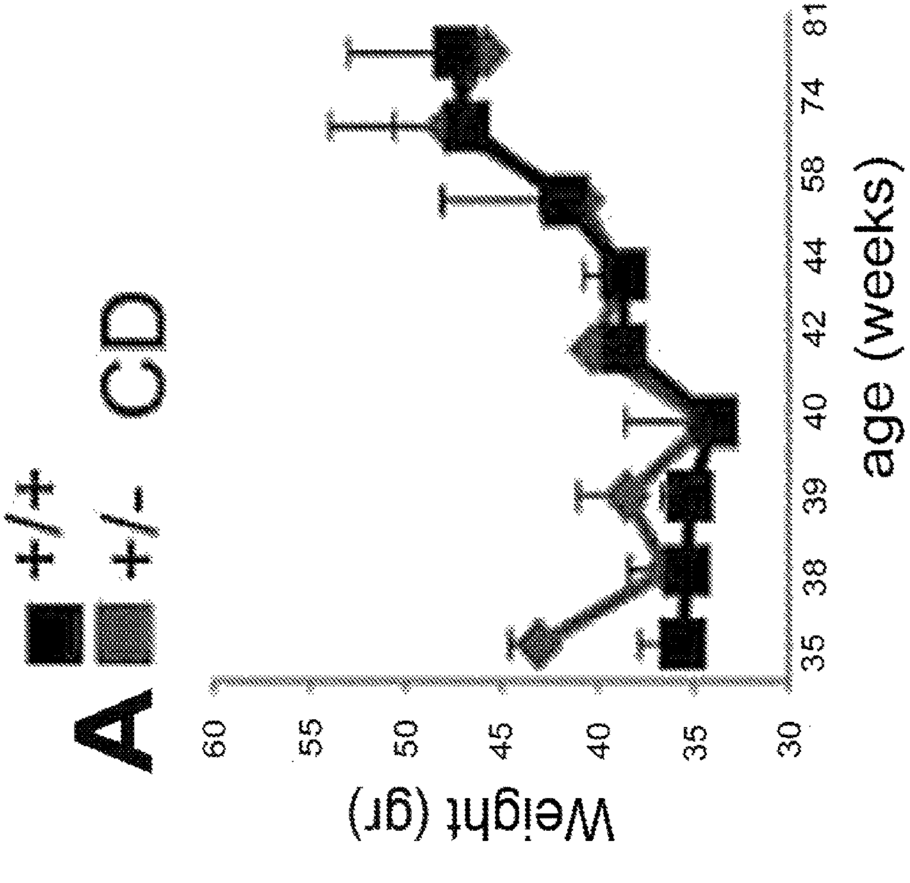
Figure 7D:
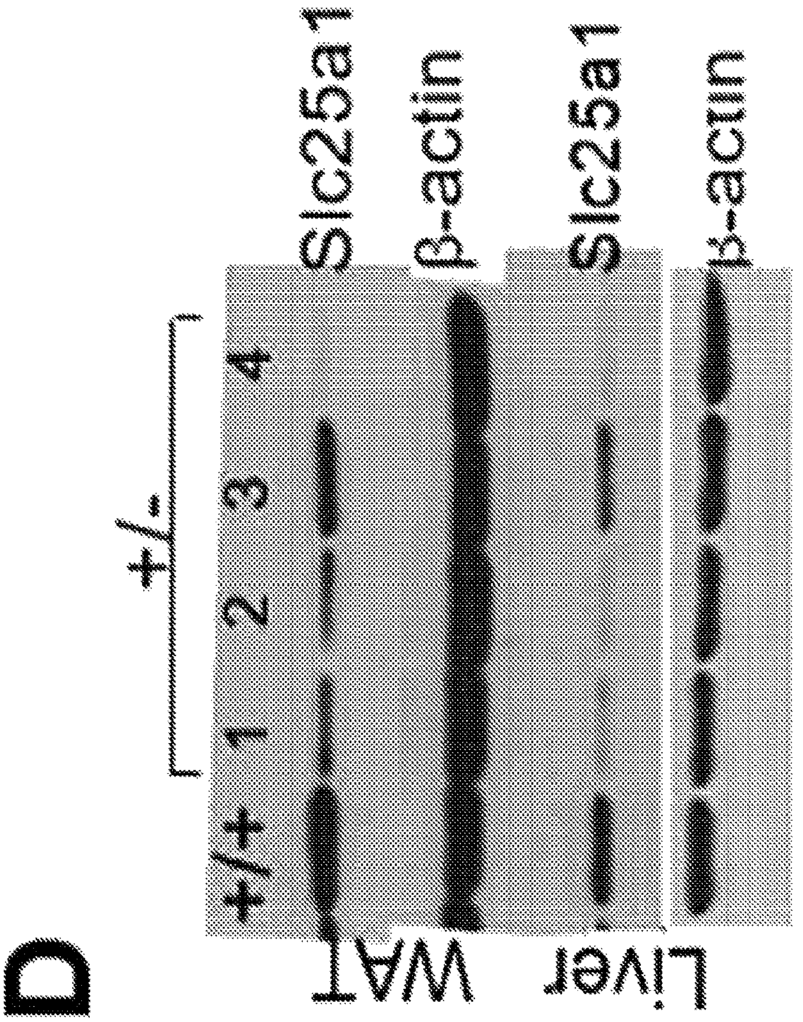
Figure 7C:
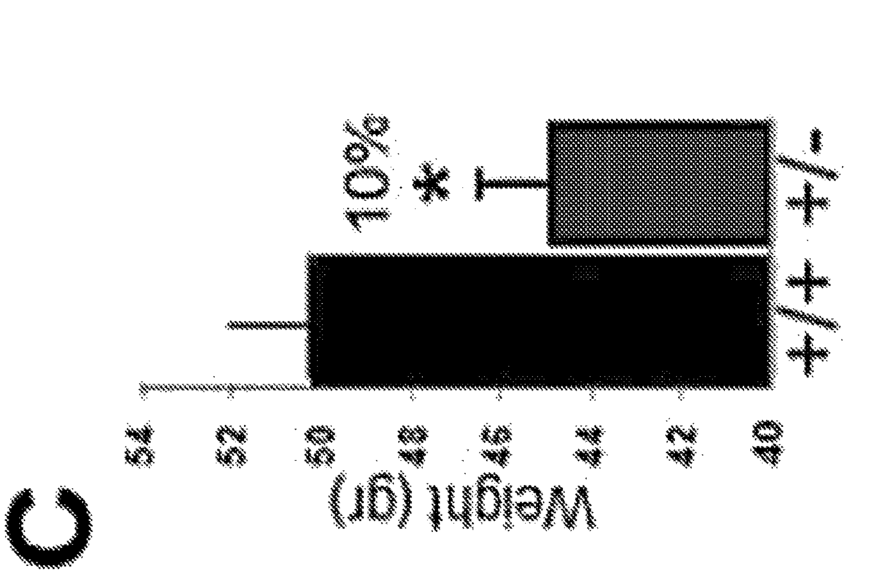
Figure 7F:
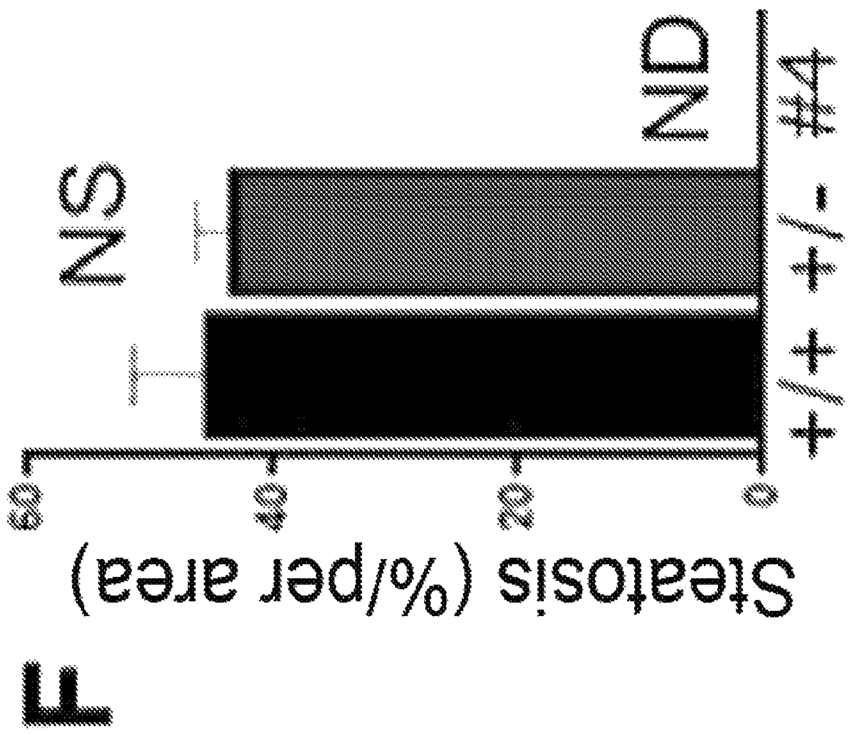
Figure 7E:
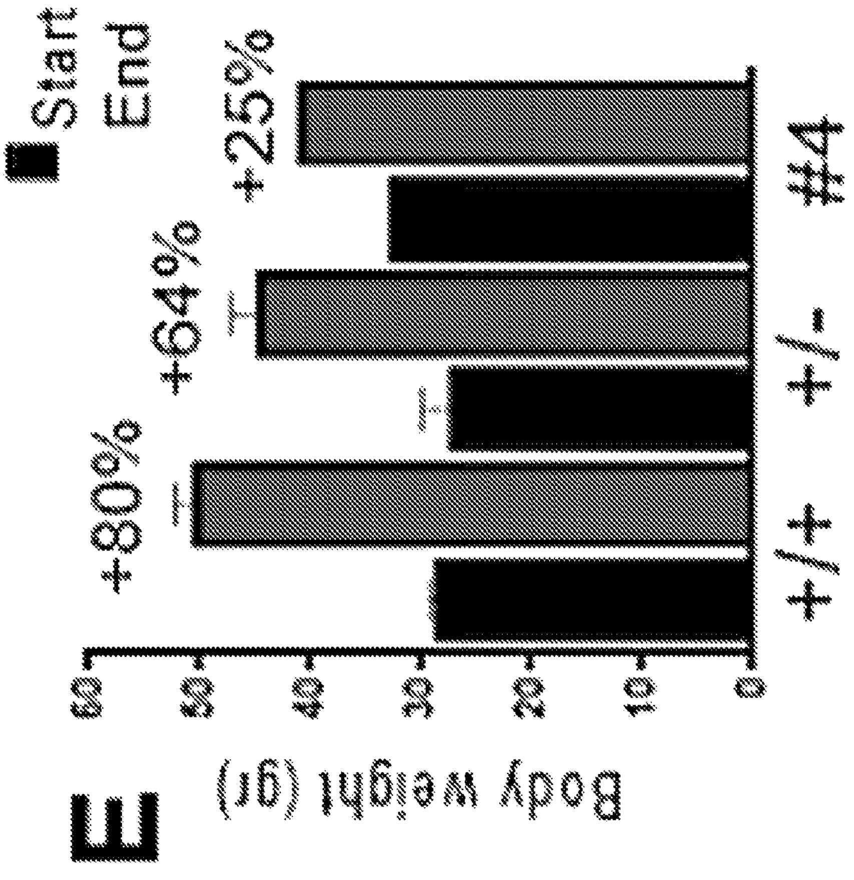
Figure 7G:
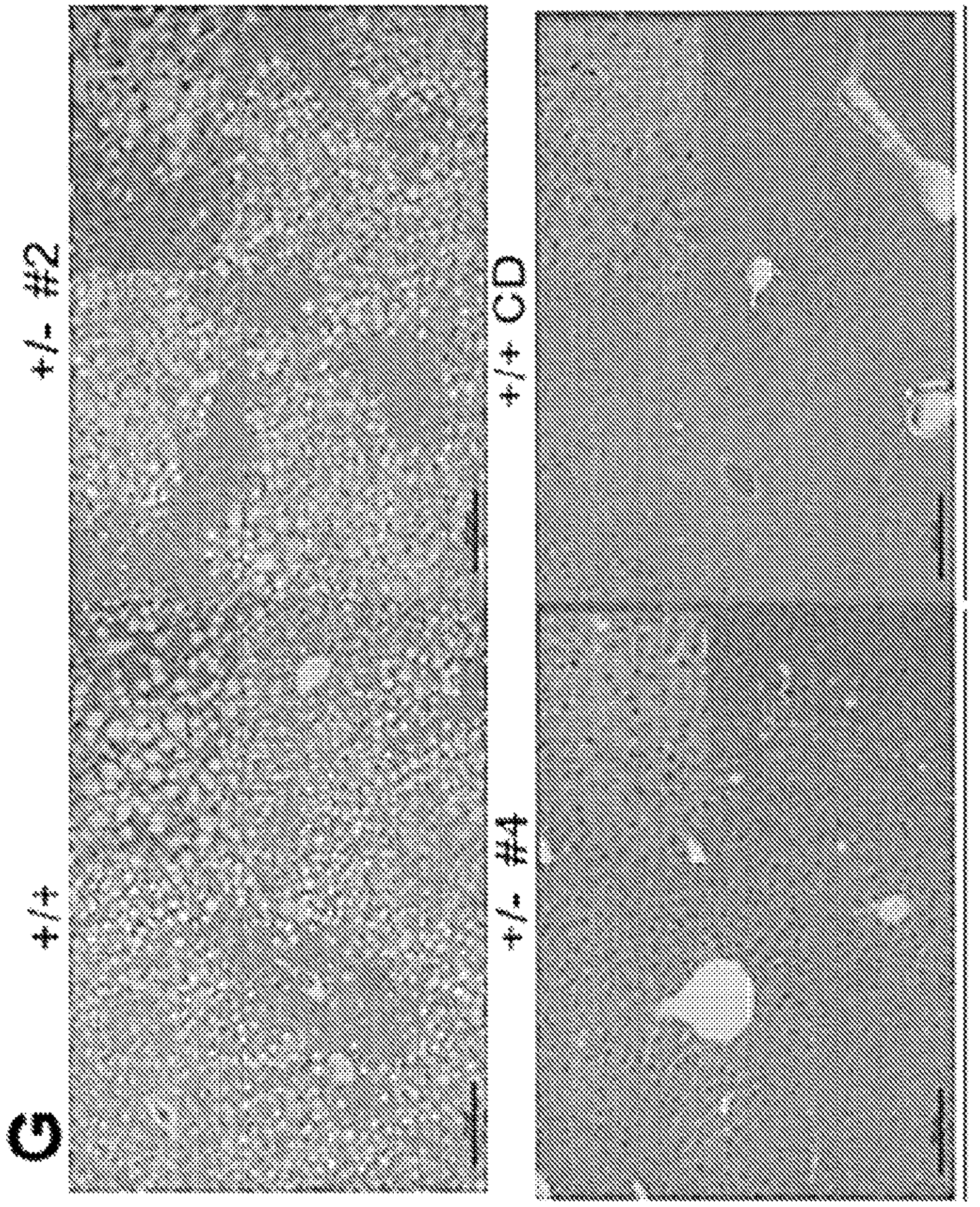

Several generations of Slc25a$^{+/-}$ mice were analyzed and it was found that these mice have body weight essentially comparable to, and live as long as, wild-type mice, demonstrating that the Slc25a1 gene is not haplo-insufficient in post-natal life (FIG. 7A). However, when fed with the HFD, Slc25a1$^{+/-}$ mice displayed less body weight gain (10%) compared to wild-type animals (FIG. 7BC). Importantly, significant extent of heterogeneity in the levels of expression of Slc25a1 protein was observed in the heterozygous HFD-fed mice, as some of these animals showed virtually no expression of the protein in both the adipose tissue and the liver, compared to others with intermediate loss of expression (mouse #4, FIG. 7D). Collectively, all heterozygous mice gained less weight under the HFD, but such reduction was significantly more pronounced in mice where Slc25a1 expression was absent in the adipose tissue (FIG. 7E). Strikingly however, there was no significant effect of Slc25a1 hemizygosity on liver steatosis, except for mice with severe depletion of Slc25a1 protein in both the liver and adipose tissue, which were completely protected from steatosis (FIG. 7F-G). These results imply that the activity of Slc25a1 is dose-dependent and rate-limiting in the adipose tissue under conditions of metabolic overload imposed by the HFD, given that a reduction of dosage was sufficient to blunt body weight gain, but not in the liver, where only mice with nearly complete loss of Slc25a1 protein in both tissues were resistant to steatosis.

Figure 7H:
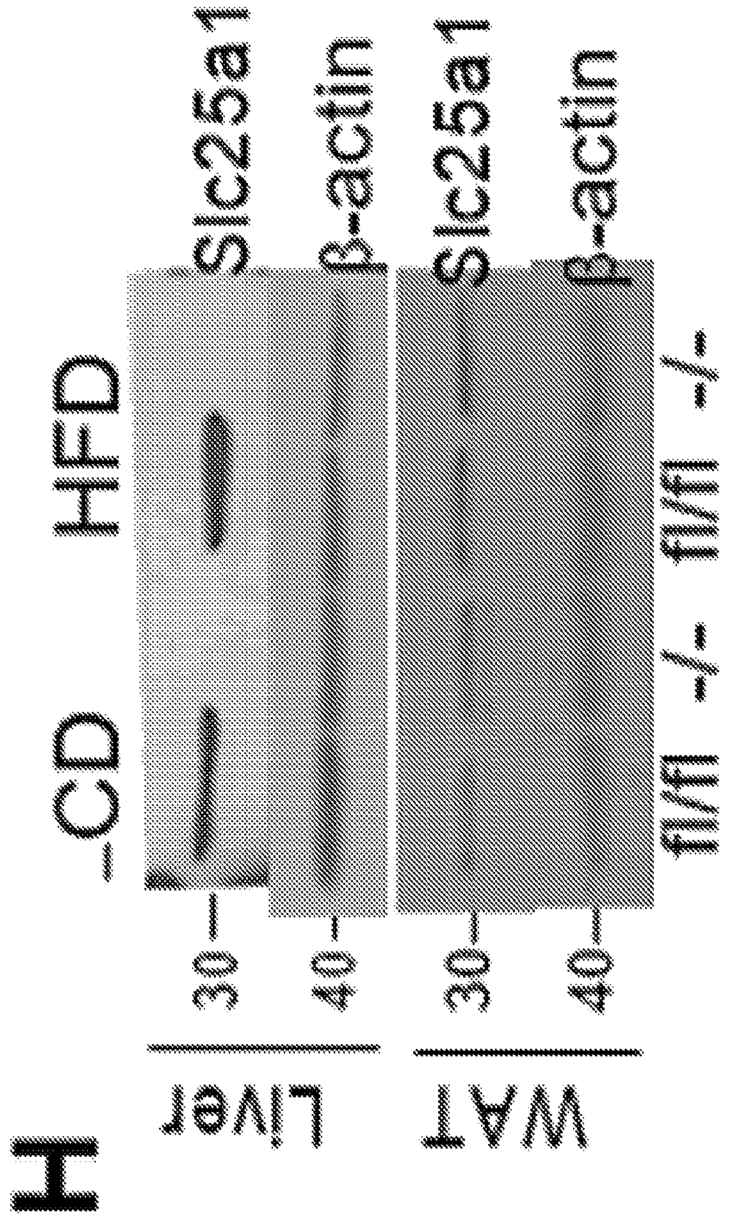
Figure 7I:
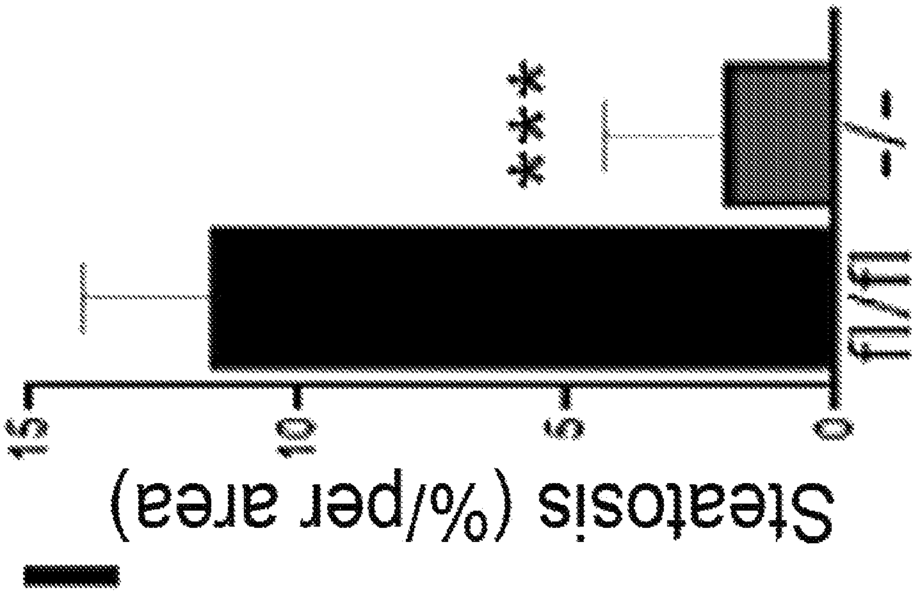
Figure 7J:
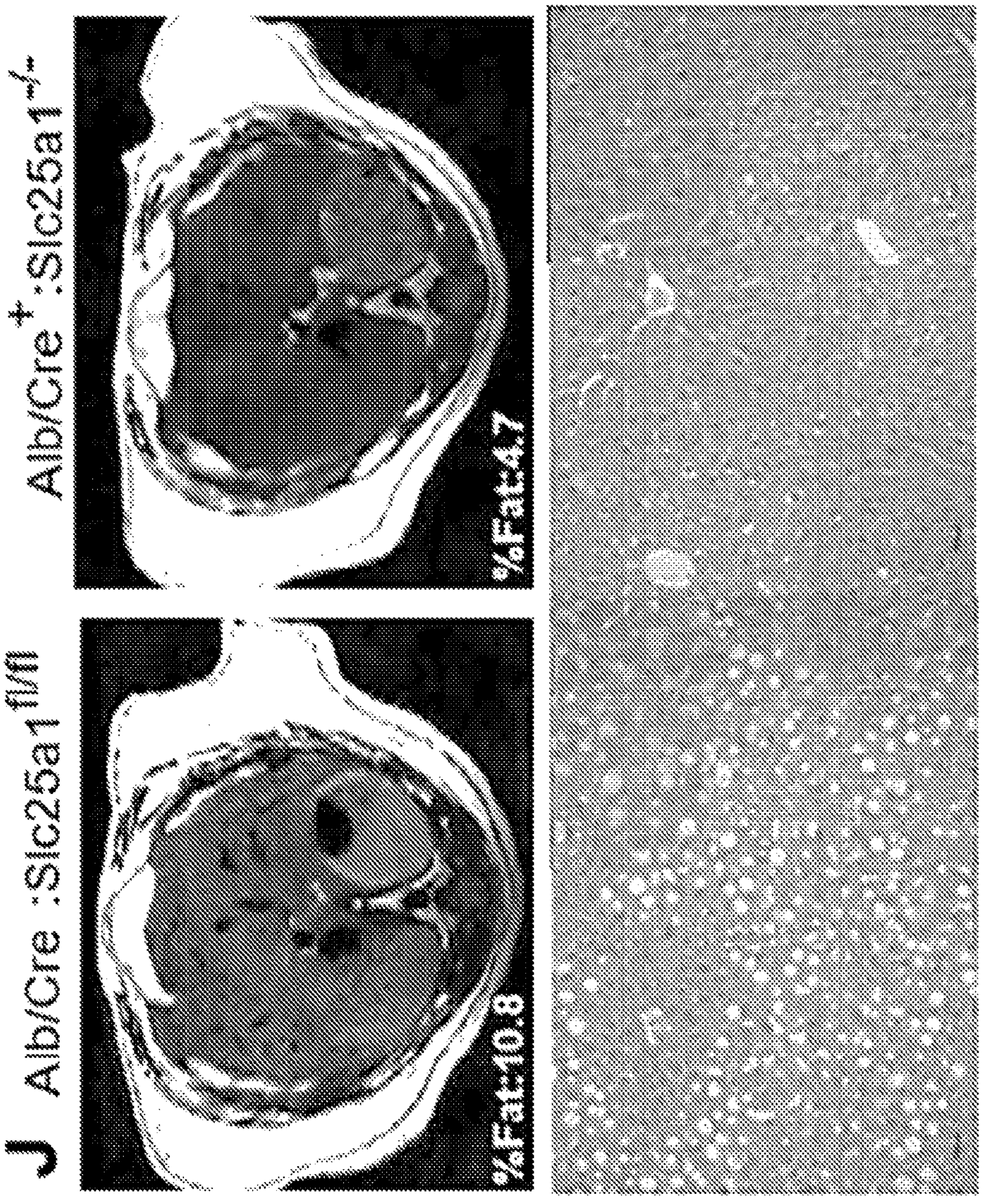
Figure 11A:
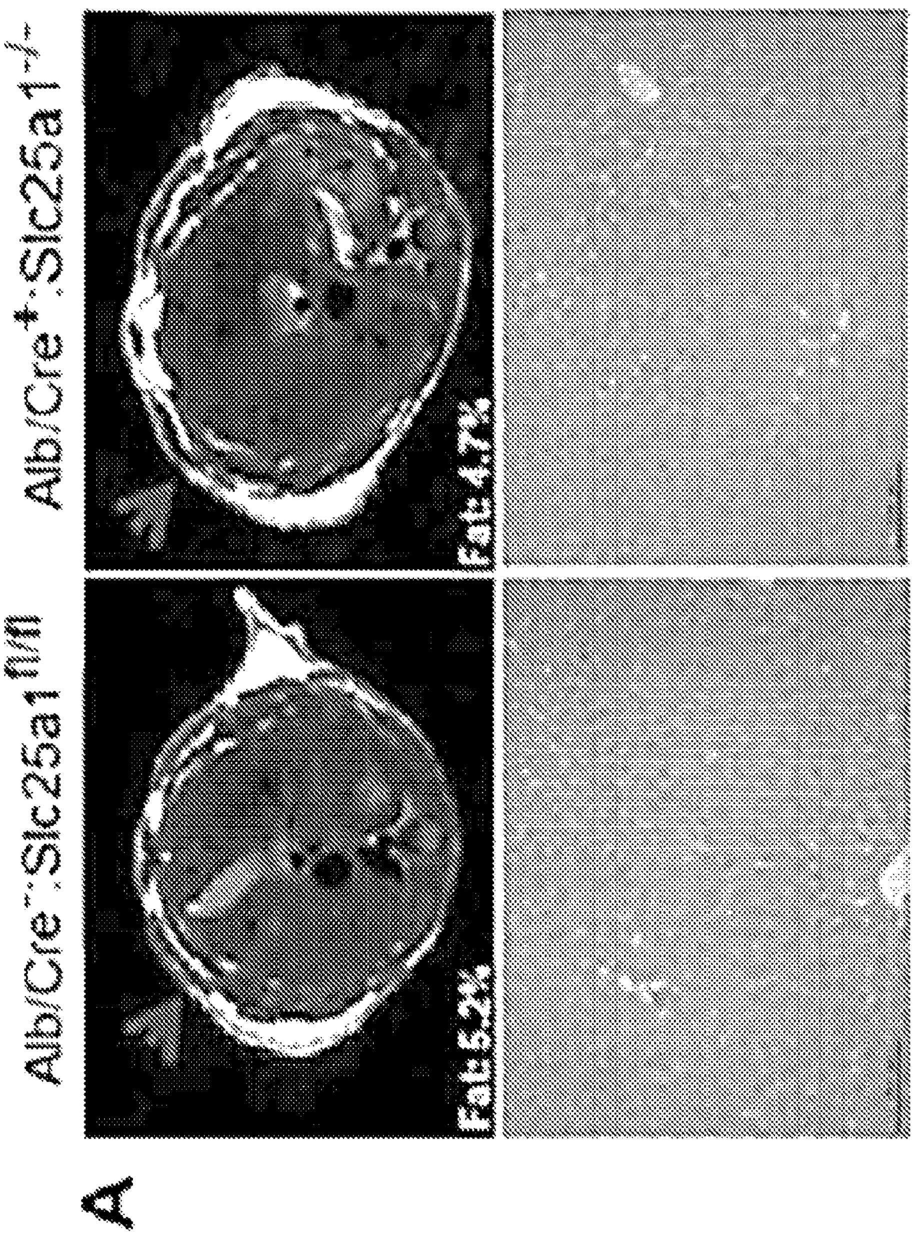
FIGS. 11A-E show the phenotype(s) of Slc25a1 deficient mice.
Figure 11B:
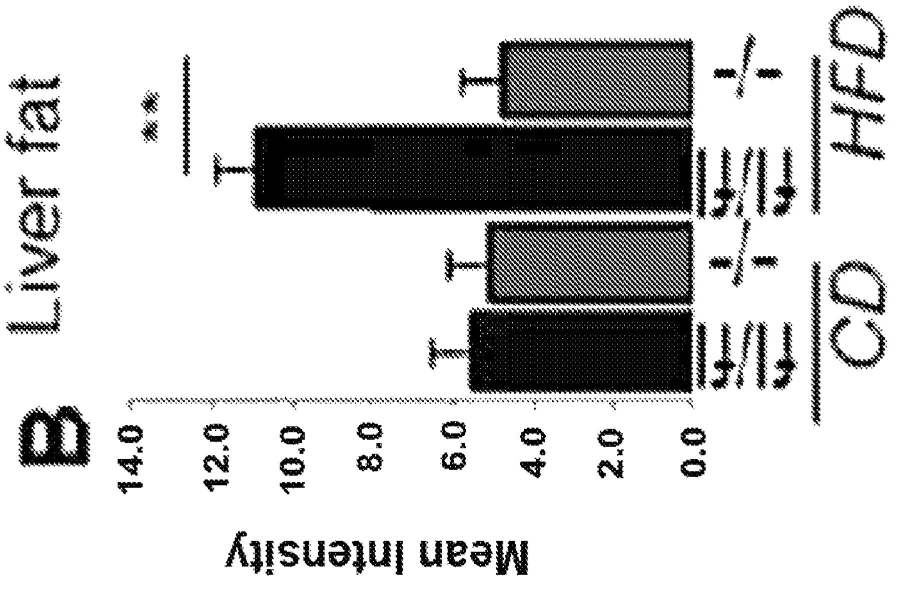
Figure 11C:
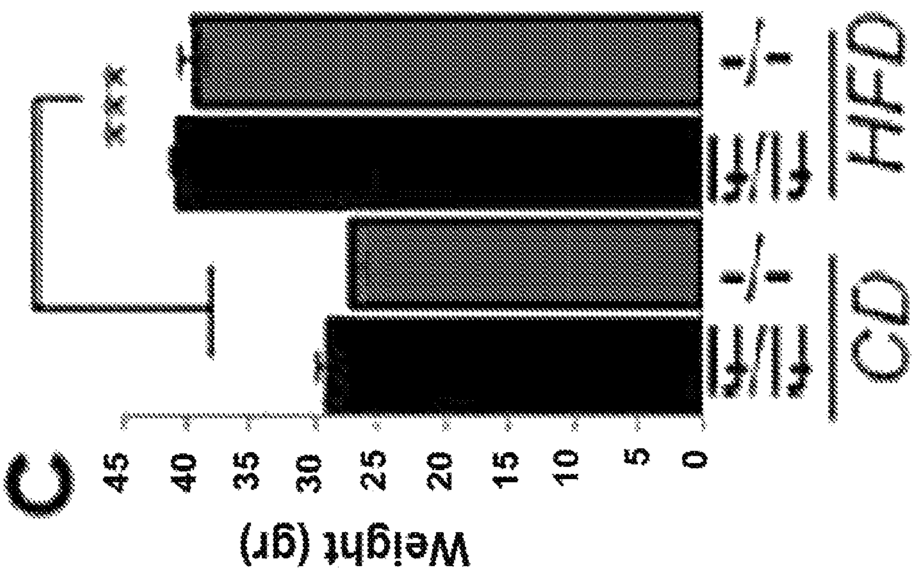
Figure 11D:
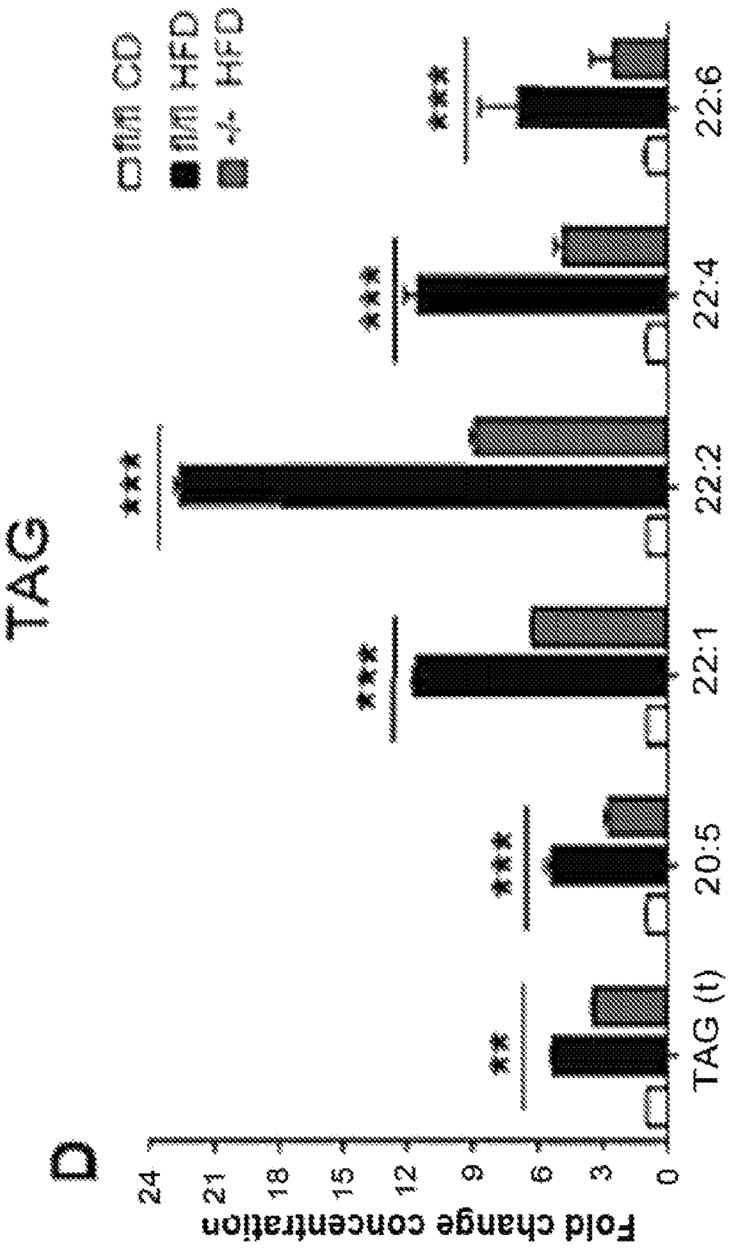
Figure 11E:
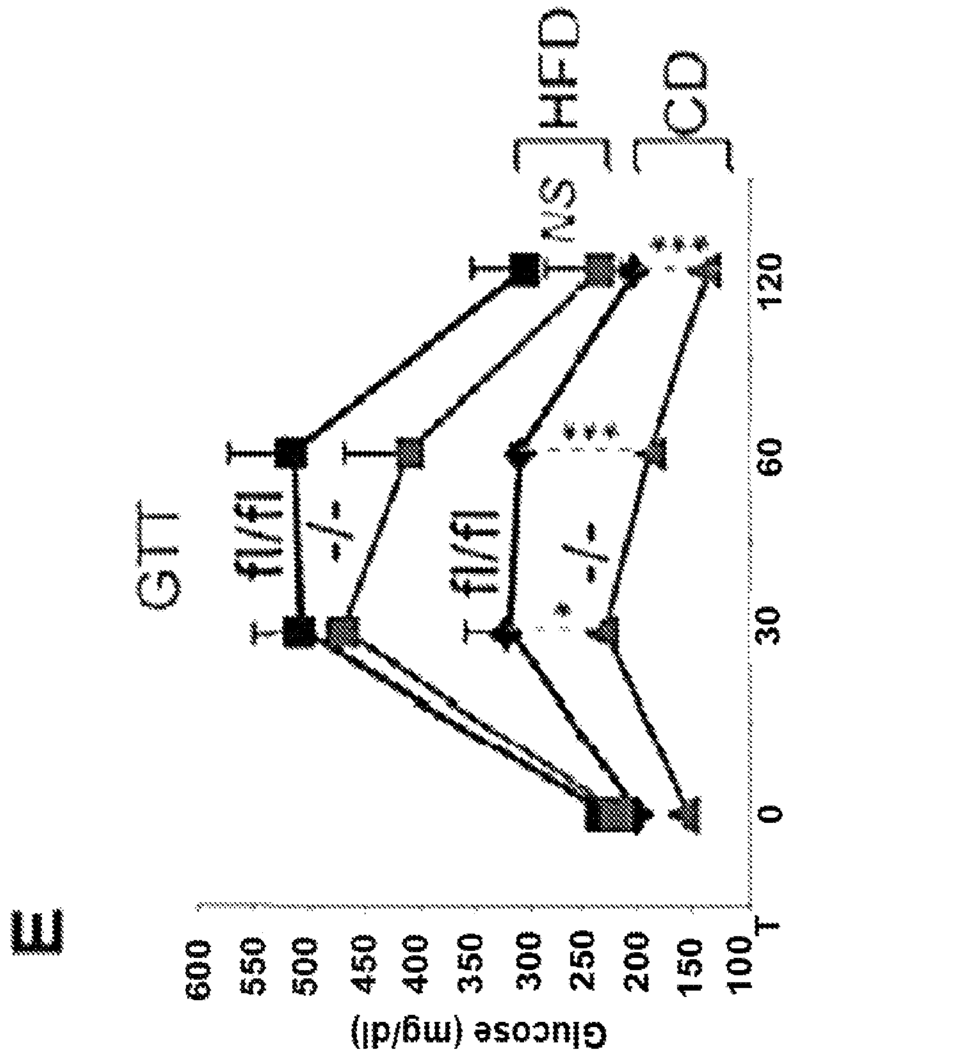

Given the above results, the contribution of liver-expressed Slc25a1 was dissected. Mice with the targeted insertion of LacZ and Neo cassettes (Slc25a1$^{+/-}$) were first crossed with mice expressing the Flpase recombinase gene, giving raise to floxed/floxed Slc25a1 alleles (Slc25a1$^{fl/fl}$, FIG. 10E-G). A generation of these mice was then crossed with Tg(Alb-cre)21Mgn (Alb-Cre), where the Cre gene is under control of the Albumin promoter/enhancer elements, generating Alb/Cre$^{+}$:Slc25a1$^{-/-}$ mice as well as control Alb/Cre$^{-}$:Slc25a1$^{fl/fl}$ mice. This approach leads to complete loss of the Slc25a1 mRNA and protein in the liver, while the levels of Slc25a1 remain normal in the adipose tissue, as expected (FIG. 7H). Cre/Alb$^{+}$:Slc25a1$^{-/-}$ are born at the expected Mendelian ratio, are viable, and show a normal liver histology, normal body weight and normal liver fat content (FIG. 11A-C). Consistent with previous results with the CTPI-2, when fed the HFD, Cre/Alb$^{+}$:Slc25a1$^{-/-}$ mice were largely, although not completely, protected from steatosis as assessed with immunohistochemistry and Magnetic Resonance Imaging (MRI) (FIG. 7I-J). Furthermore, analysis of the lipid profile demonstrated a reduction of long-chain triglyceride accumulation (FIG. 11D) a trend of improvement in the ability to clear blood glucose relative to wild-type mice (FIG. 11E).

The results illustrate that the phenotypes elicited by CTPI-2 largely overlap with those seen in the genetic models of Slc25a1 gene deficiency. However, CTPI-2 more effectively prevented liver steatosis relative to Cre/Alb$^{+}$:Slc25a1$^{-/-}$ mice. Given the important role played by the adipose tissue metabolism and by inflammatory signals originating therein in the evolution NASH, this difference could depend upon CTPI-2 targeting of Slc25a1 in both the liver and WAT.

The data provided herein show that SLC25A1 inhibition is beneficial to NASH and metabolic syndrome, alleviating steatosis, inflammation and improving glucose homeostasis. These results show that the mechanisms of action of SLC25A1 inhibition differ from other inhibitors of the upstream regulatory steps of lipogenesis. Blocking SLC25A1 activity, as shown herein, depletes the pool of citrate and of Acetyl-Coenzyme A negatively regulating the lipogenetic pathway. Unlike the SLC25A1 liver specific knock-out, the FASN knock-out in the liver paradoxically exacerbated steatosis under specific dietetic conditions, and these mice displayed elevated ketone bodies and elevated TAGs in the liver. These effects were in part attributed to the inhibition of PPARα activity, as they could be rescued by PPARα agonists. A potential explanation for the differential effects of Slc25a1 inhibition and the FASN knock-out, however, also lies in the concentration of the pool of citrate that we have shown to be decreased by SLC25A1 inhibition, and which theoretically should increase when FASN is inhibited, due to a decrease in utilization in the downstream reactions. Indeed, citrate is not only the fundamental metabolic precursor for FA synthesis but is also an allosteric activator of gluconeogenic enzymes, such that when the citrate concentration drops gluconeogenesis is induced. Unlike in the FASN knock-out, where gluconeogenesis was increased, in CTPI-2 treated mice gluconeogenesis was depressed and repression of some of the gluconeogenesis enzymes was rescued by citrate in vitro. Given that glucose can enter the FA synthetic pathway, inhibition of gluconeogenesis can contribute to inhibition of steatosis and TAG depletion, and can also explain the improvement of hyperglycemia and glucose intolerance.

Also, as shown herein, inhibition of SLC25A1 reduces the pro-inflammatory environment systemically and in the liver, reducing macrophage infiltration. Furthermore, in vitro studies indicated that epithelial cells over-expressing SLC25A1 co-cultured with macrophages can inhibit the M1 phenotype. The RNA sequencing experiments suggested that CTPI-2 inhibits bile acid biosynthetic pathway. Finally, phenotypes elicited by CTPI-2 overlap with those seen in the genetic models of SLC25A1 deficiency further corroborating the notion that SLC25A1 is the bona fide target of the drug. The biological activity of CTPI-2 in NASH has proven to be appealingly effective and broad, acting on multiple aspects of this disease and thus providing strong rationale for pharmacological inhibition of SLC25A1 in this disease.

What is claimed is:

1. A method for treating non-alcoholic fatty liver disease (NAFLD) or nonalcoholic steatohepatitis (NASH) in a subject, comprising administering to a subject with NAFLD/NASH an effective amount of a SLC25A1 inhibitor according to citrate-transporter inhibitor-2 (CTPI-2):

CPTI-2

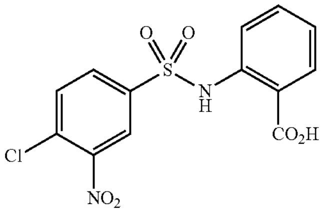

2. The method of claim 1, wherein the SLC25A1 inhibitor decreases liver steatosis in the subject.

3. The method of claim 1, wherein the SLC25A1 inhibitor decreases inflammation in the subject.

4. The method of claim 1, wherein the SLC25A1 inhibitor reduces hyperglycemia and glucose intolerance in the subject.

5. The method of claim 1, wherein administration of the SLC25A1 inhibitor prevents hepatocellular carcinoma.

* * * * *